(12) United States Patent
Hasegawa et al.

(10) Patent No.: US 7,104,951 B2
(45) Date of Patent: *Sep. 12, 2006

(54) ENDOSCOPE APPARATUS WITH DRUM PART TO WIND INSERTION PART THEREAROUND

(75) Inventors: Hiroshi Hasegawa, Oume (JP); Seiji Kimura, Hino (JP); Nobuyuki Saruya, Hino (JP); Shinji Fujikawa, Hachioji (JP); Takakazu Ishigami, Tama (JP); Masahiro Kumakura, Sayama (JP); Yasufumi Shimoe, Fukuyama (JP)

(73) Assignee: Olympus Corporation, Tokyo (JP)

( * ) Notice: Subject to any disclaimer, the term of this patent is extended or adjusted under 35 U.S.C. 154(b) by 466 days.

This patent is subject to a terminal disclaimer.

(21) Appl. No.: 10/660,383

(22) Filed: Sep. 11, 2003

(65) Prior Publication Data

US 2004/0054259 A1 Mar. 18, 2004

Related U.S. Application Data

(63) Continuation of application No. 09/808,807, filed on Mar. 15, 2001.

(30) Foreign Application Priority Data

| Mar. 15, 2000 | (JP) | ................................. | 2000-072814 |
| Mar. 15, 2000 | (JP) | ................................. | 2000-072815 |
| Mar. 15, 2000 | (JP) | ................................. | 2000-072816 |
| Apr. 4, 2000 | (JP) | ................................. | 2000-102697 |
| Jan. 12, 2001 | (JP) | ................................. | 2001-005567 |
| Jan. 12, 2001 | (JP) | ................................. | 2001-005568 |

(51) Int. Cl.
*A61B 1/00* (2006.01)

(52) U.S. Cl. ........................ 600/102; 604/95; 600/146

(58) Field of Classification Search ................. 600/146, 600/102, 109, 114, 131, 139, 152; 604/280, 604/95

See application file for complete search history.

(56) References Cited

U.S. PATENT DOCUMENTS 5,323,899 A 6/1994 Strom et al.
5,531,664 A 7/1996 Adachi et al.

FOREIGN PATENT DOCUMENTS

JP 58-172905 11/1983
JP 1-138522 5/1989

(Continued)

*Primary Examiner*—Thor S. Campbell
(74) *Attorney, Agent, or Firm*—Scully, Scott, Murphy & Presser

(57) ABSTRACT

According to the present invention, an endoscope system having an insertion member thereof wound about a drum comprises an electronic endoscope, a drum, an angling input unit, a motor-driven angling unit, a camera control unit, a motor-driven angling control circuit unit, and a stowage case. A bending section included in an insertion member of the electronic endoscope is motor-driven to bend, and a solid-state imaging device is incorporated at the tip of the insertion member. The insertion member is wound about the periphery of the drum. The angling input unit is separated from the electronic endoscope, and used to enter a direction of bending in which a user wants to bend the bending section. The motor-driven angling unit is incorporated in the drum, and includes a driving source for driving a driving mechanism that drives the bending section. The camera control unit controls the solid-state imaging device, and includes a signal processor for processing an electric signal sent from the solid-state imaging device to generate a video signal. The motor-driven angling control circuit unit controls the movement of the bending section. The drum is rotatably stowed in the stowage case freely.

82 Claims, 50 Drawing Sheets

U.S. PATENT DOCUMENTS

| | | |
|---|---|---|
| 5,876,326 A | 3/1999 | Takamura et al. |
| 6,036,636 A | 3/2000 | Motoki et al. |
| 6,371,907 B1 | 4/2002 | Hasegawa et al. |

FOREIGN PATENT DOCUMENTS

| | | |
|---|---|---|
| JP | 1-204014 | 8/1989 |
| JP | 4-81711 | 3/1992 |
| JP | 4-35850 | 8/1992 |
| JP | 5-56486 | 8/1993 |
| JP | DE 197 48 795 A1 | 5/1998 |
| JP | 10-274743 | 10/1998 |

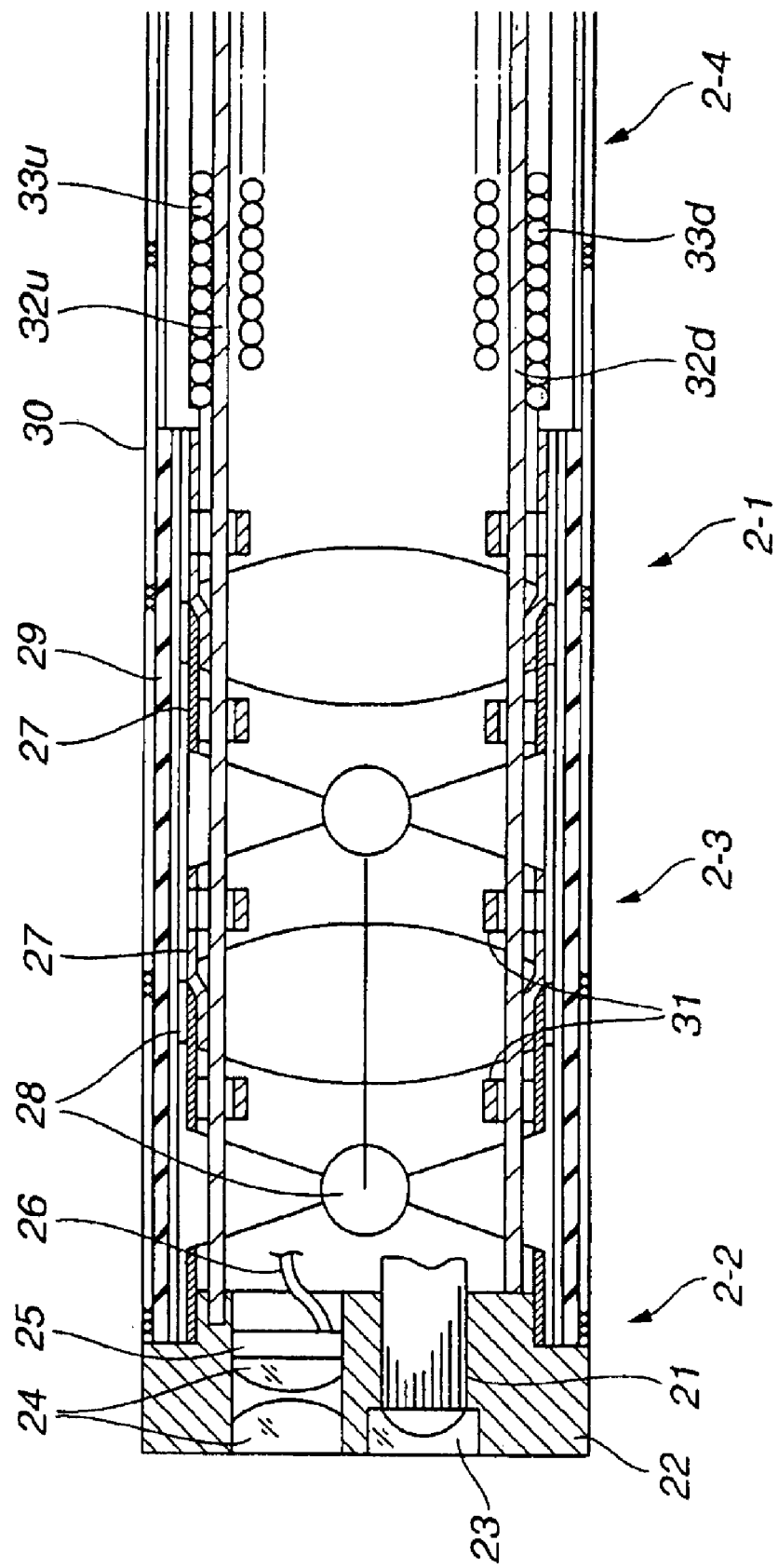

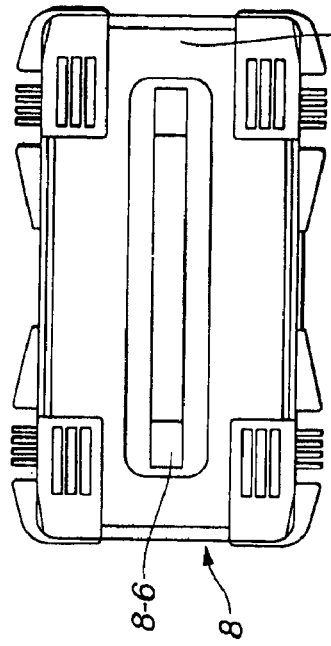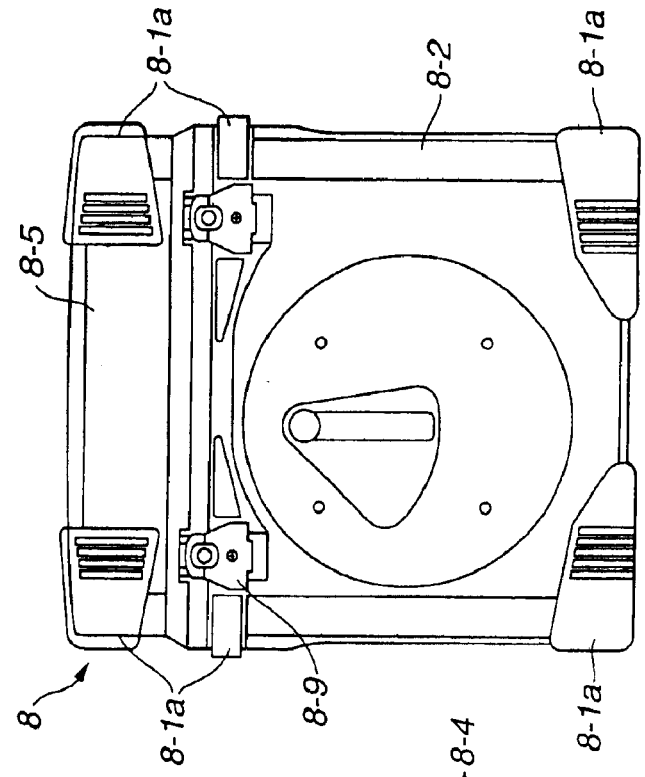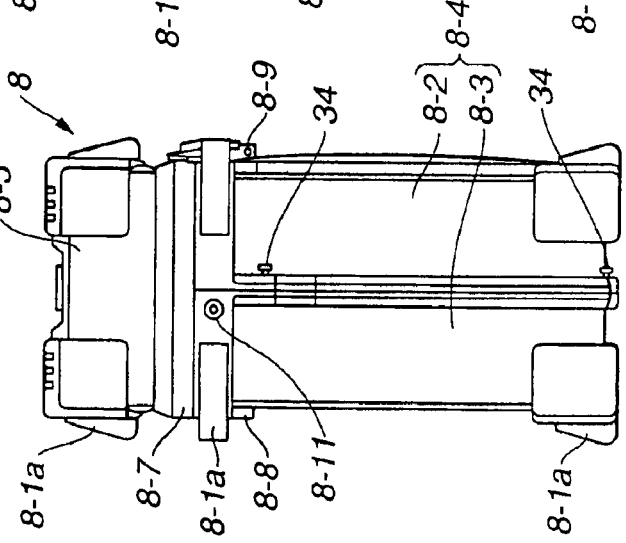

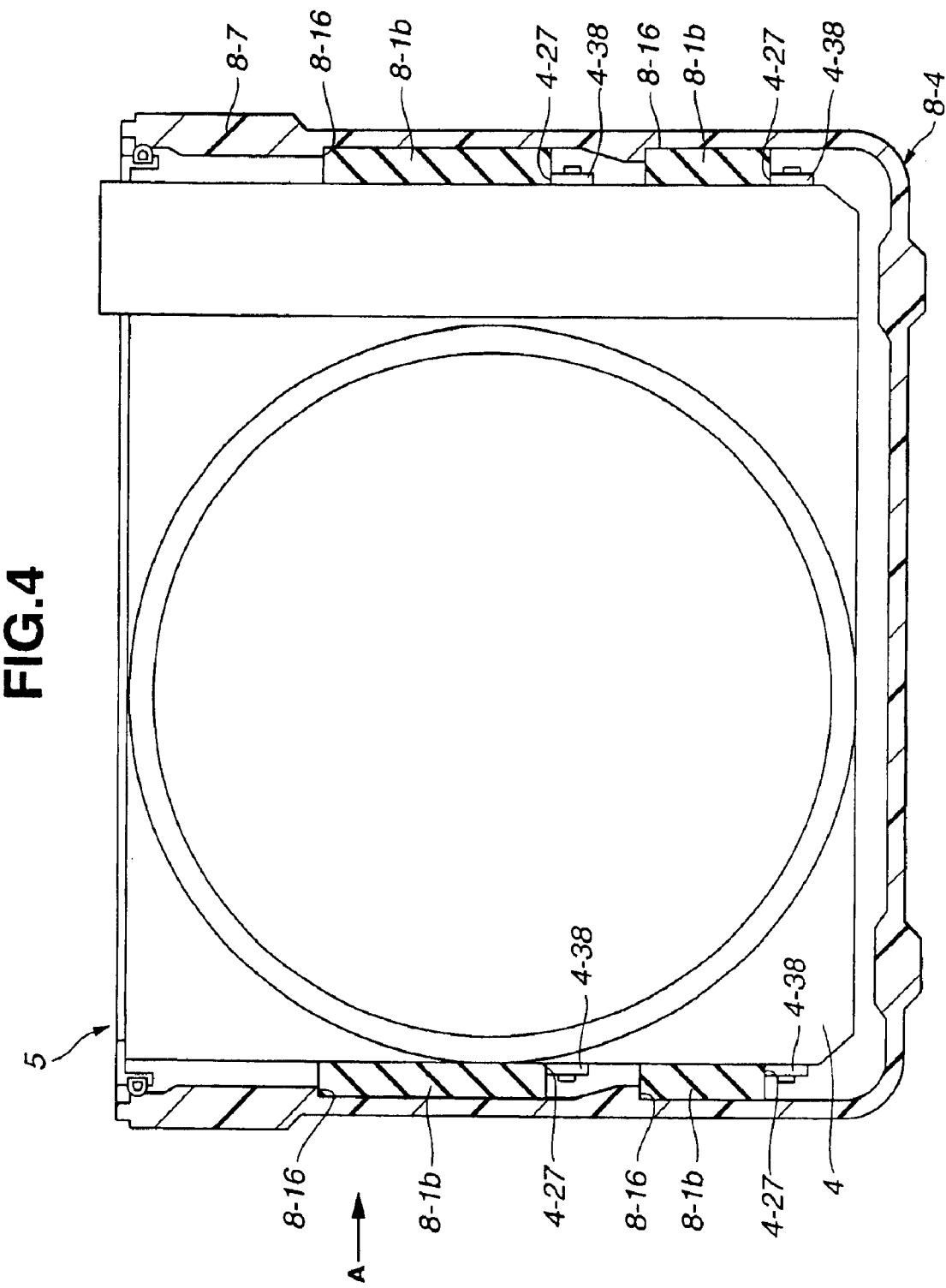

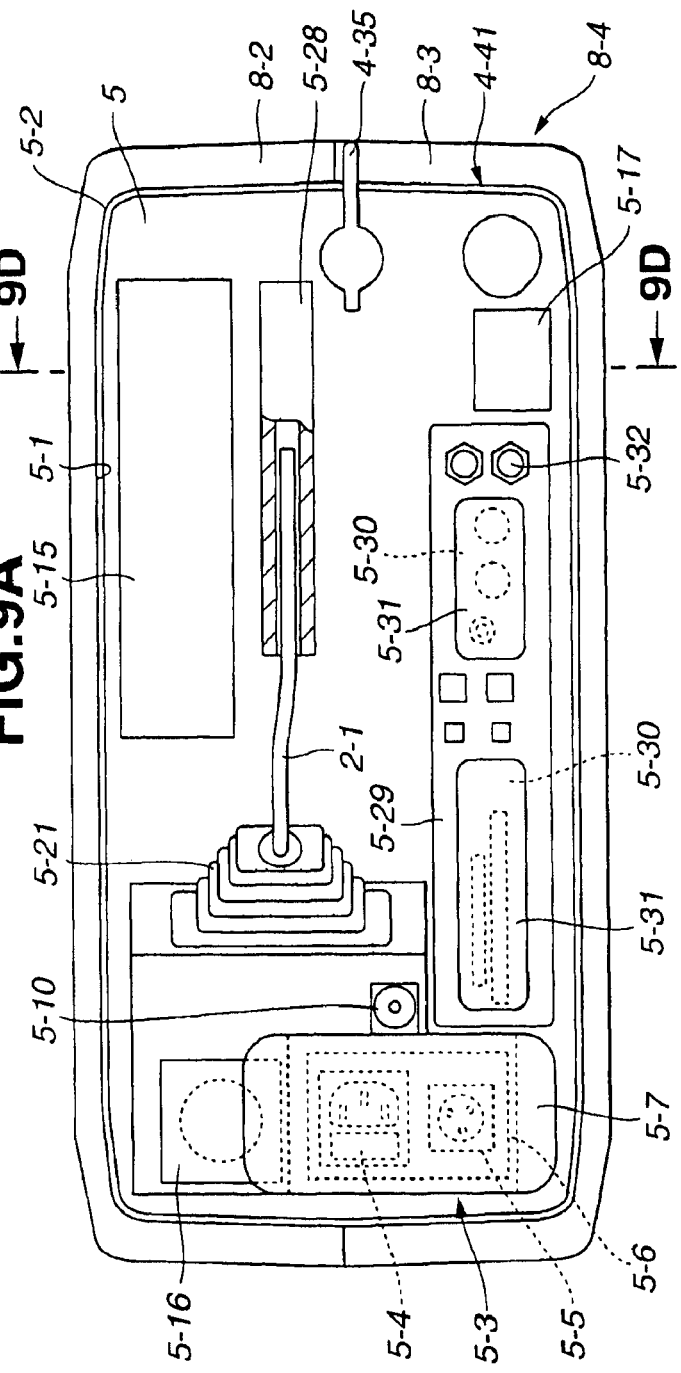
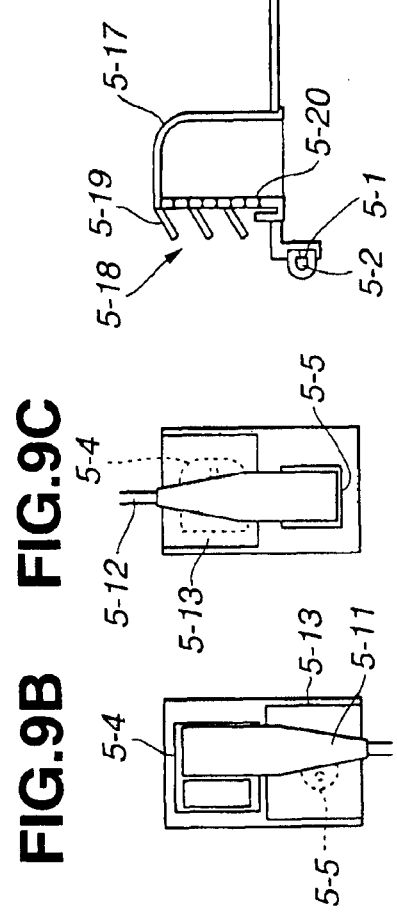

FIG.19
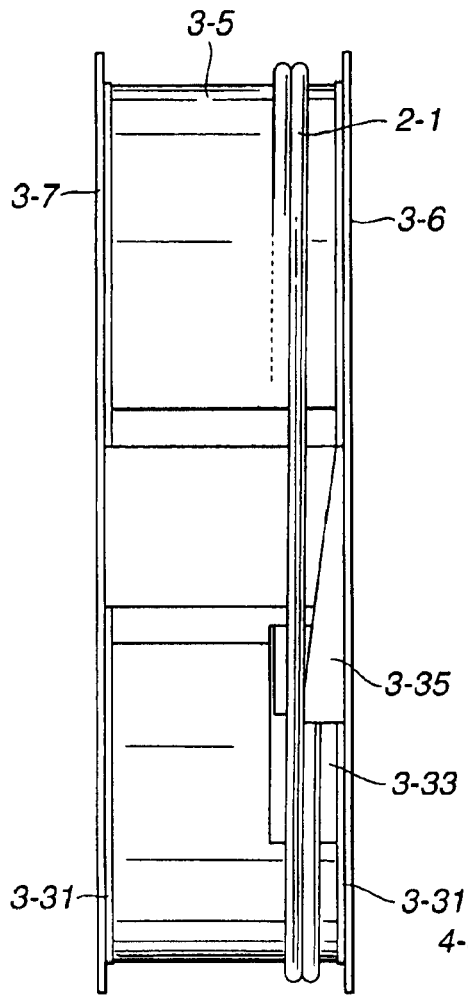
FIG.20A
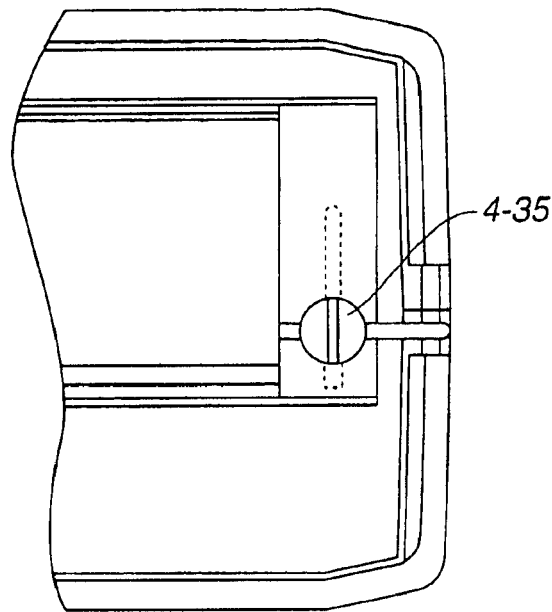
FIG.20D   FIG.20E
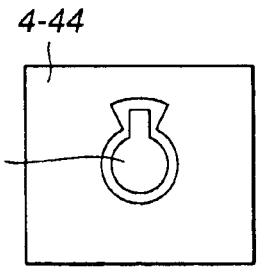   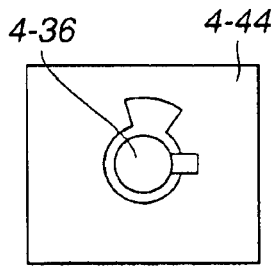
FIG.20B   FIG.20C
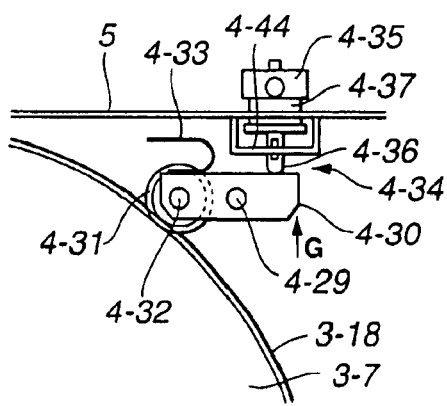   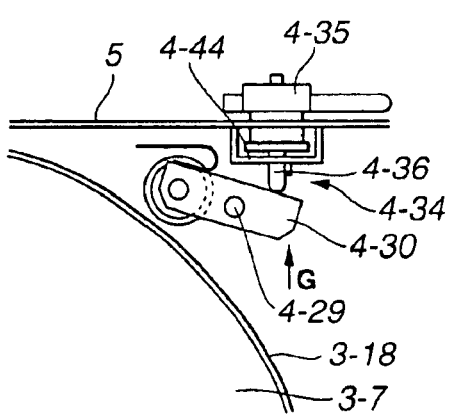

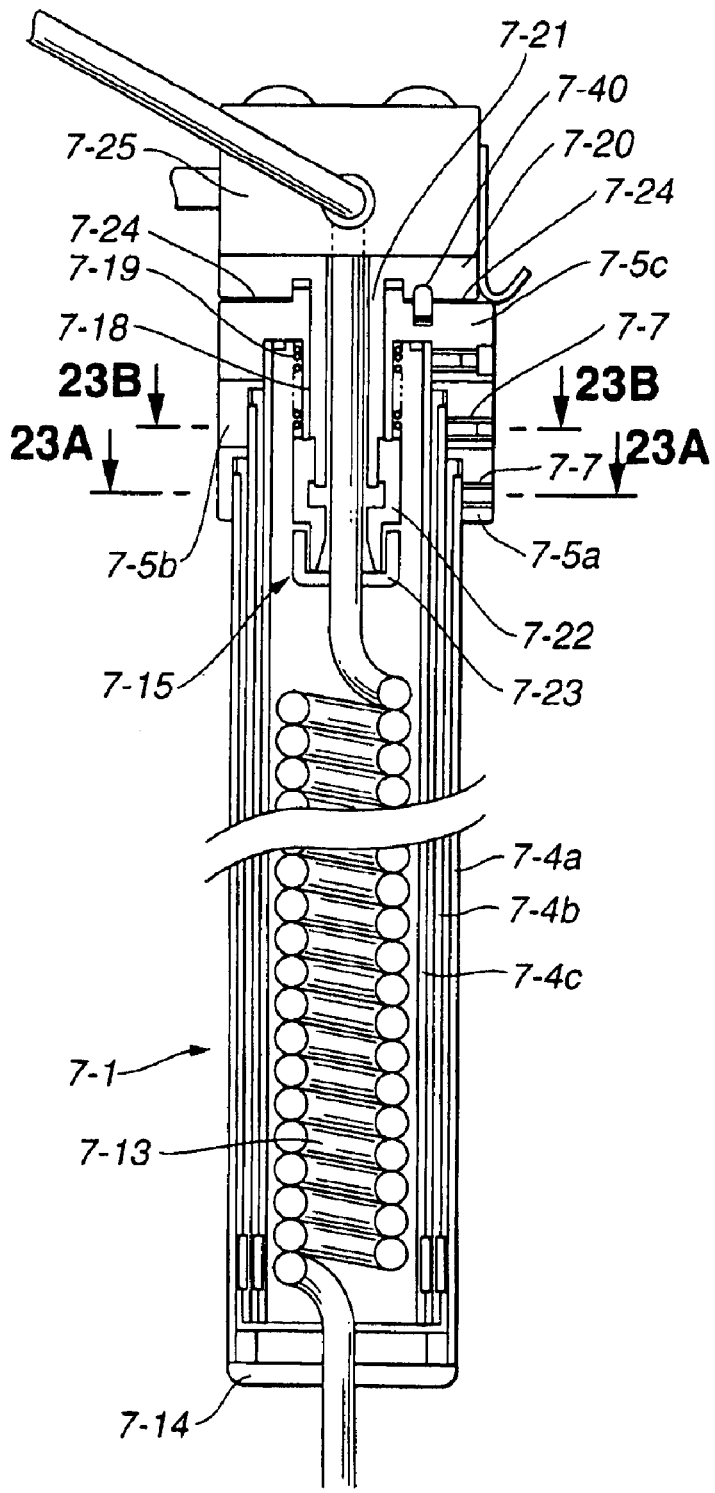
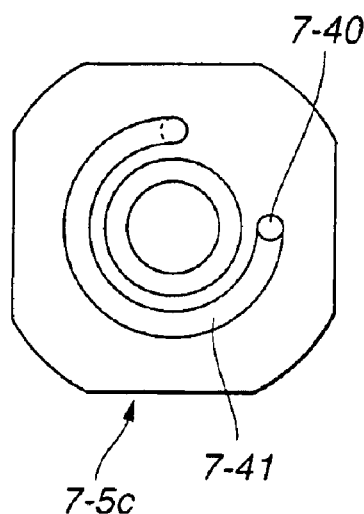
FIG.22A
FIG.22B

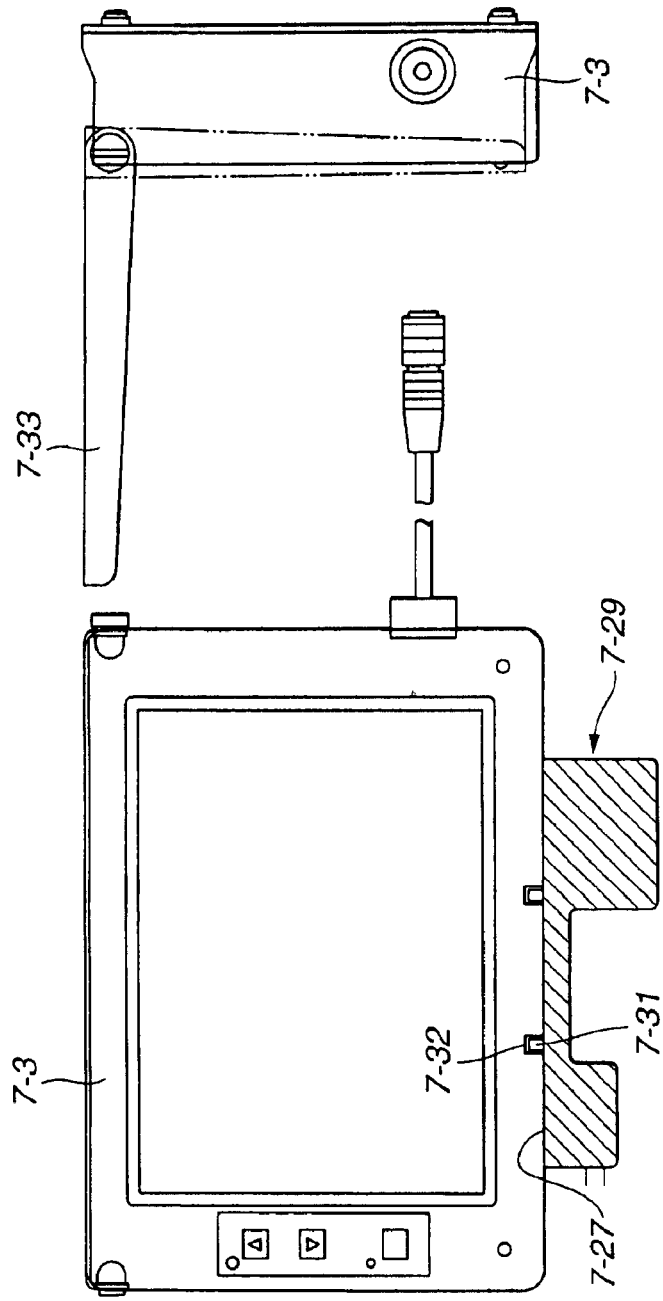
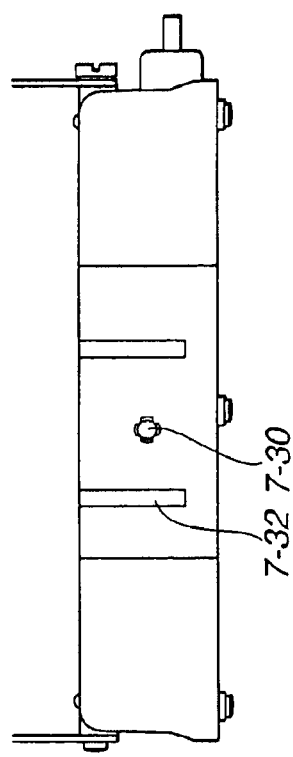
FIG.24A  FIG.24B  FIG.24C

| NUMBER OF DRUM ROTATIONS | OUTPUT OF VARIABLE RESISTOR (V) | DIGITIZED DATA (DECIMAL NOTATION) |
|---|---|---|
| 0 (FULLY DRAWN OUT) | 0~0.2 | 0~14 |
| 1 | 0.3~0.5 | 15~30 |
| 2 | 0.6~0.8 | 31~45 |
| 3 | 0.9~1.1 | 46~60 |
| 4 (3.5m WOUND UP) | 1.2~1.4 | 61~76 |
| 5 | 1.5~1.7 | 77~91 |
| 6 | 1.8~2.0 | 92~106 |
| 7 | 2.1~2.3 | 107~121 |
| 8 | 2.4~2.6 | 122~137 |
| 9 | 2.7~2.9 | 138~152 |
| 10 (9.5m WOUND UP) | 3.0~3.2 | 153~167 |
|  |  |  |
| (16.7) | 5.0 | 255 |

FIG.30

THRESHOLD ENABLING OR DISABLING ANGLE CONTROLLING

|  | RANGE OF DIGITAL DATA LEADING TO JUDGMENT THAT ANGLE CONTROLLING IS DISABLED (NO MOVEMENT CAN BE INSTRUCTED USING JOYSTICK INCLUDED IN REMOTE CONTROLLER OR EXTERNAL PC) | RANGE OF DIGITAL DATA LEADING TO JUDGMENT THAT ANGLE CONTROLLING IS ENABLED (MOVEMENT CAN BE INSTRUCTED USING JOYSTICK INCLUDED IN REMOTE CONTROLLER OR EXTERNAL PC) |
|---|---|---|
| TYPE 3.5m | 54~255 | 0~53 |
| TYPE 9.5m | 61~255 | 0~60 |

FIG.33

THRESHOLD TO TURN ON OR OFF LIGHT SOUCE LAMP

|  | RANGE OF DIGITAL DATA LEADING TO JUDGMENT THAT LAMP SHOULD BE TURNED OFF (LAMP CANNOT BE TURNED ON OR OFF USING SWITCH OF REMOTE CONTROLLER) | RANGE OF DIGITAL DATA LEADING TO JUDGMENT THAT LAMP SHOULD BE AUTOMATICALLY TURNED ON WITH POWER SUPPLY TURNED ON (LAMP CAN BE TURNED ON OR OFF USING SWITCH OF REMOTE CONTROLLER) |
|---|---|---|
| TYPE 3.5m | 59~255 | 0~58 |
| TYPE 9.5m | 154~255 | 0~153 |

FIG.34A    FIG.34B

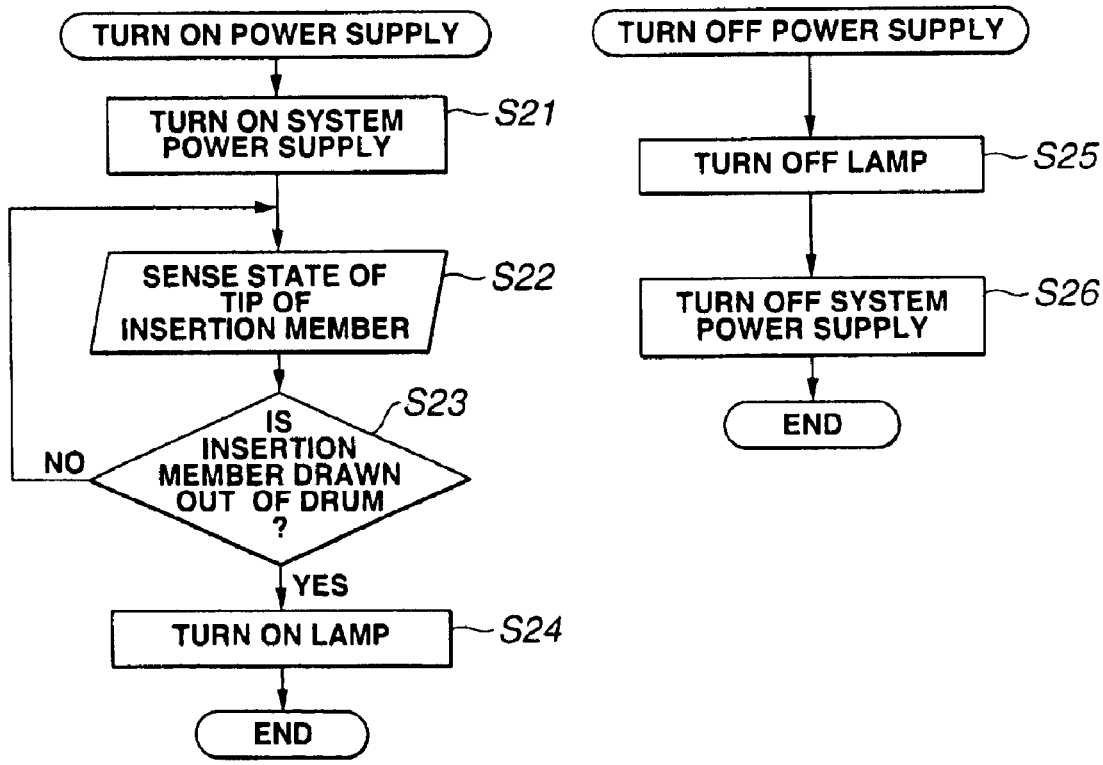

ROTATION DIRECTION

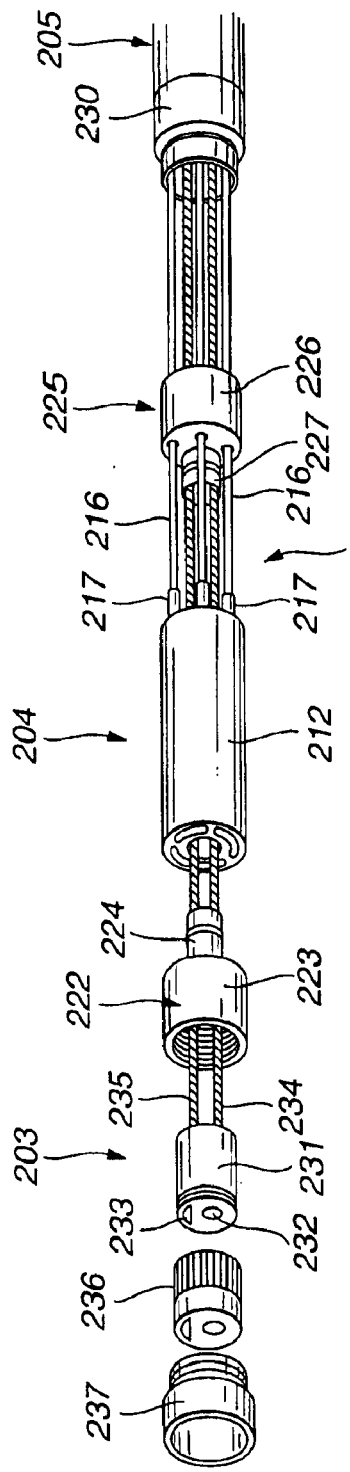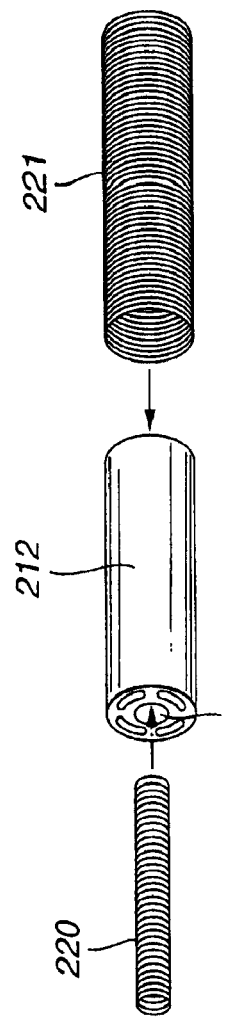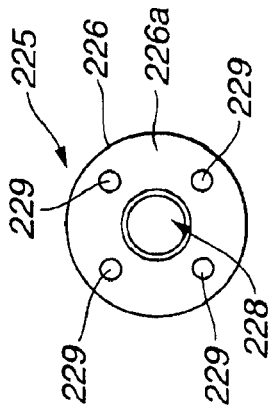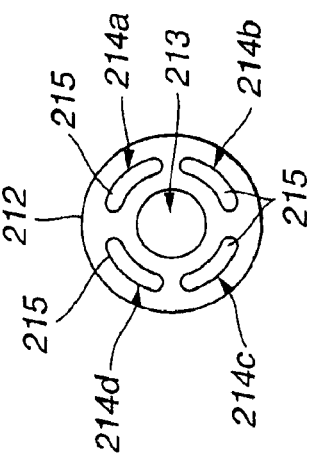

ENDOSCOPE APPARATUS WITH DRUM PART TO WIND INSERTION PART THEREAROUND

CROSS-REFERENCE TO RELATED APPLICATIONS

This is a continuation of U.S. patent application Ser. No. 09/808,807 filed on Mar. 15, 2001.

This application claims benefit of Japanese Application No. 2000-72816 filed in Japan on Mar. 15, 2000, No. 200072814 filed in Japan on Mar. 15, 2000, No. 2000-72815 filed in Japan on Mar. 15, 2000, No. 2001-5568 filed in Japan on Jan. 12, 2001, No. 2001-5567 filed in Japan on Jan. 12, 2001, Hei10-261767 filed in Japan on Sep. 16, 1998, the contents of which are incorporated these references.

BACKGROUND OF THE INVENTION

1. Field of the Invention

The present invention relates to an endoscope system having a drum, about which an insertion member of an endoscope is wound, stowed in a case.

2. Related Art Statement

An endoscope system having an insertion member elongated to be so long as to enable endoscopic inspection of a deep part of a plant is sometimes used as an endoscope system for industrial. In this case, if the elongated insertion member is left as it is, the endoscope system is no user-friendly. A drum-inclusive endoscope system is therefore sometimes employed, wherein the elongated insertion member is wound about a drum with its portion of a required length made usable.

For example, Japanese Laid-open Utility Model Publication No. 58-172905 discloses a container for endoscopes in which a scope stowage drum is encased in a carrier case. The container accommodates an endoscope alone, but does not accommodate the other system-related equipment.

Moreover, Japanese Laid-open Patent Application Publication No. 1-204014 discloses an endoscope system having a rubbertuator drive unit, a CCU, and a light source incorporated in a drum. The drum included in the endoscope system is left bared. No consideration is taken into transportability of the system.

There is therefore a demand for an endoscope system that is taken account at least of the transportability of the system. Japanese Patent Publication No. 5-56486 discloses an endoscope unit system in which a drum and a camera control unit (hereinafter CCU) are incorporated in a main unit in efforts to improve the ease of carrying or stowing an endoscope and the maneuverability of the endoscope such as the smoothness in inserting the endoscope. The CCU includes a signal processor for processing an image signal sent from a solid-state imaging device to produce a video signal. However, in the system, the endoscope does not have an angle controlling mechanism.

Moreover, Japanese Laid-open Patent Publication No. 4-81711 discloses an endoscope system, which includes an operator unit, an stowage unit, and a control unit, in efforts to realize a compact design and an ease of manipulation and to improve the maneuverability of the endoscope. The operator unit is used to set an angle of bending of a bending section. A flexible tube including the bending section is taken up and stowed in the stowage unit. The control unit is included in the stowage unit, and controls a fluid pressure to be applied to the bending section according to a set value from the operator unit. In the endoscope system, each equipment and a drum are separated from each other. The entire system including the drum is integrated into a case.

Furthermore, U.S. Pat. No. 5,323,899 discloses a video probe case in which an entire system is stowed in the form of one package. An endoscope integrated with a CCU and a light source are stowed mutually separately in the case.

German Patent No. DE19748795 discloses an endoscope system including a drum, an angle controlling mechanism, a CCU, and a light source.

However, in the endoscope unit system disclosed in the Japanese Laid-open Patent Publication No. 5-56486, the drum, light source, and CCU are integrated into the main unit. This leads to greatly improved maneuverability. However, when an insertion member is wound up, since the drum is bared, various operator buttons provided on the endoscope are exposed. Moreover, the entire system suffers from poor transportability. Moreover, there is difficulty in improving the resistance to shocks or to an environment.

Moreover, in the endoscope system disclosed in the Japanese Laid-open Patent Application Publication No. 4-81711, respective equipments are independently stowed in different cases. An unnecessarily large space is therefore occupied for stowage. The respective equipments cannot be stowed compactly. Moreover, it is time-consuming to lead numerous signal lines and a light guide fiber, which run through the insertion member of the endoscope, to the respective equipments by way of the drum. The structure of the drum is complex.

Moreover, according to the U.S. Pat. No. 5,323,899, respective equipments are independently stowed in the video probe case respectively. The use efficiently of a space is so poor that the case is very large. Besides, when an endoscope is used, a large heavy operator unit with an incorporated-in motor-driven angle controlling mechanism must be taken out from the case. The maneuverability is therefore poor. Furthermore, the endoscope is stowed alone. The video probe case is not of a drum-inclusive type.

Moreover, according to the German Patent No. DE19748795, the endoscope system is designed in consideration of a capacity for stowing an insertion member. However, the drum about which the insertion member is wound up is left bared. Various operator buttons provided on the endoscope are left exposed. No consideration is taken into a capacity for stowing a controller and other members to be stowed. This poses the same problem as the problem underlying the endoscope unit system disclosed in the Japanese Laid-open Patent Publication No. 5-56486.

Moreover, according to, for example, Japanese Unexamined Patent Application Publication No. 1-138522 and Japanese Examined Utility Model Publication No. 4-35850, a bearing means for rotatably bearing a drum freely is mounted on a shaft whose center coincides with the center of rotation of the drum.

However, when a rotational bearing structure is adopted, since a rotational bearing penetrates through the drum along the rotation center shaft of the drum, the presence of the rotational bearing affects the layout of respective equipments to be stowed in the drum. This results in an increase in the size of the drum.

Moreover, when the rotational bearing is formed on the outer circumference of the rotation center shaft of the drum, a signal line splicing structure or the like including a slip ring is needed to electrically connect equipment stowed in the drum to external equipment. The inclusion of the structure and the rotational bearing structure makes the structure of the drum complex and increases the size of the drum.

Conventionally, a method of checking an index line inscribed on an insertion member has been employed as a means for sensing by what length the insertion member is wound about an insertion member take-up drum or for sensing by what length the insertion member is extended from the drum.

In this case, there is a drawback that even when an attempt is made to control various relevant equipments according to the length by which the insertion member is wound about the drum, information of the length cannot be automatically supplied to the equipments.

In contrast, according to Japanese Laid-open Patent Publication No. 10-274743, a length of movement by which an insertion member (referred to as a coil spring in the publication) is drawn out is detected by counting the number of pulses output from rotary encoders coupled to the rotation shafts of a pair of rollers that sandwiches the insertion member.

According to the above publication, the information of the length by which the insertion member is drawn out can be outputted electrically. However, part of the detecting means is mechanically driven. The number of pulses generated from the rotary encoders is counted for electrically detecting the length of movement. Therefore, only when the power supply is turned on, the length is measured and the information of the length is outputted. Whenever the power supply is turned on, the insertion member must be initialized to the same state. Otherwise, length information cannot be acquired accurately.

Moreover, when the power supply is temporarily turned off during use, the length by which the insertion member is drawn out cannot be measured during the period during which the power supply is off. There is therefore a fear that a value measured with the power supply turned on may be inaccurate. For preventing this incident, when the power supply is turned off, the length by which the insertion member is drawn out must be held unchanged carefully. This is no user-friendly.

Moreover, in the drum-inclusive endoscope system, the insertion member is exposed to outside. This is inconvenient for transporting the endoscope system. Moreover, from the structural viewpoint, it is hard to protect the endoscope system from shocks during transportation. Japanese Laid-open Patent Publication No. 2000-89131 discloses an endoscope system structured to protect components with a housing.

For protecting the contents of the housing from shocks, it is conceivable to interpose shock absorbers between the surfaces of the housing that may undergo the shocks and the contents thereof, though the shock absorbers are not included in the endoscope system described in the Japanese Laid-open Patent Publication No. 2000-89131. However, when the shock absorbers are placed on the surfaces that may undergo shocks, the housing must be made larger by dimensions required for the inclusion of the shock absorbers. When the housing is confined to the smallest possible size and the number of shock absorbers is made smaller than a required number of shock absorbers, the contents of the housing may be broken due to shocks.

OBJECTS AND SUMMARY OF THE INVENTION

Accordingly, an object of the present invention is to provide an endoscope system that has an excellent capacity for stowing an insertion member of an electronic endoscope, and that is so compact as to enjoy improved transportability with the insertion member stowed. The insertion member includes a bending section that is motor-driven to bend.

Another object of the present invention is to provide an endoscope system that enjoys a simple structure, and capable of supporting a drum rotatably, which can be designed compactly.

Another object of the present invention is to provide an endoscope system which enjoys improved user-friendliness and in which a length by which an insertion member is wound about a drum can be measured without the necessity of a power supply, and can be electrically outputted if required.

Still another object of the present invention is to provide an endoscope system having a compact housing and including shock absorbers with which the contents of the housing can be protected from shocks.

Briefly, according to the present invention, there is provided an endoscope system having an insertion member wound about a drum, which comprises an electronic endoscope having a solid-state imaging element incorporated at a tip of an insertion member, a bending section included in the insertion member being motor-driven to bend;

a drum having the insertion member wound about the outer circumference thereof;

an angling input unit at which an operator enters a direction of bending in which the bending section bends, and which is separated from the electronic endoscope;

a motor-driven angling unit incorporated in the drum and including a driving source for driving a driving mechanism that drives the bending section;

a camera control unit that controls the solid-state imaging element and includes a signal processor for processing an electric signal sent from the solid-state imaging element to produce a video signal;

a motor-driven angling control circuit unit for controlling the movement of the bending section; and a stowage case in which the drum is rotatably stowed freely. Consequently, the endoscope system can be easily preserved and transported.

The above and many other objects, features, and advantages of this invention will become apparent from the ensuing detailed description of one preferred embodiment, which should be read in conjunction with the accompanying drawing.

BRIEF DESCRIPTION OF THE DRAWING

FIG. 1 to FIG. 26 are explanatory diagrams concerning a first embodiment of the present invention;

FIG. 1 is an explanatory diagram showing the overall configuration of a drum-inclusive endoscope system;

FIG. 2 shows the structure of the tip of an insertion member of an endoscope for industrial use;

FIG. 3A is a left side view of a case;

FIG. 3B is a front view of the case;

FIG. 3C is a plan view of the case;

FIG. 4 is a sectional view showing the interior of the case;

FIG. 6 shows one surface of the case on which a handle is mounted;

FIG. 9A shows a front panel with a lid left open;

FIG. 9B shows an ac cable plugged in to an ac receptacle;

FIG. 9C shows a dc cable plugged in to a dc receptacle;

FIG. 9D is a 9D—9D sectional view of the front panel shown in FIG. 9A;

FIG. 11 shows the structures of a first exhaust vent and an intake cylinder;

FIG. 14 shows the interior of the case seen from the back surface thereof;

FIG. 18 shows the interior of the drum exposed in an opening with a first drum cover removed;

FIG. 19 is a side view of the drum about which the insertion member is wound;

FIG. 20A shows an operator lever and its surroundings on the front panel;

FIG. 20B is an explanatory diagram showing a moving plate and its surroundings with a second side panel set to be rotatable in only one direction using a one-way gear responsively to a manipulation performed on the operator lever;

FIG. 20C is an explanatory diagram showing the moving plate and its surroundings with the second panel freed;

FIG. 20D shows a presser pin seen in a direction of arrow G indicated in FIG. 20B;

FIG. 20E shows the presser pin seen in a direction of arrow G indicated in FIG. 20C;

FIG. 22A is an explanatory diagram showing the structure of the stretchable pole;

FIG. 22B is a top view of a third cover;

FIG. 24A is a front view of a liquid crystal monitor;

FIG. 24B is a bottom view of the liquid crystal monitor;

FIG. 24C is a side view of the liquid crystal monitor having a light interceptor panel attached thereto;

FIG. 25 is a sectional view of a drum including a side view of a monitor unit;

FIG. 26 shows a structure seen in a direction of arrow A indicated in FIG. 25;

FIG. 27 to FIG. 32 are explanatory diagrams concerning an electric system employed in the first embodiment;

FIG. 28 is a block diagram showing a system control CPU that detects an output of a sliding variable resistor;

FIG. 29 is a table listing an output voltage developed at an output terminal of the sliding variable resistor and digitized data which vary depending on the number of turns by which the insertion member is wound about a drum;

FIG. 30 lists practical values of a threshold based on which angle controlling is enabled or disabled;

FIG. 31 is a flowchart describing actions to be performed in the present embodiment;

FIG. 32 is a flowchart describing actions to be performed in a variant;

FIG. 33, FIGS. 34A and 34B are explanatory diagrams concerning a second embodiment;

FIG. 33 lists practical values of a threshold based on which a light source lamp is turned on or off;

FIG. 34A is a flowchart describing actions to be performed when a power switch is turned on;

FIG. 34B is a flowchart describing actions to be performed when the power switch is turned off;

FIG. 36 shows the structures of a cable stowage and its surroundings employed in the seventh embodiment;

FIG. 37 shows the structure of a cable fixture;

FIG. 39 to FIGS. 43A and 43B are explanatory diagrams concerning a ninth embodiment of the present invention;

FIG. 39 schematically shows the appearance of the ninth embodiment;

FIG. 40 is a longitudinal sectional view showing the structure of a rotationally driving mechanism;

FIG. 41 shows part H of FIG. 40 in enlargement;

FIG. 42 shows a drum that holds the proximal part of an insertion member;

FIG. 43A is an explanatory diagram concerning an operation of a one-way clutch exerted when a housing is turned clockwise;

FIG. 43B is an explanatory diagram concerning an operation of the one-way clutch exerted when the housing is turned counterclockwise;

FIG. 44 to FIGS. 47A and 47B are explanatory diagrams concerning a tenth embodiment of the present invention;

FIG. 44 is a longitudinal sectional view showing a rotationally driving mechanism employed in the tenth embodiment of the present invention;

FIG. 45 is an enlarged view of part of the rotationally driving mechanism;

FIG. 46 is a 46—46 sectional view of the part shown in FIG. 45;

FIG. 47A is an enlarged view of part J of FIG. 46 for explaining an operation of an one-way clutch exerted when the one-way clutch is engaged with a shaft;

FIG. 47B is an enlarged view of the part J of FIG. 46 for explaining an operation of the one-way clutch exerted when the one-way clutch is not engaged with the shaft;

FIG. 48 to FIGS. 50A and 50B are explanatory diagrams concerning an eleventh embodiment of the present invention;

FIG. 48 shows the structures of the center of a rotationally driving mechanism and its surroundings employed in the eleventh embodiment of the present invention;

FIG. 49 is a 49—49 sectional view of the structures shown in FIG. 48;

FIG. 50A is an explanatory diagram concerning a movement to be made with a claw engaged with a sprocket;

FIG. 50B is an explanatory diagram concerning a movement to be made with the claw disengaged from the sprocket;

FIG. 51 shows the structure of a rotation restricting mechanism located near the periphery of a drum employed in the twelfth embodiment of the present invention;

FIG. 52 is a side view of the structure viewed in a direction of L indicated in FIG. 51;

FIG. 53 to FIG. 58 are explanatory diagrams concerning a thirteenth embodiment of the present invention;

FIG. 53 shows the appearance of an endoscope system including an endoscope of a pneumatic angling type;

FIG. 54A is an exploded perspective view of an insertion member;

FIG. 54B is an explanatory diagram showing the relationship between a multi-lumen tube and a deformation restricting member;

FIG. 54C is a sectional view of the multi-lumen tube;

FIG. 54D is a sectional view of a cylindrical part of a rear cap;

FIG. 55 shows the structure of a drum;

FIG. 56 shows the structure of a bending section drive unit;

FIG. 57 is an explanatory diagram concerning the details of a bending section driving mechanism;

FIG. 58 shows movements made in the bending section driving mechanism;

FIG. 59 shows the appearance of an endoscope system including an endoscope of a hydraulic angling type;

FIG. 60 is a sectional view for explaining the structure of the tip of an insertion member;

FIG. 61 shows the structure of a drum;

FIG. 62 shows the structure of a bending section drive unit;

FIG. 63 is an explanatory diagram concerning the details of a bending section driving mechanism; and FIG. 64 shows movements made in the bending section driving mechanism.

DETAILED DESCRIPTION OF THE PREFERRED EMBODIMENT

Embodiments of the present invention will be described with reference to the drawings below.

(First Embodiment)

A first embodiment of the present invention will be described with reference to FIG. 1 to FIG. 24.

Figure 1:
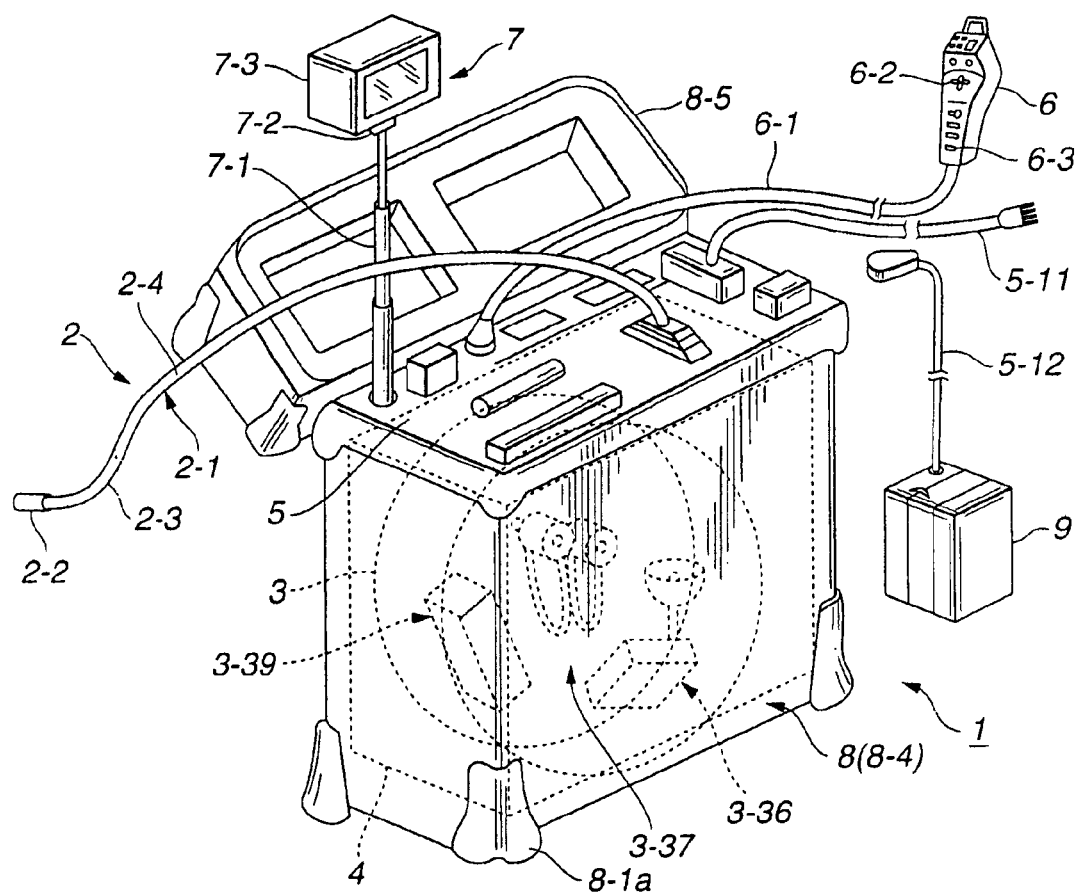

As shown in FIG. 1, a drum-inclusive endoscope system 1 for industrial use in accordance with the first embodiment of the present invention consists mainly of an endoscope 2 for industrial use, a drum 3, a frame 4, a front panel 5, a remote controller 6, a liquid-crystal monitor unit 7, and a stowage case (hereinafter case) 8. Various switches and connectors, and an exhaust vent and an intake vent are exposed on the front panel 5.

The industrial endoscope 2 has an elongated insertion member 2-1 that is flexible. The drum 3 has a cylindrical shape, and the elongated insertion member 2-1 is wound about the periphery (outer circumference) of the drum 3. The frame 4 rotatably holds the drum 3 freely. The front panel 5 is placed on the top of the frame 4. The remote controller 6 is connected to the front panel 5 by way of a cable 6-1. The liquid crystal monitor unit 7 includes a stretchable pole 7-1, a rotating mechanism 7-2, and a liquid crystal monitor 7-3. Shock absorbers 8-1a for suppressing shocks applied to equipment stowed in the case 8 are attached to the case 8. Mains voltage can be applied over an ac cable 5-11 led to the front panel 5. Dc voltage can be applied from a battery 9 over a dc cable 5-12.

A light source unit 3-36, a CCU 3-39, and a motor included in a motor-driven angling unit 3-37 are stowed in the drum 3. The light source unit 3-36 supplies illumination light over a light guide that serves as an illumination light propagating means included in the industrial endoscope 2. The CCU 3-39 processes a signal produced by an imaging device incorporated in the tip rigid part 2-2 of the insertion member 2-1 of the industrial endoscope 2. The motor-driven angling unit 3-37 drives the bending section 2-3 of the insertion member 2-1a to bend the bending section 2-3.

The insertion member 2-1 has the tip rigid part 2-2, the bending section 2-3, and a flexible tube 2-4 concatenated in that order from the tip thereof. The digital rigid part 2-2 is hard. The bending section 2-3 can bend freely to angle the tip rigid part 202 in a desired direction. The flexible tube 2-4 is elongated and soft.

Figure 17A:
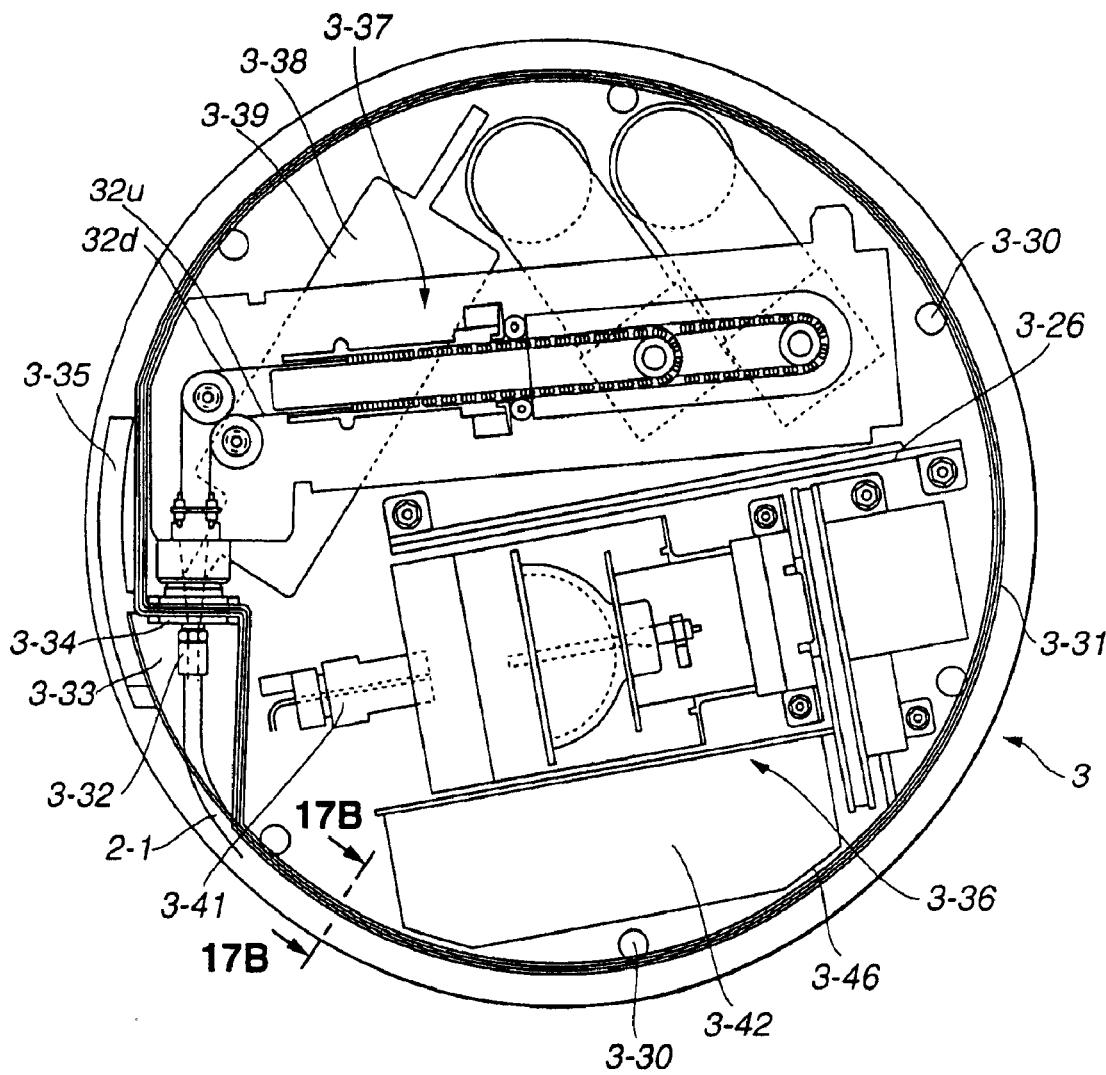
FIG. 17A is an explanatory diagram showing the interior of the drum seen from the surface thereof on which the handle is mounted.

As shown in FIG. 2, a light guide 21 over which illumination light is propagated runs through the insertion member 2-1. A light guide connector 3-41 is, as shown in FIG. 17A, attached to the back end of the light guide 21. The light guide connector 3-41 is fixed to the light source unit 3-36. Illumination light supplied from the light source unit 3-36 is propagated over the light guide 21, and emitted forwards through an illumination lens 23 that is locked in a tip member 22 included in the tip rigid part 202 and that forms an illumination window. Consequently, an object in a plant is illuminated.

An objective optical system 24 forming an observation window adjacent to the illumination window is also mounted in the tip rigid part 2-2. A solid-state imaging device (solid-state imaging element), for example, a charge coupled device (hereinafter CCD) is located at the position of the image plane of the objective optical system 24. A signal line 26 extending from the CCD 25 is led to the CCU 3-39 in the drum 3. The CCU 3-39 produces a standard video signal from an electric signal that results from photoelectric conversion performed by the CCD 25, and transfers the video signal to the liquid crystal monitor 7-3 included in the liquid crystal monitor unit 7. An object image is then displayed on the display screen of the monitor.

The bending section 2-3 communicates with the back end of the tip rigid part 2-2. The bending section 2-3 rotatably has a plurality of annular joint pieces 27 concatenated using rivets 28 freely. The plurality of joint pieces 27 that are concatenated to be freely rotatable is covered with a rubber tube 29. The periphery of the rubber tube 29 is sheathed with a protective armor 30 over the whole length of the insertion member 2-1. The armor 30 is a metallic braid.

Pipe-like wire bearers 31 are secured to meet upper, lower, right, and left points on the inner surface of each joint piece 27. Angulation wires 32*u*, 32*d*, 32*l*, and 32*r* used to bend the bending section are passed through the holes of the wire bearers 31 so that the angulation wires can slide freely. FIG. 2 shows only the angulation wires 32*u* and 32*d* passed through the upper wire bearers.

The tip parts of the angulation wires 32*u*, 32*d*, 32*l*, and 32*r* are fastened to upper, lower, right, and left points on the rear part of the tip member 22. By pulling any two of the angulation wires 32*u*, 32*d*, 32*l*, and 32*r* that cause the bending section to bend in a vertical or lateral direction, the bending section 2-3 is bent in a desired direction. Consequently, the tip rigid part 2-3 is angled in the desired direction.

The back ends of the angulation wires 32*u*, 32*d*, 32*l*, and 32*r* are, as shown in FIG. 17A, led to the motor-driven angling unit 3-37. By tilting a joystick 6-2 included in the remote controller (hereinafter simply a controller) 6, the rotation of the motor included in the motor-driven angling unit 3-37 is controlled and the bending section 2-3 is bent in the same direction as a direction in which the joystick 6-2 is tilted.

For constructing the bending section 2-3, the number of joint pieces 27 is increased or decreased based on a desired maximum angle of bending. In short, the number of joint pieces 27 is not limited to the number of joint pieces shown in FIG. 2.

Coil pipes 33*u*, 33*d*, 33*l*, and 33*r* are enclosed in the elongated flexible tube 2-4 communicating with the bending section 2-3. The angulation wires 32*u*, 32*d*, 32*l*, and 32*r* run through the coil pipes 33*u*, 33*d*, 33*l*, and 33*r* so that they can slide. The coil pipes 33*u*, 33*d*, 33*l*, and 33*r* are integrated with the tip of the flexible tube 204 by performing, for example, brazing. FIG. 2 shows only the coil piles 33*u* and 33*d* located at upper points on the inner surface of the flexible tube.

The coil pipes 33*u*, 33*d*, 33*l*, and 33*r* and the angulation wires 32*u*, 32*d*, 32*l*, and 32*r* are passed through the flexible tube 2-4 and extended to the motor-driven angling unit 3-37.

The industrial endoscope 2 is an electronic endoscope with a built-in imaging device. The signal line 26 and light guide 21 are passed through the insertion member 2-1. Various optical adaptors for changing a viewing direction and an angle of view can be attached to the tip rigid part 2-2.

The structure of the case 8 will be described with reference mainly to FIGS. 3A to 3C to FIGS. 5A and 5B.

As shown in FIG. 3A, FIG. 3B, and FIG. 3C, the upper part of the case 8 opens. The case 8 consists mainly of a case body 8-4, a lid 8-5, shock absorbers 8-1*a*, and shock absorbers 8-1*b*. The lid 8-5 can be opened or closed to enable or disable access to the interior of the case body 84. The shock absorbers 8-1*a* are made of a rubber and fixed to the outer surfaces of the case body 8-4 and lid 8-5 in order to absorb shock force that is applied when the case is dropped or the like. The shock absorbers 8-1*b* are, as shown in FIG. 4, fixed to the inner surfaces of the case body in order to absorb shock force.

The case body 8-4 consists of a first case body 8-2 and a second case body 8-3 that are parted from each other forwards and backwards respectively when the case body 8-4 is seen from the front side thereof as shown in FIG. 3B. A holded portion 8-6 is formed on the top of the lid 8-5.

The case body 8-4 is made by joining the first case body 8-2 and second case body 8-3 with the bottoms and side surfaces thereof integrated with each other using screws 34. Since the case body 8-4 consists of two case bodies, the efficiency in assembling has improved.

A thick part 8-7 is formed as the part of the case body 8-4 engaged with the lid 8-5. Hinges 8-8 are attached to the back surface of the thick part 807, and buckles 809 are attached to the front surface thereof. The lid 8-5 can be freely opened or closed to meet or part from the case body 8-4.

The case body 8-4 and lid 8-5 are made of a resin, or more particularly, molded or die-cast using a resin.

Figure 5A:
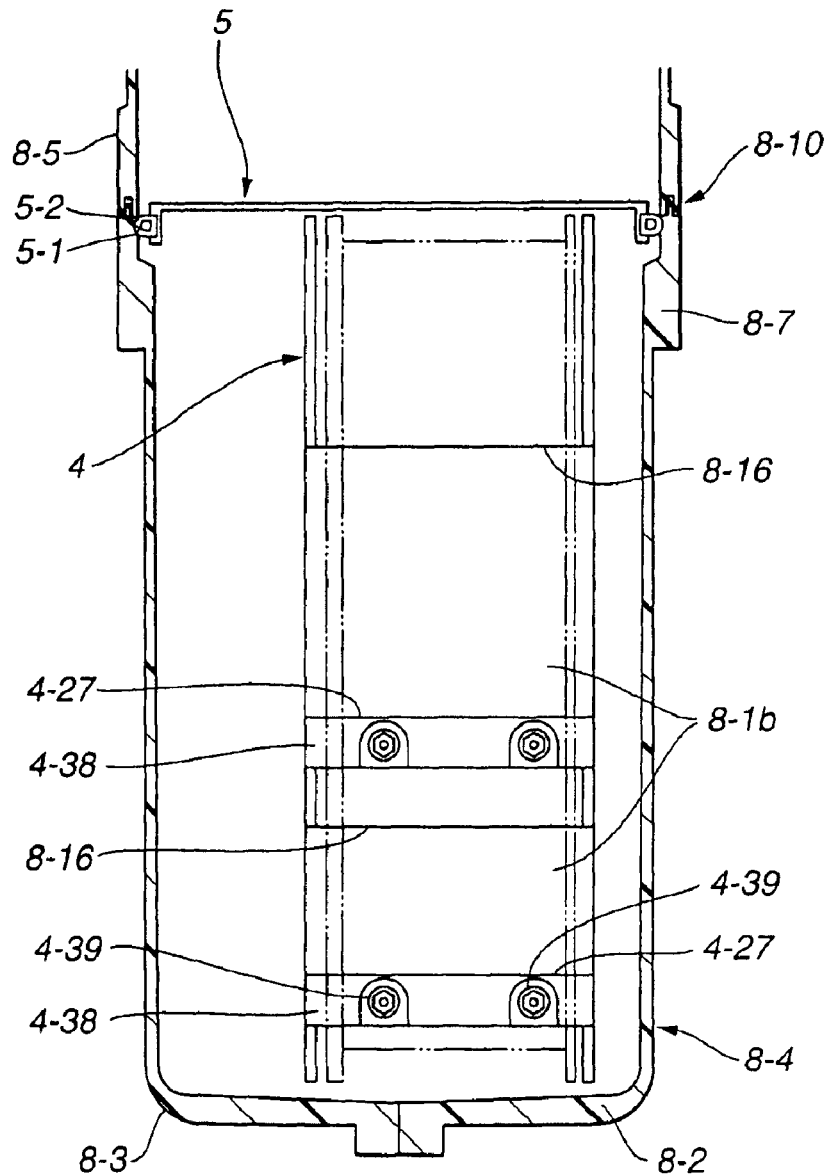
FIG. 5A shows a cutting plane A of the interior of the case shown in FIG. 4.
Figure 5B:
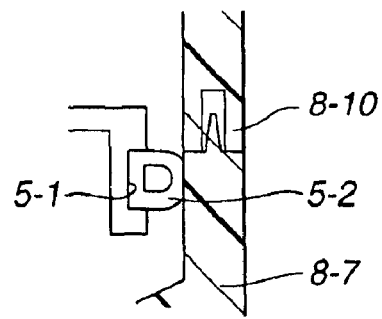
FIG. 5B is an enlarged view showing concave and convex parts shown in FIG. 5A.

As shown in FIG. 5A, a convex part 8-10 is formed over the top of the thick part 8-7 that comes in contact with the lid. As shown in FIG. 5B, when the lid 8-5 is closed, the convex part 8-10 is engaged with a concave part of the lid 8-5. Consequently, the lid 8-5 is closed without a gap. Two female screws 8-11 are, as shown in FIG. 3A, threaded in the thick part 8-7. Therefore, a strap or the like can be, if necessary, screwed to the thick part 8-7.

As shown in FIGS. 3A and 3B, the rubber shock absorbers 8-1*a* for absorbing shocks to alleviate the influence of the shocks on the case 8 are attached to the corners of the case 8 and the four upper corners of the case body 8-4. In whatever posture the case 8 may be dropped to the ground, the shock absorbers 8-1*a* first come into contact with the ground.

The shock absorbers 8-1*a* have a shape effective in preventing shocks from being directly applied to the hinges 8-8, buckles 8-9, and the resin part of the case 8. In other words, the thickness of the hinges 8-8 is made smaller than the thickness of the shock absorbers 8-1*a*.

The shock absorbers 8-1*a* are attached to the upper corners of the case body 8-4. With the lid 8-5 left open, the case 8 can be carried by holding the shock absorbers 8-1*a*.

In the present embodiment, as shown in FIG. 4 and FIGS. 5A and 5B, the shock absorbers 1-*b* are placed on the inner surface of the case body 8-4 in order to protect the contents of the frame 4 put in the case body 8-4, which is a housing, from shocks.

For protecting the contents of the housing from shocks applied to the housing, such a structure may be adopted that shock absorbers are interposed between the side surfaces of the housing, which lie in the same direction as a direction in which shocks are applied, and the contents thereof. In this case, the housing must be designed to be long in the direction that is a vertical direction, and therefore become large in size. According to the present embodiment, therefore, the plurality of shock absorbers 8-1*b* is placed on the inner side surfaces of the case body 8-4 as described below. This is intended to protect the contents from shocks despite the compact design without the necessity of making the case vertically long.

As shown in FIG. 1, the front panel 5 is placed on the top of the frame 4. Precision electric equipment including the liquid crystal monitor 7-3 is stowed in a space created between the front panel 5 and the lid 8-5 to be closed to meet the front panel 5. Therefore, the case must be protected especially from shocks applied vertically.

Moreover, precision electric equipment including the light source unit 3-36 and CCU 3-39 is rotatably stowed in the drum 3 held in the frame 4 freely.

Furthermore, when the lid 8-5 is opened in order to join or disjoin connectors to or from connectors formed on the front panel 5, the face of the front panel should hopefully be exposed for easy manipulation.

In the present invention, therefore, no shock absorber is located near the front panel 5. Instead, the shock absorbers 8-16 are interposed between the inner surface of the case body 8-4 and the frame 4 opposed to the inner surface of the case body 8-4. Thus, the contents of the case including the liquid crystal monitor 7-3 and light source unit 3-36 are protected from shocks to be applied vertically.

Now, what are referred to as shocks are shocks including vibrations occurring mainly when the case 8 is transported with the lid 8-5 closed. In other words, the shocks refer to shocks applied to the case 8 with the case 8 left unpacked with packing materials.

The inner surface of the case body 8-4, that is, the inner surfaces of the first case body 8-2 and second case body 8-3 have receiving surfaces 8-16 formed vertically or perpendicularly. In contrast, the frame 4 has bearers 4-27 formed thereon so that the bearers 4-27 will be vertically separated from the receiving surfaces 8-16 and opposed to the receiving surfaces 8-16. The upper ends of the plate-like shock absorbers 8-1b are brought into contact with the receiving surfaces 8-16, and the lower ends thereof are brought into contact with the bearers 4-27. The side surfaces of the plate-like shock absorbers 8-1b are brought into contact with the inner surface of the case body 8-4 and the outer surface of the frame 4.

In other words, the receiving surfaces 8-16 are formed at right vertical positions on the inner surfaces of the first case body 8-2 and second case body 8-3. The shock absorbers 8-1b are arranged in the space created between the inner surfaces and the outer surface of the frame 4 so that the end surfaces of the shock absorbers will come into contact with the receiving surfaces 8-16. The bearers 4-27 are abutted on the other end surfaces of the shock absorbers 8-1b, and compressed and secured. Consequently, the frame 4 is elastically held in the case body 8-4 with the shock absorbers 8-1b between them. Bearer members 4-38 are fixed to the frame 4 using screws 4-39 shown in FIG. 5.

Consequently, the case becomes compact. Besides, if the case is vertically shocked, for example, if the case 8 is dropped with the lid 8-5 facing down, the shock absorbers 8-1b absorb shocks applied to the contents of the frame 4.

Next, the structure of a handle cover 3-1 having a handle 3-11, which is used to rotate the drum 3, fixed thereto will be described with reference to FIG. 6 to FIG. 7B. The structure of the handle 3-11 will be described with reference to FIG. 8.

Figure 6:
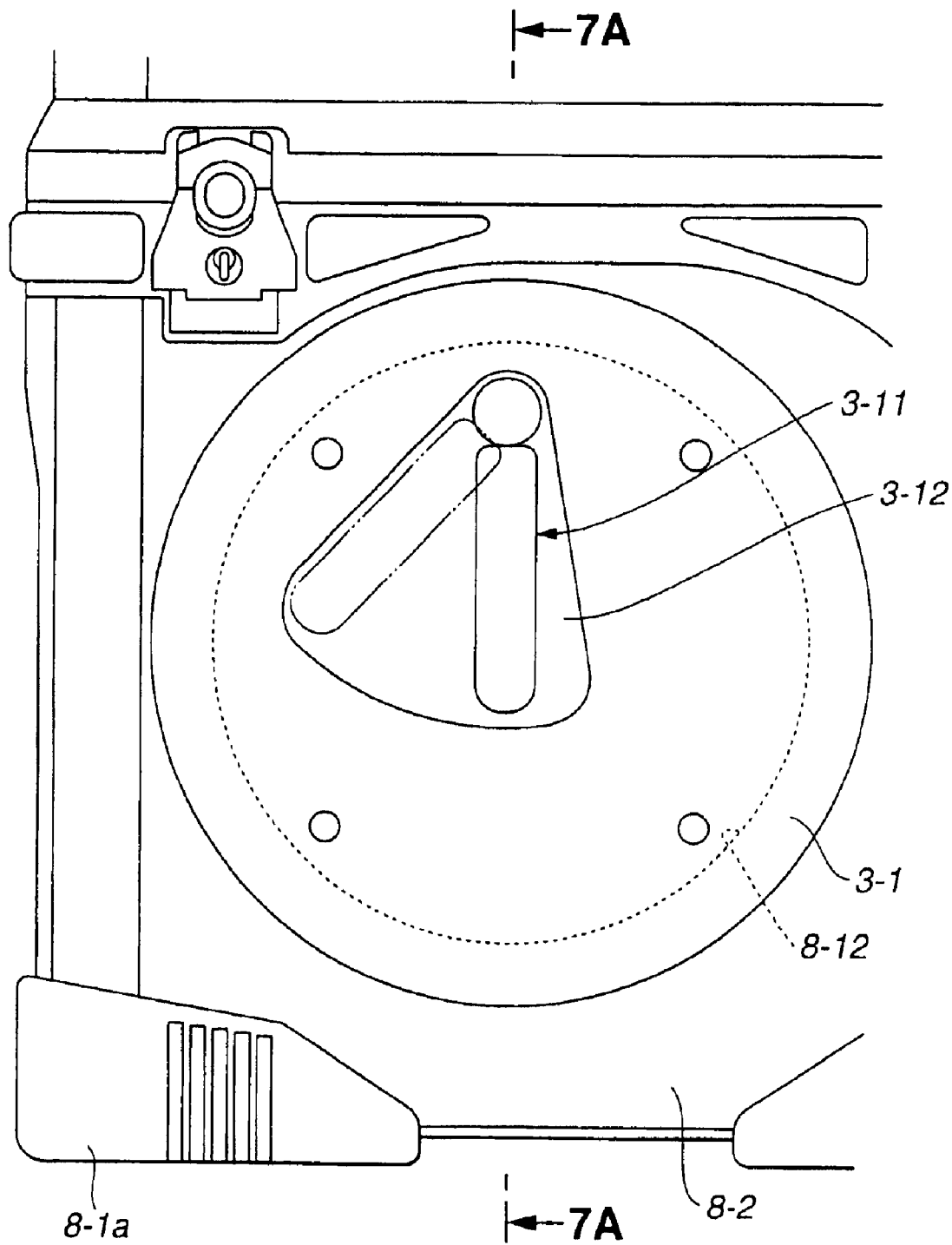
Figure 7A:
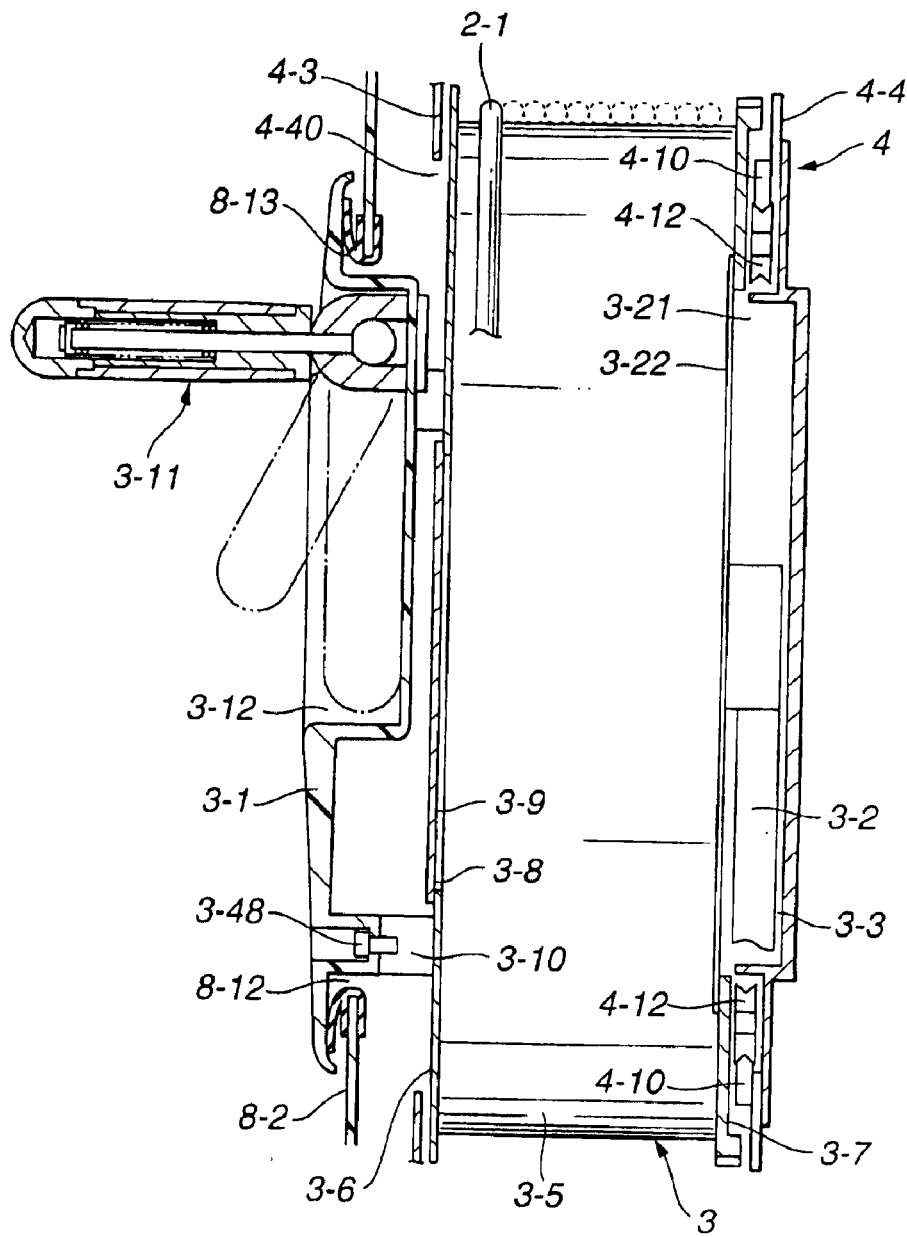
FIG. 7A is a 7A—7A sectional view of the case shown in FIG. 6.
Figure 7B:
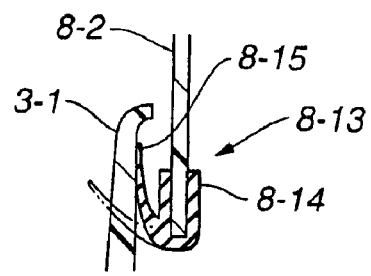
FIG. 7B is an enlarged view of a packing.

The first case body 8-2 has, as indicated with a dashed line in FIG. 6 and as shown in FIG. 7A, a round opening 8-12 formed therein. A rubber packing 8-13 is fixed to the perimeter of the opening 8-12.

The handle cover 3-1 having a substantially round shape and being larger than the opening 8-12 is fixed to the drum 3 located inside the opening 8-12 with the back surface of the handle cover 3-1 pressured to the drum 3. The back surface of the handle cover 301 is located inside the packing 8-13 fixed to the opening 8-12. Since the packing 8-13 is pressured by the handle cover 3-1, a gap between the packing and handle cover is sealed to rainproof and dustproof. The handle cover 3-1 is fixed to the drum 3 with a shock absorber 3-10 between them.

The packing 8-13 is made of an elastic material such as a rubber. The packing 8-13 is, as shown in FIG. 7B, composed of an attachment portion 8-14 whose cross section is shaped substantially like letter U and a fin portion 8-15 that comes into contact with the handle cover 3-1.

The fin portion 8-15 is shaped to project outwards as indicated with an alternate long and two short dashes line under normal conditions. When the handle cover 3-1 is mounted, the fin portion 8-15 is folded and pressured by the back surface of the handle cover 3-1 as indicated with a solid line. Consequently, the fin portion 8-15 is held pressured to ensure watertightness.

The cylindrical drum 3 is rotatably held between a first frame 4-3 and a second frame 4-4 freely. The first frame 4-3 and second frame 4-4 constitute the frame 4 and lie inside the handle cover 3-1. The insertion member 2-1 is wound about a cylindrical member 3-5 of the drum 3 and thus stowed.

The first frame 4-3 has a round opening 4-40 opposed to the round opening 8-12 of the first case body 8-2. A first side panel 3-6 and a second side panel 3-7 that block the openings of the cylindrical member 3-5 are located adjacently to the first frame 4-3 and second frame 4-4 inside the first frame 4-3 and second frame 4-4. The first side panel 3-6 and second side panel 3-7 have openings 3-8 and 3-21 respectively.

Figure 18:
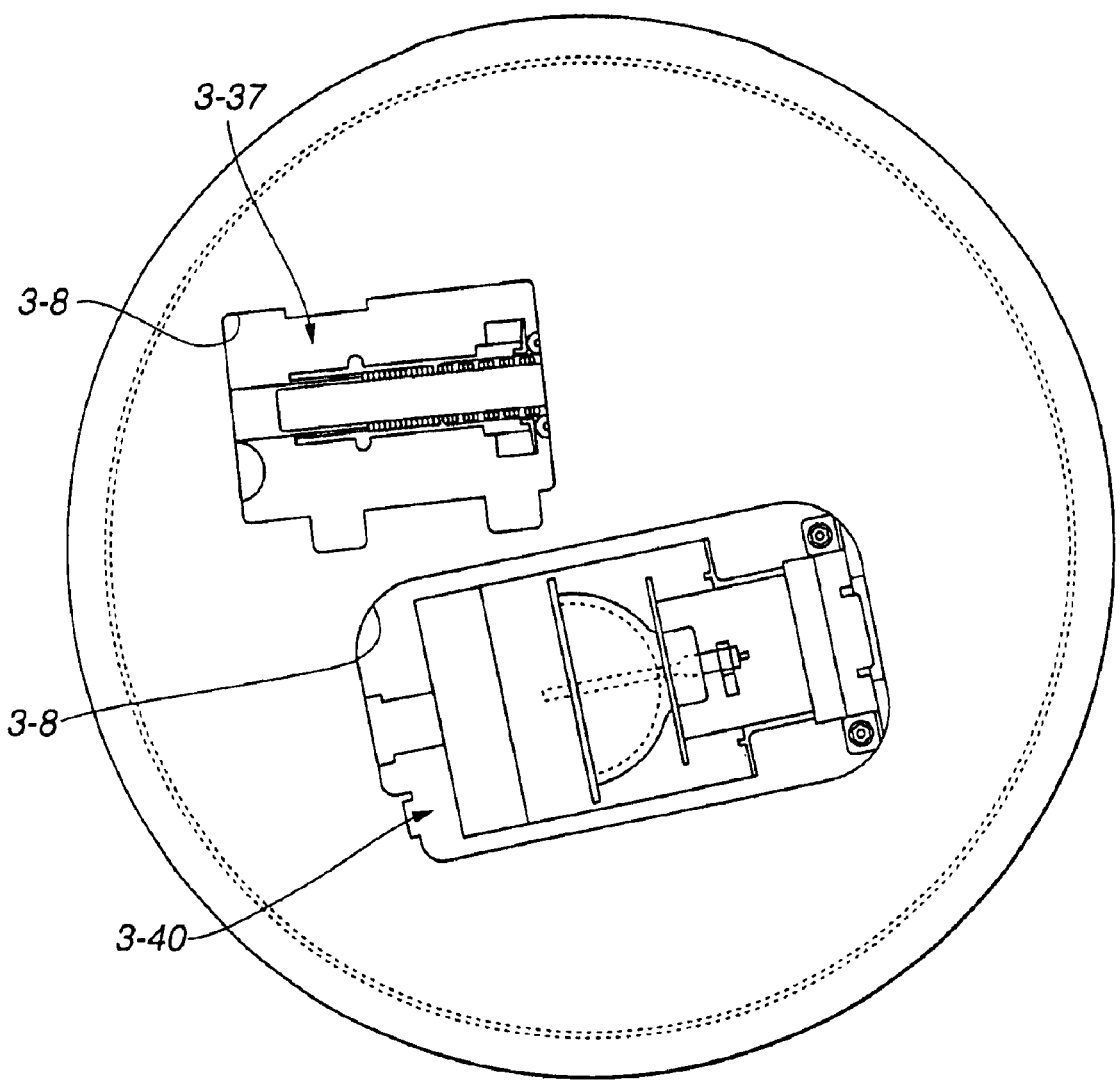

The openings 3-8 and 3-21 are blocked with a first drum cover 3-9 and a second drum cover 3-22 respectively. The opening 3-8 of the first side panel 3-6 actually includes two openings as shown in FIG. 18. The lamp unit 3-40 and an adjuster of a bending section driving mechanism included in the motor-driven angling unit 33 are exposed through the openings. This is intended to make it easy to replace a lamp with a new one or to adjust or repair the bending section driving mechanism.

Specifically, once the handle cover 3-1 is removed and the first drum cover 3-9 is then removed, a lamp can be easily replaced with a new one, an angle of bending can be adjusted easily, or a repair can be carried out easily. Moreover, the sag in the angulation wires 32u and 32d within the motor-driven angling unit 3-37 can be adjusted in order to correct an error in an angle of bending caused by the sag.

The handle cover 3-1 is fixed to the perimeter of the opening 3-8 of the first side panel 3-6 with shock absorbers 3-10 between them using a plurality of screws 3-48. The outer surface of the handle cover 3-1 has a concave part 3-12. The turnable handle 3-11 used to rotate the drum 3 together with the handle cover 3-1 is stowed in the concave part 3-12.

Figure 8A:
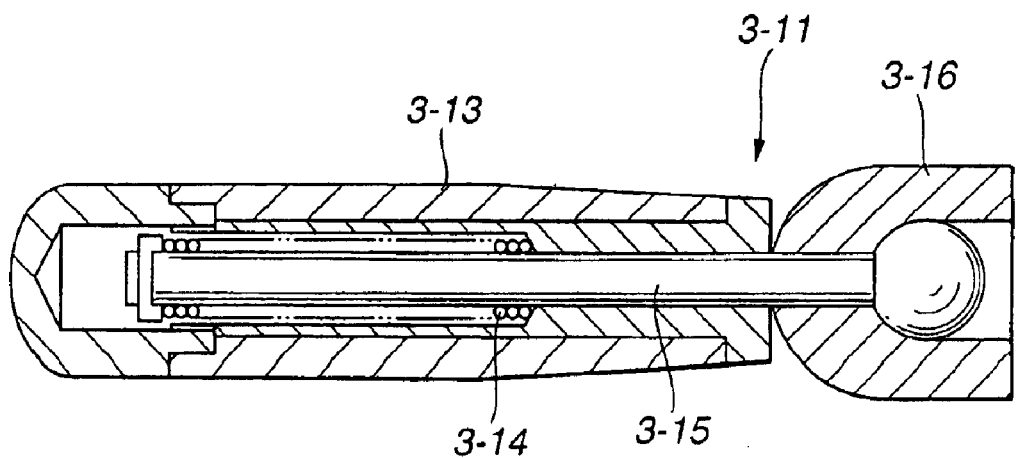
FIG. 8A is an enlarged view of the handle.

As shown in FIG. 8A, the handle 3-11 consists of a holder 3-13 that is hollowed and held by a user, a spring 3-14, a shaft 3-15, and a proximal stationary part 3-16. The spring 3-14 is compressed while being mounted on the periphery of the shaft 3-15 put in the hollow of the holder 3-13. The proximal end of the holder 3-13 is pressured onto the outer surface of the hemispherical part of the proximal stationary part 3-16 due to constraining force of the spring 3-14. The holder 3-13 is thus constrained to turn down.

The spherical end of the shaft 3-15 is locked in the substantially hemispherical concave part of the proximal stationary part 3-16.

The holder 3-13 of the handle 3-11 is normally turned down as indicated with a dot-dash line in FIG. 7A, and thus stowed so as not to jut out of the handle cover 3-1. When the handle 3-11 is unused, the handle 3-11 will never bother a user. This is user-friendly.

For rotating the drum 3, the holder 3-13 of the handle 3-11 is raised as indicated with a solid line in FIG. 7A to rest parallel to the axis of rotation. At this time, when the holder 3-13 is released, the handle 3-11 is returned to the original turned state owing to the constraining force of the spring 3-14 incorporated in the holder 3-13.

The handle 3-11 is used to rotate the drum 3 only when the insertion member 2-1 must be wound. At this time, the handle 3-11 is rotated clockwise. For drawing out the insertion member 2-1, the insertion member 2-1 is manually drawn out without use of the handle 3-11.

When the insertion member 2-1 is drawn out, if an attempt is made to rotate the handle 3-11 counterclockwise, the turnable holder 3-13 is turned down. Force is therefore not applied to the handle 3-11.

Figure 8B:
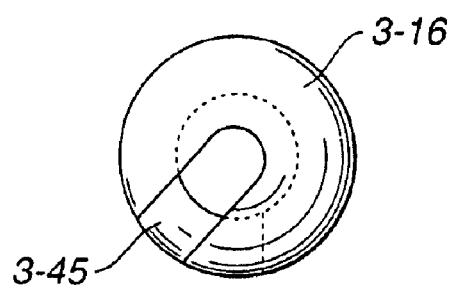
FIG. 8B is a front view of the apex of a stationary part of the handle.
Figure 8C:
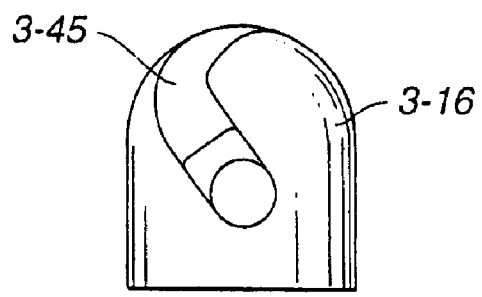
FIG. 8C is a plan view of the apex of the stationary part of the handle.

When the insertion member 2-1 is stowed, if the holder 3-13 is directed vertically as indicated with a solid line in FIG. 6 and as shown in FIG. 3B, the first case body 8-2 appears to have a neat design. Therefore, a guide groove 3-45 for guiding the shaft 3-15 is, as shown in FIG. 8B and FIG. 8C, formed in the proximal stationary part 3-16 so that the holder 3-13 will be first turned down counterclockwise and stowed vertically.

As mentioned above, since the handle 3-11 is turnable, when an attempt is made to rotate the drum 3 in a direction opposite to a direction of rotation permitting taking up of the insertion member 2-1, the handle 3-11 is likely to be turned down. An incorrect manipulation of rotating the drum in the direction opposite to the direction of rotation permitting taking up of the insertion member 2-1 can be prevented reliably.

Next, the structures of the front panel 5 and its surroundings will be described with reference mainly to FIGS 9A, 9B, 9C and 9D to FIG. 11.

Figure 10A:
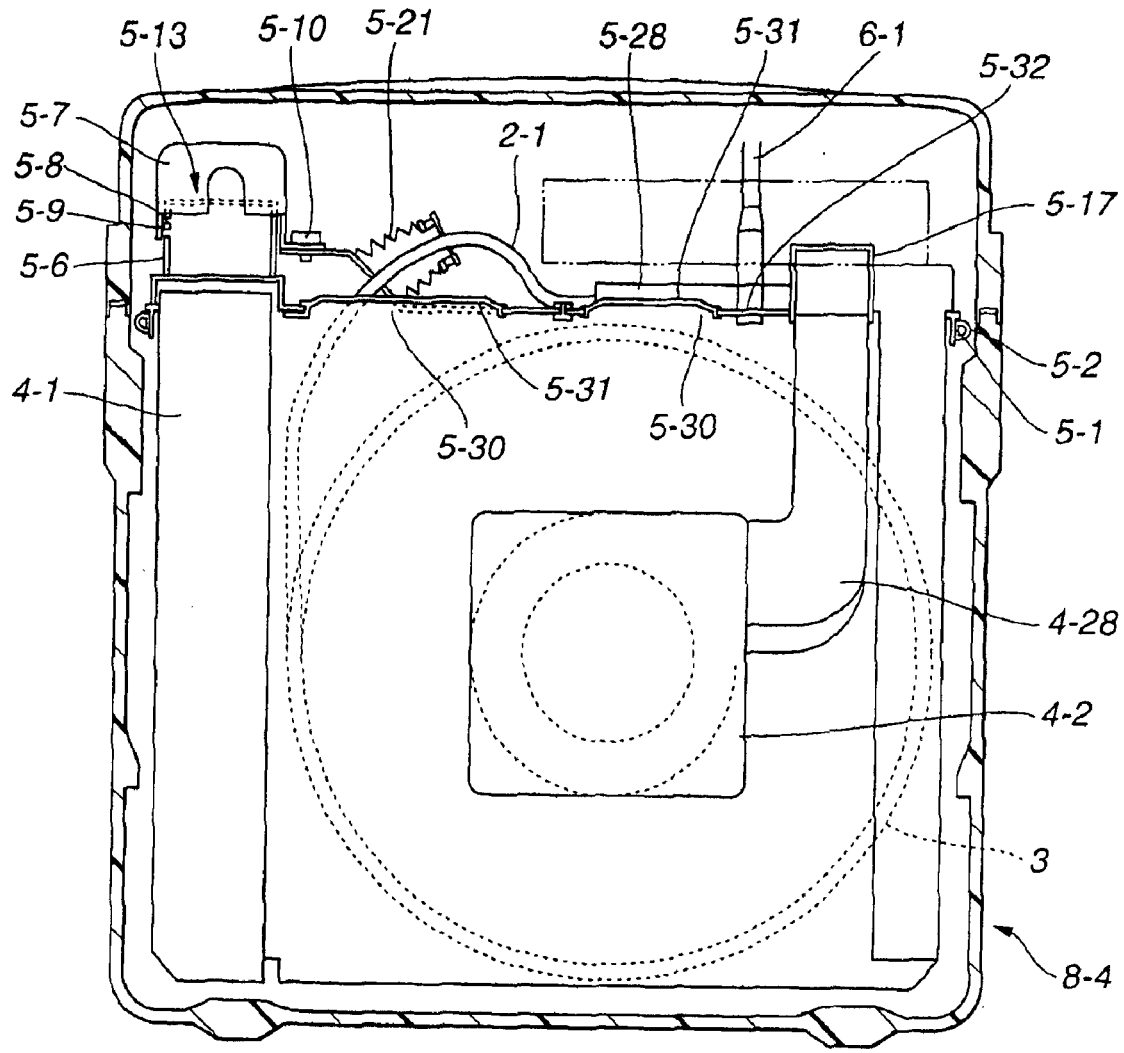
FIG. 10A is a side view of the front panel.

As shown in FIG. 9A, the front panel 5 is shaped like a substantially rectangular plate and made of a resin, and placed to block the entire opening 4-41 of the case body 8-4. A concave part 5-1 shown in FIG. 9D and FIG. 10A is formed over the edge of the front panel 5 that comes into contact with the case body 8-4. A rubber packing 5-2 is fitted in the concave part 5-1 in order to prevent invasion of rainwater or dust into the case body 8-4. The front panel 5 is integrated with the frame 4.

An inlet 5-3 is formed in one side on the top of the front panel 5. An ac receptacle 5-4 and a dc receptacle 5-5 are formed adjacently in the inlet 5-3 on the top of the panel.

Figure 10B:
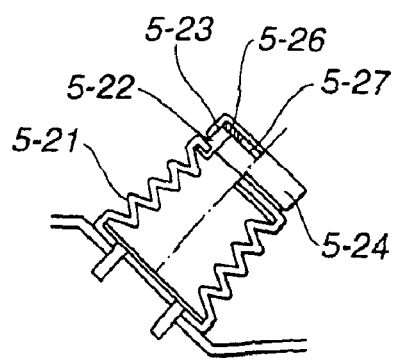
FIG. 10B is an enlarged view of a rubber boot.

A partition 5-6 surrounds the ac receptacle 5-4 and dc receptacle 5-5. A rainproof cover 5-7 is fixed in order to block an opening defined with the partition 5-6. As shown in FIGS. 10A and 10B, the partition 5-6 has a small window 5-8. The rainproof cover 5-7 is closed by tightening a thumb screw 5-10 with a convex part 5-9 formed on the rainproof cover 5-7 fitted into the small window 5-8.

As shown in FIG. 9B, when an L-shaped ac cable 5-11 is plugged in to the ac receptacle 5-4, the dc receptacle 5-5 is hidden behind the ac cable 5-11. The ac cable 5-11 and a dc cable 5-12 are therefore not plugged in simultaneously. As shown in FIG. 9C, when the L-shaped dc cable 5-12 is plugged in to the dc receptacle 5-5, the ac cable 5-11 cannot be plugged in to the ac receptacle 5-4.

Moreover, a groove is formed in the inner wall of the partition 5-6, and a sliding plate 5-13 is slid along the groove. When the sliding plate 5-13 is slid to one side, the sliding plate 5-13 blocks the ac receptacle 5-4 or dc receptacle 5-5. Therefore, even an ac cable and a dc cable that are not L-shaped cables cannot be plugged in simultaneously.

As shown in FIG. 9A, one intake vent 5-15, a first exhaust vent 5-16 and a second exhaust vent 5-17 are formed in the front panel 5. The intake vent 5-15 is elongated in the longitudinal direction of the front panel 5. The interior of the case is aerated through the intake vent 5-15.

Figure 11:
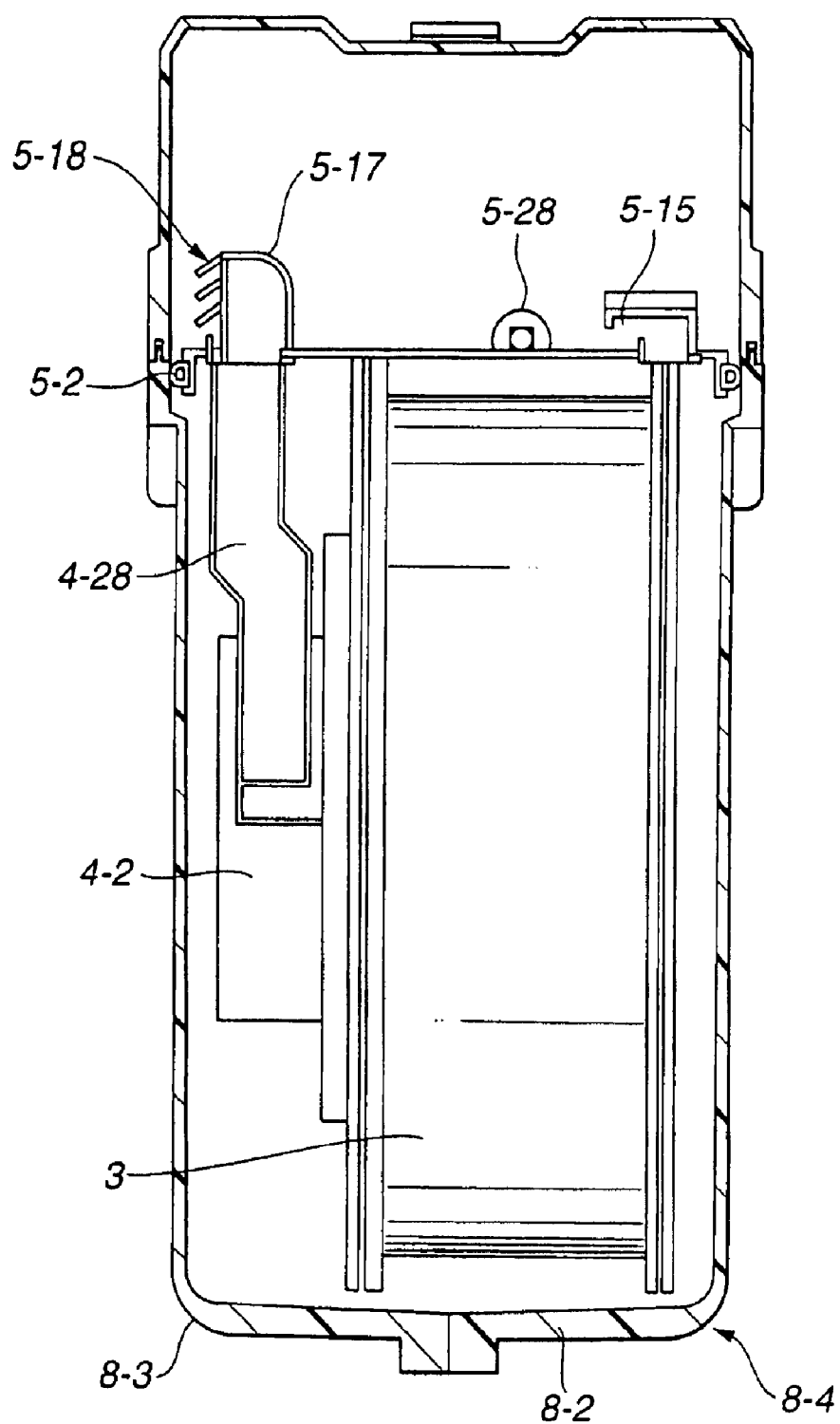

The first exhaust vent 5-16 is located behind the inlet 5-3. Heat dissipated from a power unit 4-1 located below is exhausted through the first exhaust vent 5-16. The second exhaust vent 5-17 is, as shown in FIG. 10A and FIG. 11, formed to communicate with an exhaust cylinder 4-28 extending from a scirocco fan 4-2 for the purpose of exhausting heat generated in the drum 3.

The three vents 5-15, 5-16, and 5-17 has a means devised for fear rainwater or the like may invade into the case through the vents. For example, as shown in FIG. 9D, an exhaust opening 5-18 may open sideways as part of the second exhaust vent 5-17. A plurality of caves 5-19 may be formed in order to prevent invasion of rainwater or the like through the opening 5-18.

Furthermore, a mesh 5-20 is laid over a plane from which the eaves 5-19 are projected. Consequently, foreign objects whose sizes are larger than a certain size will not invade into the case through the opening 5-18.

The number of eaves 5-19 and the pitch between adjoining eaves or the size of the bores in the mesh 5-20 is determined in consideration of efficiency in exhaustion. Moreover, a large eaves is formed to cover an intake opening of the intake vent 5-15 from above, and the tip of the eaves is bent for fear rainwater may drop into the vent. Even in this case, the size of the eaves or the like is determined in consideration of efficiency in aeration.

A pipe-like bearer member 5-28 is, as shown in FIG. 9A, formed on the front panel 5 in order to hold the tip of the insertion member for fear the tip of the insertion member 2-1, or especially, the optical system may be broken due to vibrations generated during transportation of the endoscope system 1. The tip of the insertion member 2-1 is stowed and held in the bearer member 5-28.

A metallic sub-panel 5-29 is screwed to the front panel 5. A controller connector 5-32, a video input/output connector, a voice connector, and a recording medium slot through which a PC card or a CF card is loaded are formed on or in the metallic sub-panel 5-29.

As shown in FIG. 10A, the sub-panel 5-29 has openings 5-30, and rainproof rubber caps 5-31 are fitted in the openings 5-30. The rainproof rubber caps 5-31 shield any of the connectors and slot that are not rainproof.

A detachable connector attached to the cable 6-1 is joined with the controller connector 5-32. As shown in FIG. 1, the cable 6-1 is elongated and soft. A signal cable or an optical communication cable over which a control signal and a video signal are transmitted runs through the cable 6-1. The proximal end of the cable 6-1 is led to the controller 6 that is a remote controller. The controller 6 has a joystick 6-2 and various control buttons 6-3. The joystick 6-2 serves as a means for bending the bending section 2-3 and also as an angling input unit.

Owing to the foregoing structure, the front panel 5 can be readily integrated with the case body 8-4, and the connectors can be readily joined with those formed on the front panel. Moreover, the reliability of the joined connectors can be guaranteed. Besides, watertightness of the front panel 5 and the case body 8-4 can be ensured.

Next, the structure of a portion of the drum 3 through which the insertion member 2-1 to be taken up or thrust out by the drum 3 is put or remove will be described below.

As shown in FIG. 9A and FIG. 10A, the bellows-like rubber boot 5-21 shaped like a pyramid is fixed to the front panel 5.

As shown in FIG. 10B, the rear end of a first metallic member 5-22 that is shaped substantially like a ring is fixed to the tip side opening of the rubber boot 5-21. A male screw 5-23 is threaded on the periphery of the first metallic member 5-22. A female screw 5-23 threaded in the inner wall of a second metallic member 5-24 that is shaped like a box nut is engaged with the male screw 5-23. The second metallic member 5-24 is thus freely detachably attached to the first metallic member 5-22.

Moreover, a packing 5-26 having an opening is interposed between the first metallic member 5-22 and second metallic member 5-24 so that the packing 5-26 can be removed freely. The opening 5-27 of the packing 5-26 has substantially the same diameter as the outer diameter of the insertion member 2-1. The insertion member 2-1 of the endoscope 2 is pulled out or taken up through the opening 5-27.

Owing to the foregoing structure, when the insertion member 2-1 is stowed, moisture adhering to the insertion member 2-1 can be rubbed off by the wall of the opening of the packing 5-26. After the insertion member 2-1 is repeatedly pulled out and stowed, the packing 5-26 may abrade. In this case, the second metallic member 5-24 is removed in order to replace the packing 5-26 with a new one.

The opening 5-27 of the packing 5-26 may be formed to be, for example, brushy so that the dirt adhering to the periphery of the insertion member 2-1 can be rubbed off reliably.

As mentioned above, foreign matters adhering to the periphery of the insertion member 2-1 can be rubbed off. Invasion of dirt into the interior of the drum causing a failure can be prevented. Moreover, an operator is relieved of the job of taking up the insertion member 2-1 while rubbing off dirt.

Next, a description will be made of the structure of a cable over which a signal is transferred between the interior of the drum 3 that is rotated and the exterior thereof that is not rotated. According to the present embodiment, as described later, a slip ring is not adopted but the spiral cable 3-2 is adopted so that an electric signal can be transmitted at a low cost.

Figure 12A:
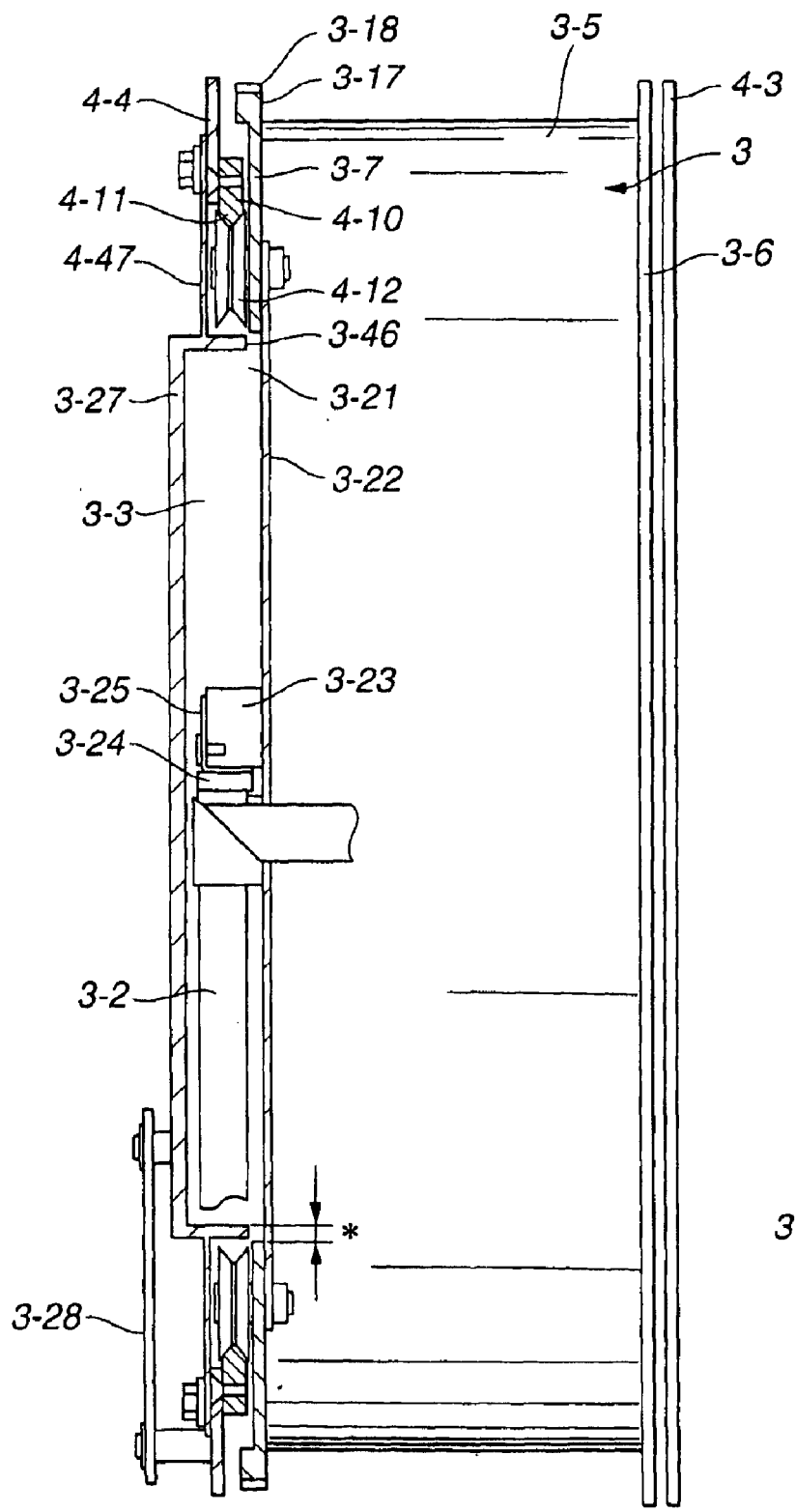
FIG. 12A is an explanatory diagram showing a rotationally holding mechanism included in a drum.
Figure 12B:
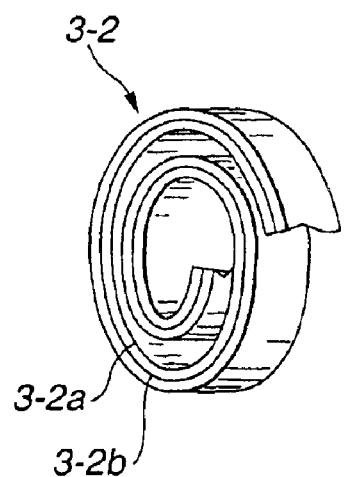
FIG. 12B shows a spiral cable.
Figure 15A:
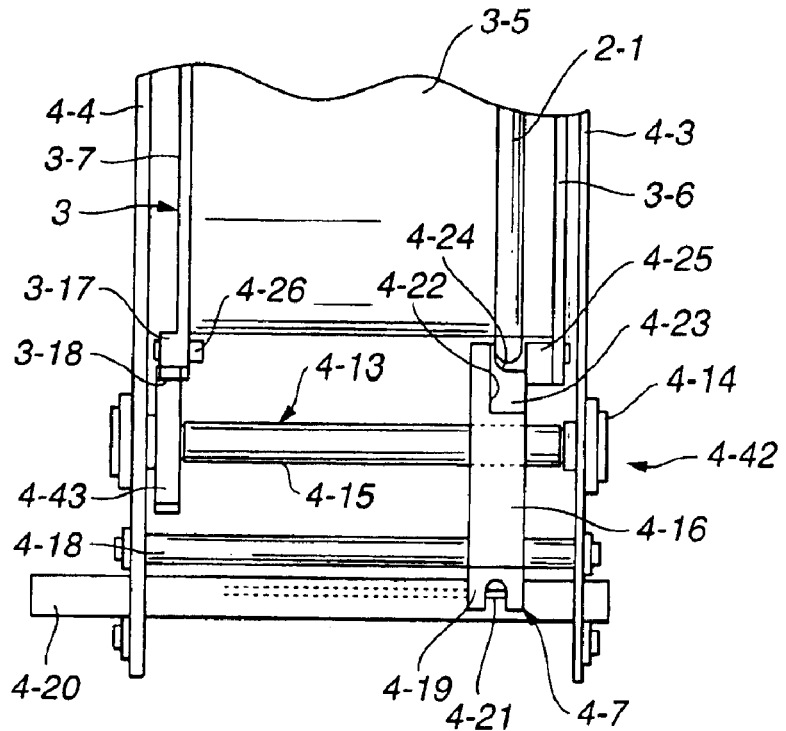
FIG. 15A shows the structure of a rotation sensor with an insertion member drawn out.

As shown in FIG. 12A and FIG. 15A, the second side panel 3-7 has a thick part 3-17 as the outer edge thereof, and a gear 3-18 is formed on the periphery of the thick part 3-17. As shown in FIG. 15A, the gear 3-18 conveys rotation to a gear 4-43 included in a rotation sensor 4-42 that senses the number of rotations made by the drum 3 about which the insertion member 2-1 is wound.

The opening 3-21 is formed in the center of the second side panel 3-7. A space beyond the opening 3-21 serves as a cable stowage 3-3 in which the cable 3-2, which electrically links the interior of the drum 3 and the exterior thereof, is stowed spirally.

Over the cable 3-2, power and information including control signals and a video signal are transferred between electric circuits incorporated in equipment stowed in the drum and electric circuits incorporated in equipment located outside the drum. The cable 3-2 is curled spirally with one flat cable or a plurality of flat cables, which are flexible, stacked up. The cable 3-2 shown in FIG. 12B has, for example, two flat cables 3-2a and 3-2b stacked up spirally.

When the cable 3-2 must contain a large number of conductors, if one flat cable is used as the cable 3-2, the cable 3-2 has a large width. The cable stowage 3-3 must have a large volume. However, since a plurality of flat cables is stacked up, the width of the cable 3-2 is not so large. The flat cable 3-2 is realized with flat cables, ribbon cables, or flat flexible cables (FFCs). Moreover, when the cable 3-2 may contain only a small number of conductors, one flat cable is used as the cable 3-2.

As shown in FIG. 12A, the second drum cover 3-22 is secured inside the opening 3-21 within the drum. A hollowed shaft 3-23 for locking the cable 3-2 is attached to the center of the outer surface of the second drum cover 3-22 outside the drum. The cable 3-2 is locked in the shaft 3-23 with a locking member 3-25, to which an elastic member 3-24 is bonded, attached to the shaft 3-23. The end of the cable 3-2 passes, as shown in FIG. 13C, through the hollow and enters the interior of the drum. The end of the cable 3-2 is led to a relay printed-circuit board 3-28 incorporated in the drum as shown in FIG. 17A.

A cover member 3-27 is located outside the spirally curled cable 3-2. The outer edge of the cover member 3-27 is folded in the shape of letter L to serve as a convex part 3-46. The convex part 3-46 restricts the spread of the cable 3-2 to a certain diameter, or in other words, prevents the cable 3-2 from spreading wider than the certain diameter. This restricts a range of the cable 3-2 to be curled in an axial direction and prevents destruction of the spiral shape.

A plurality of projections 4-47 is projected from the convex part 3-46 of the cover member 3-27, and fixed to the second frame 4-4.

Figure 14:
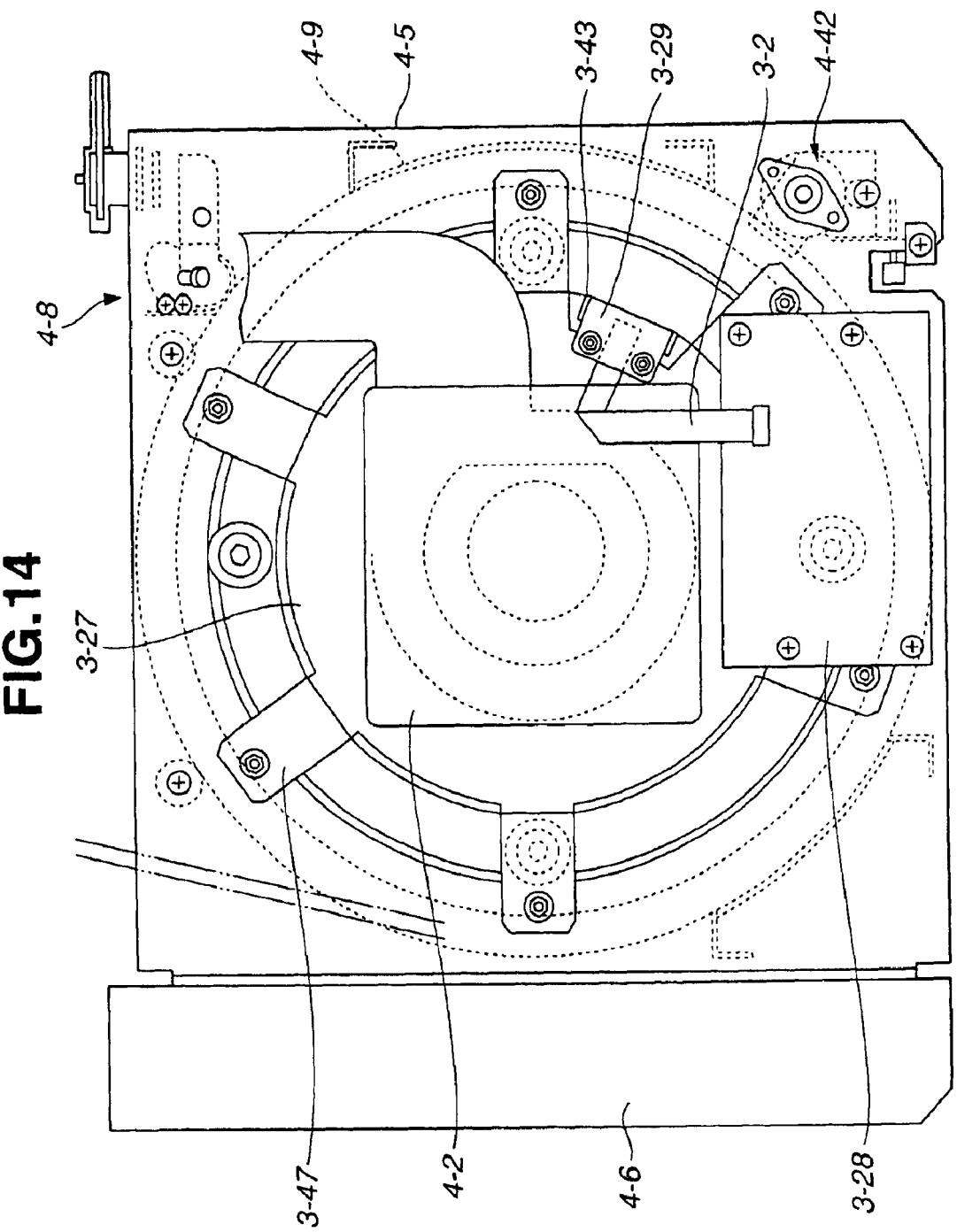

As shown in FIG. 14, the cable 3-2 is drawn out of the cover member 3-27 through a slit 3-43 formed along the outer edge of the cover member 3-27, and led to the relay printed-circuit board 3-28. The cable 3-2 drawn out of the cover member 3-27 is settled while being sandwiched between a settling member 3-29 fixed to the cover member 3-27 and the cover member 3-27.

For minimizing the width of the drum stowage, the second drum cover 3-22 is fixed to the inner surface of the second side panel 3-7 by inserting a screw from inside the drum. This results in the minimized thickness and width of the second side panel 3-7.

A primary power line is contained in the flat cable 3-2. It is therefore necessary to ensure electric isolation between the flat cable and its surrounding members. In the endoscope system 1, since the ground terminal of the ac receptacle 5-4 is connected to a ground, the frame 4 is grounded reliably. However, the drum 3 held to be rotatable is not grounded. Measures described below are therefore taken in order to meet predetermined standards concerning prevention of an electric shock.

The second drum cover 3-22 and hollow shaft 3-23 are fixed to the second side panel 3-7 of the drum 3 that is not grounded. Therefore, the second drum cover 3-22 and shaft 3-23 are made of a resin or any other insulating material.

Otherwise, an isolator member such as a Mylar sheet is interposed between the second drum cover 3-22 and cable 3-2, and between the shaft 3-23 and cable 3-2.

The second side panel 3-7 of the drum 3 is made of a metal. Therefore, the distance between the cable 3-2 and the second side panel 3-7 is set to a standardized distance or longer. In the endoscope system 1, a dimension * in FIG. 12A is set to approximately 3.2 mm or more.

In the drum 3, an isolator member such as a Mylar sheet is interposed between the cable 3-2 and the relay printed-circuit board 3-28 incorporated in the drum 3, and between the cable 3-2 and a secondary signal line.

Furthermore, the cover member 3-27 and settling member 3-29 are made of a metal so that they can conduct electricity to the second frame 4-4 of the frame 4 that is grounded.

Outside the cover member 3-27, an isolator member such as a Mylar sheet is interposed between the cable 3-2 and a printed-circuit board 3-28 located outside the drum and between the cable 3-2 and a secondary signal line.

Figure 17B:
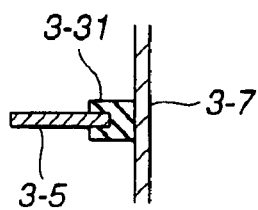
FIG. 17B is a 17B—17B sectional view of part of FIG. 17A.

As shown in FIG. 17A, a plurality of columns 3-30 is placed along the outer edges of the first side panel 3-6 and second side panel 3-7. The columns 3-30 link the first side panel 3-6 and second side panel 3-7. The cylindrical member 3-5 is located outside the columns 3-30 in contact with the columns 3-30. A U-shaped packing 3-31 is, as shown in FIG. 17B, attached to the edges of the cylindrical member 3-5 in order to seal gaps. Invasion of rainwater or dust through the gaps between the cylindrical member 3-5, and the first side panel 3-6 and second side panel 3-7 is thus prevented reliably.

The proximal part 3-32 of the insertion member 2-1 is secured within the drum 3. The insertion member 2-1 is extended outside through a notch 3-33 formed in the cylindrical member 3-5. A packing 3-34 is fitted in gaps between the notch 3-33, and the insertion member 2-1 and first side panel 3-6 in order to prevent invasion of rainwater or dust through the notch 3-33 serving as an insertion member exit.

For stowing the insertion member 2-1, the drum 3 is rotated in a predetermined direction. Consequently, the insertion member 2-1 is wound about the periphery of the drum 3.

As shown in FIG. 19, a lead member 3-35 is fixed to a point near the notch 3-33 of the cylindrical member 3-5. The lead member 3-35 prevents one part of the insertion member 2-1 from overlapping another part thereof when the insertion member 2-1 is wound by one turn with the proximal part 3-32 fastened.

As partly shown in FIG. 12A, FIG. 14, and FIGS. 15A and 15B, the frame 4 consists of the first frame 4-3, the second frame 4-4, a locking member 4-5, a power supply 4-6, the rotation sensor 4-42, a stopper 4-7, a detent 4-8, and a restricting member 4-9. The locking member 4-5 links the first frame 4-3 and second frame 4-4. The rotation sensor 4-42 senses the number of rotations made by the drum 3. The stopper 4-7 prevents the insertion member 2-1 from being excessively taken up or drawn out. The detent 4-8 prevents rotation of the drum during transportation of the case. The restricting member 4-9 prevents the insertion member 2-1 from spreading outwards.

Next, a description will be made of a structure for rotatably cantilevering the drum 3 freely.

As shown in FIG. 12A, a flange 4-10 looking like an annular rail is secured in a space, which is created beyond the second side panel 3-7 inside the second frame 4-4, concentrically with the drum 3. The periphery of the inner edge of the flange 4-10 is shaped like a wedge or letter V, and thus serves as a V-shaped part 4-11.

Figure 13A:
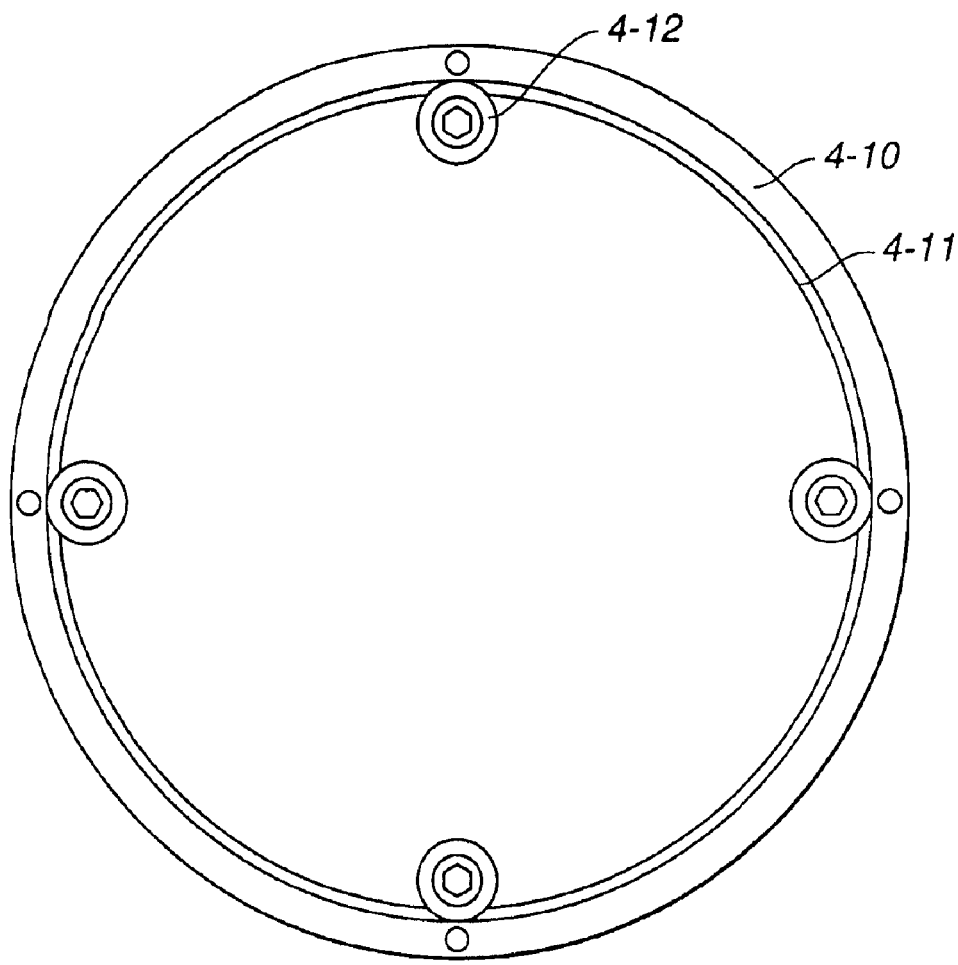
FIG. 13A shows a flange included in the rotationally holding mechanism shown in FIG. 12A and bearings for rotatably holding the flange at a plurality of points freely.

As shown in FIG. 12A and FIG. 13A, the V-shaped part 4-11 is engaged with the grooves of a plurality of bearing members 4-12, for example, three or four bearing members 4-12.

Figure 13B:
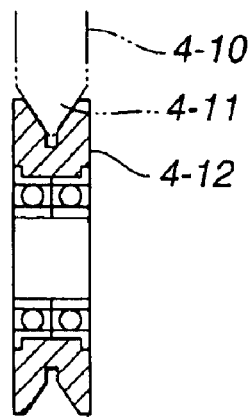
FIG. 13B is an enlarged sectional view of the bearing.
Figure 13C:
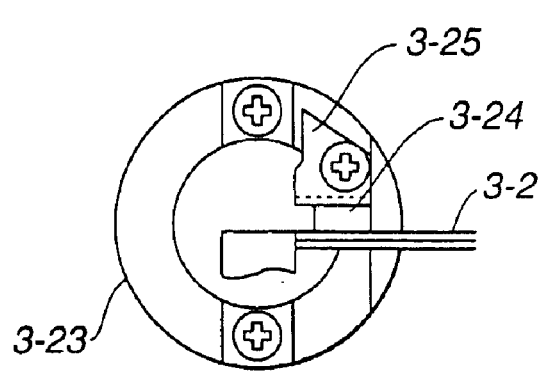
FIG. 13C is an explanatory diagram showing a cable introduced to the drum from a cable stowage.

As shown in FIG. 13B, the bearing members 4-12 are each hollowed. A ball bearing is interposed between the inner and outer edges of each bearing member, and the outer edge can freely rotate. Moreover, a V-shaped groove with which the V-shaped part 4-11 is engaged as indicated with an alternate long and two short dashes line is formed in the periphery of the outer edge. The V-shaped part 4-11 is engaged with the V-shaped grooves, and the outer edges of the bearing members having the V-shaped grooves can freely rotate. The bearing members 4-12 are fixed to the second side panel 3-7 with screws inserted into the hollows thereof.

Using the flange 4-10 fixed to the second frame 4-4 as a circular guide rail, the second side panel 3-7 having a bearing realized with the bearing members 4-12 is held to be freely rotatable. Consequently, the drum 3 is rotatably held inside the second frame 4-4 freely. The flange 4-10, bearing members 4-12, and other members are interposed between the second side panel 3-7 and the second frame 4-4. An excess space need not be preserved.

Specifically, the plurality of bearing members constituting a bearing is fixed to one side panel of the drum 3 concentrically with the drum 3. The annular rail concentric with the drum and having a receiving surface that receives the bearing is mounted on the frame that supports and locks the drum 3. The bearing members and annular rail constituting a rotating drum supporting structure is located away from a structure lying near the center of rotation of the drum 3. Consequently, the drum can be structured readily and inexpensively. Nevertheless, the cable stowage 3-3 or the like can be located in the center of rotation, and signals can be transferred between the interior and exterior of the drum. Moreover, the drum can be designed compactly.

Moreover, since the bearing is realized with the ball bearings, the drum 3 can be rotated smoothly. The outer edges of the bearing and the rail are provided as V-shaped concave and convex parts respectively that are engaged with each other. Even when the drum 3 is placed lengthwise or sideways, the drum 3 can rotate smoothly.

Next, a description will be made of a sensing mechanism for sensing the length of one portion of the insertion member 2-1 that is wound about the drum or the length of the other portion thereof that is not wound.

Figure 15B:
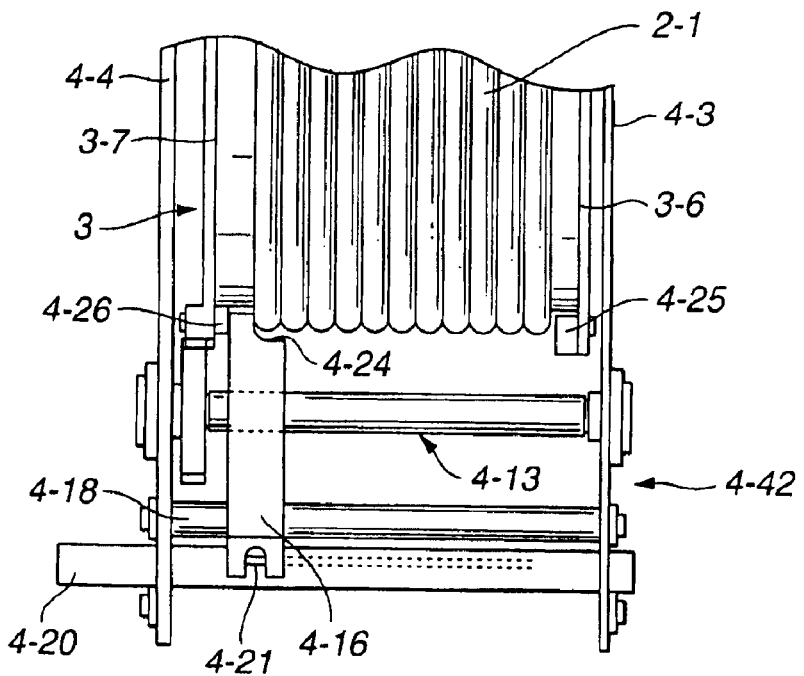
FIG. 15B shows the structure of the rotation sensor with the insertion member taken up.

As shown in FIGS. 15A and 15B, a shaft 4-13 for sensing the number of rotations is located in the vicinity of the drum 3, or more particularly, under the bottom of the drum 3. The shaft 4-13 lies parallel to the axis of rotation of the drum 3, and penetrates through the first frame 4-3 and second frame 4-4. Both ends of the shaft 4-13 are rotatably held in holding members 4-14 freely. The holding members 4-14 are fixed to predetermined points on the frames 4-3 and 4-4 respectively, and exhibits a low coefficient of friction. A gear 4-43 is attached to the shaft 4-13 so that the gear 4-43 will be engaged with the gear 3-18 formed on the periphery of the second side panel 3-7.

A male screw 4-15 is threaded in a portion of the shaft 4-13 opposed to the cylindrical member 3-5 of the drum. A moving member 4-16 having a female screw threaded thereon is mounted on the shaft 4-13. The female screw is engaged with the male screw 4-15.

Figure 16A:
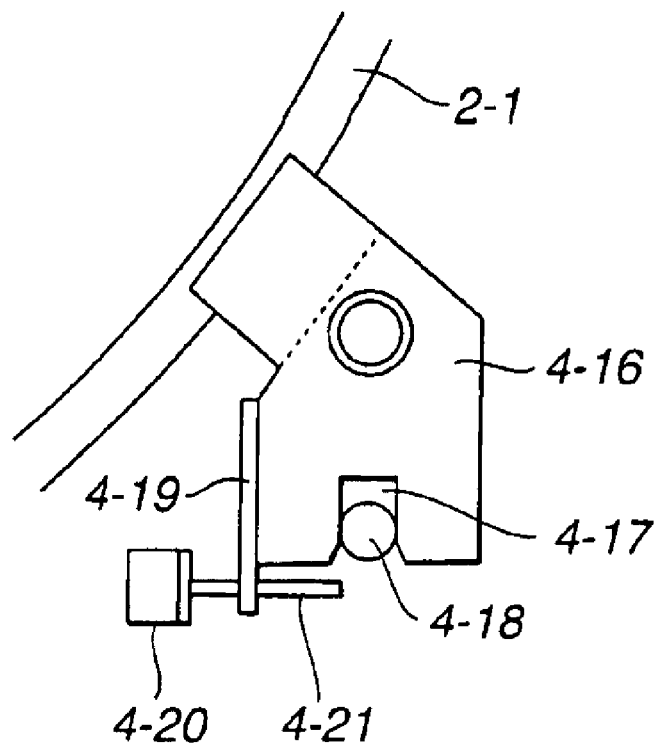
FIG. 16A shows the structures of a moving member and its surroundings.

As shown in FIG. 16A, the moving member 4-16 has a concave part 4-17 formed along a lower edge thereof. Ends of a restriction bar 4-18 for preventing the moving member 4-16 from revolving around the shaft 4-13 are fixed to the frames 4-3 and 4-4. The restriction bar 4-18 is located to coincide with the concave part 4-17.

Moreover, the moving member 4-16 has a bearer 4-19 fixed to clamp a lever 4-21 coupled to a variable resistance terminal of a sliding variable resistor 4-20. The sliding variable resistor 4-20 is fixed to the locking member 4-5, which is shown in FIG. 14, linking the frames 4-3 and 4-4.

Consequently, when the drum 3 rotates, the shaft 4-13 rotates. This causes the moving member 4-16 to, as shown in FIG. 15A and FIG. 15B, move laterally along the shaft 4-13. When the moving member 4-16 moves along the shaft 4-13, the lever 4-21 of the sliding variable resistor 4-20 moves. The resistance of the variable resistor 4-20 varies corresponding to a distance moved by the lever 4-21. This results in an electric signal proportional to the resistance.

Moreover, the moving member 4-16 is metallic and has a notch 4-22 formed on an edge thereof opposed to the drum. An insertion member bearer member 4-23 made of a resin and permitting smooth sliding is attached to the notch 4-22. The insertion member bearer member 4-23 has a curved surface 4-24 formed in line with the outer surface of the insertion member 201.

Consequently, when the drum 3 is rotated in a direction of rotation permitting taking up of the insertion member 2-1, the moving member 4-16 moves from the first frame 4-3 to the second frame 4-4 with the curved surface 4-24 of the insertion member bearer member 4-23 in contact with the outer surface of the insertion member 2-1. For example, when the drum is rotated with the state shown in FIG. 16A maintained, the moving member 4-16 moves upwards in the sheet of the drawing while being in contact with the insertion member 2-1.

Figure 16B:
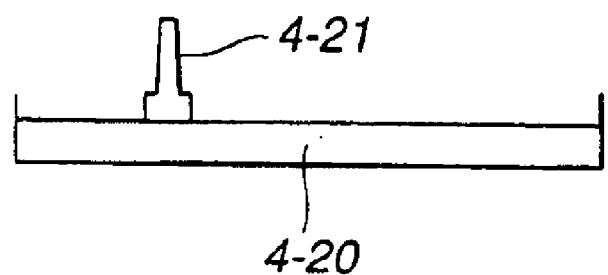
FIG. 16B is an explanatory diagram concerning a sliding variable resistor.

In this case, the lever 4-21 jutting out of the sliding variable resistor 4-20 as shown in FIG. 16B moves together with the moving member 4-16 while being clamped, as shown in FIG. 16A, by the bearer 4-19 of the moving member 4-16. This causes the resistance at the variable resistance terminal to vary. A length by which the insertion member 2-1 is rotated and wound about the drum 3 can be detected based on the variation of the resistance.

The gear ratio of the gear 3-18 to the gear 4-43 and the pitch between adjoining threads of the screw of the shaft 4-13 are adjusted in order to allow the drum 3 to rotate once. In other words, when the insertion member 2-1 is wound by one turn, the moving member 4-16 moves by a distance corresponding to the outer diameter of the insertion member 2-1. Consequently, the insertion member 2-1 is wound in a row around the cylindrical member 3-5.

As seen from FIGS. 15A and 15B, the number of teeth of the gear 3-18, which is formed on the drum 3, engaged during one rotation thereof is much larger than the number of teeth the gear 4-43, which is attached to the shaft 4-13, engaged during one rotation thereof. With one rotation of the drum 3, the shaft 4-13 rotates a plurality of times.

To be more specific, even when the insertion member 2-1 is taken up by a length that is much smaller than a length by which the insertion member 2-1 is wound by one turn about the cylindrical member 3-5 of the drum 3, the length can be detected. Moreover, the pitch of the male screw 4-15 threaded on the periphery of the shaft 4-13 is determined so that a length by which the insertion member 2-1 is taken up can be detected with required precision.

For example, the insertion member 2-1 can be set to any wound state intermediate between a state in which the insertion member 2-1 is, as shown in FIG. 15A, drawn out to the greatest extend and a state in which the insertion member 2-1 is, as shown in FIG. 15B, wound up. The resistance of the sliding variable resistor 4-20 varies corresponding to the wound state. Consequently, the wound state or a length by which the insertion member 2-1 is wound can be detected based on the variation of the resistance.

The rotation sensor 4-42 including the sliding variable resistor 4-20 holds length information as if it were a non-volatile storage. In other words, even when the power supply is turned on after being turned off, the resistance remains at a value associated with a length by which the insertion member 2-1 is wound. The rotation sensor 4-42 is therefore much more advantageous than another type of sensor that must be reset or initialized every time the power supply is turned on and that holds length information in a volatile manner.

The lever 4-21 of the sliding variable resistor 4-20 is move mechanically, and length information is detected based on the point to which the lever is moved. A length can therefore be measured independently of whether the power supply is turned on or off. Whenever the power supply is turned on, the length information is communicated in the form of an electric signal.

The length information is communicated to, for example, a motor-driven angling control circuit unit (hereinafter a control circuit unit) 3-38 that controls angling performed by the motor-driven angling unit 3-37 shown in FIG. 17A. The length information can thus be utilized for optimal control of angling based on the wound state of the insertion member 2-1.

Assume that a case where the insertion member 2-1 is angled when a portion of the insertion member 2-1 wound about the drum 3 occupies a larger percentage is compared with a case where the insertion member 2-1 is angled when the insertion member is hardly wound and can be angled freely. Even if the angulation wires are pulled in the same manner between the cases, a magnitude of bending, that is, an angle of bending made by the bending section 2-3 varies depending on the case.

Moreover, when the insertion member 2-1 is wound about the drum 3, the state of the insertion member 2-1 is almost the same as a state thereof in which the insertion member should not be angled. A larger drive is needed for angling the insertion member in response to an operator's angling instruction than it is needed when the insertion member 2-1 is not wound. Desirably, therefore, the insertion member should be able to be angled in the same manner all the time irrespective of a length by which the insertion member is wound.

When the bending section 2-3 must be bent in response to an angling instruction with the insertion member 2-1 nearly wound up, unless excess force is applied to the angulation wires, the bending section 2-3 cannot be driven to bend. At this time, if control is given in order to disable angling, the angulation wires can be prevented from being stretched or cut due to the excess force.

The outer diameter of the first side panel 3-6 and second side panel 3-7 are larger than the outer diameter of the cylindrical member 3-5 by at least a double of the diameter of the insertion member. Therefore, the insertion member 2-1 will not come off outwards from the side panel.

As shown in FIG. 15A, a first block 4-25 and a second block 4-26 are fixed to the inner surfaces of the outer edges of the first side panel 3-6 and second side panel 3-7 respectively. The first block 4-25 is located at a position at which when the insertion member 2-1 is fully drawn out, the moving member 4-16 abuts on the first block. When the moving member 4-16 abuts on the first block 4-25, the movement of the insertion member 2-1 is hindered. Therefore, the insertion member 2-1 cannot be drawn out any longer.

On the other hand, the second block 4-26 is, as shown in FIG. 15B, located at a position at which when the insertion member 2-1 is wound up, the moving member 4-16 abuts on the second block. Even in this case, the moving member 4-16 abuts on the second block 4-26 to hinder the movement of the insertion member. The insertion member 2-1 cannot therefore be wound any longer.

As mentioned above, the stopper 4-7 is realized in order to prevent the insertion member 2-1 from being excessively taken up or drawn out.

Next, the arrangement of components within the drum 3 will be described with reference to FIG. 17A.

As shown in FIG. 17A, the light source unit 3-36, motor-driven angling unit 3-37, control circuit unit 3-38, camera control unit (CCU) 3-39, and relay printed-circuit board 3-26 are arranged in the internal space of the drum 3. The light source unit 3-36 supplies illumination light, which is used for observation, to the endoscope 2. The motor-driven angling unit 3-37 includes a driving source for driving a driving mechanism that drives the bending section 2-3 using motors. The control circuit unit 3-38 controls motor-driven bending of the bending section 2-3 to be performed in response to an instruction signal sent from the joystick 6-2 included in the controller 6. The CCU 3-39 includes an image processing circuit that converts an image signal, which results from photoelectric conversion performed by the CCD 25, into a TV signal, and a timing signal generation circuit that generates a timing signal used to drive the CCD 25. The relay printed-circuit board 3-26 electrically connects the interior of the drum 3 to the exterior thereof.

The light source unit 3-36 consists of a lamp unit 3-40, a light guide connector 3-41, and a lamp lighting unit 3-42. The lamp unit 3-40 is composed of a metal halide lamp and a reflector that are freely detachable. Converged light is propagated over the light guide 21, which runs through the insertion member 2-1, through the light guide connector 3-41. The lamp lighting unit 3-42 has chamfered portions 3-46, and is therefore efficiently stowed in the cylindrical member 3-5.

The relay printed-circuit board 3-26 is placed between the light source unit 3-36, and the other components including the motor-driven angling unit 3-37, control circuit unit 3-38, and CCU 3-39. The relay printed-circuit board 3-26 fills the role of a heat insulator. The relay printed-circuit board 3-26 insulates heat generated by the light source unit 3-36 for fear the heat may be conveyed to the motor-driven angling unit 3-37, control circuit unit 3-38, and CCU 3-39.

FIG. 18 shows a major portion of the interior of the drum 3 that is seen through the opening 3-8 with the first drum cover 3-9 removed.

As illustrated, a portion of the motor-driven angling unit 3-37 that adjusts a sag in the angulation wires 32u and 32d is exposed so that an angle of bending can be adjusted readily.

To be more specific, after angling is repeated for a prolonged period of time, the angulation wires sag compared with the angulation wires that have just been initialized and adjusted. When the angulation wires are manipulated by a predetermined magnitude of driving, an angle by which the bending section bends may be smaller than it is when the angulation wires are initialized. In this case, the sag adjuster is manipulated in order to absorb the sag and to thus bring the angulation wires back to the initial state.

Incidentally, referring to FIG. 18, the adjuster for adjusting the sag in the angulation wires located vertically or laterally is exposed. The other adjuster for adjusting the sag in the angulation wires located laterally or vertically is located under the above adjuster. Consequently, the sag can be adjusted easily.

Moreover, when the first drum cover 3-9 is removed, the lamp unit 3-40 is also exposed. This enables a user to readily replace a lamp with a new one.

Next, a description will be made of the structure of the detent 4-8 for preventing rotation of the drum during transportation.

As shown in FIG. 9A and FIG. 20A, the front panel 5 has an operator lever 4-35 exposed thereon.

As shown in FIG. 20B and FIG. 20C, the operator lever 4-35 has a presser pin 4-36 jutted inwards beyond the back surface of the front panel 5. The presser pin 4-36 is located so that a moving plate 4-30 that can freely swivel with a rotation shaft 4-29 as a center will abut on the tip of the presser pin 4-36. The moving plate 4-30 is fixed to the second frame 4-4.

A one-way gear 4-31 having a clutching mechanism and being rotatable only in one direction is fixed to the one end of the moving plate 4-30 using a gear shaft 4-32.

A blade spring 4-33 is fixed to the second frame 4-4, and constrains the moving plate 4-30 to move in a certain direction all the time. Consequently, the one-way gear 4-31 is engaged with the gear 3-18 formed on the periphery of the second side panel 3-7.

When the gear 3-18 is engaged with the one-way gear 4-31, the drum 3 can be rotated in a direction associated with a direction of clockwise rotation of the handle 3-11, that is, a direction of rotation permitting taking up of the insertion member 2-1 owing to the capability of a clutch the one-way gear 4-31 has. However, the drum 3 cannot be rotated in an opposite direction, that is, a direction of rotation permitting drawing out of the insertion member.

In other words, after an endoscopic inspection is completed, the insertion member 2-1 is taken up in order to straighten up the endoscope system 1. When the insertion member 2-1 is wound up, the moving member 4-16 hits the second block 4-26. Consequently, the drum 3 cannot any longer be rotated in the direction of rotation permitting taking up of the insertion member. Besides, the drum 3 does not rotate even in the direction of rotation permitting drawing out of the insertion member owing to the one-way gear 4-31. The drum 3 is therefore locked and disabled to rotate.

A freeing mechanism 4-34 for freeing the one-way gear 4-31 from the gear 3-18 formed on the periphery of the second side plate 3-7 is located near the other end of the moving plate 4-30.

The freeing mechanism 4-34 consists of the operator lever 4-35, presser pin 4-36, and spring 4-37. When the endoscope system 1 is preserved, the operator lever 4-35 is set to a position indicated with a dashed line in FIG. 20A, that is, set to a state shown in FIG. 20B.

In this state, when the operator lever 4-35 is pushed down, the presser pin 4-36 is pressed. This causes the moving plate 4-30 to swivel. Consequently, the one-way gear 4-31 is freed from the gear 3-18. The insertion member 2-1 can be drawn out. When pushing down the operator lever 4-35 is stopped, the operator lever 4-35 is returned to the original position owing to the constraining force of the spring 4-37.

When the operator lever 4-35 is turned by about 90° while being pushed down, the presser pin 4-36 moves downwards. Consequently, the freed state shown in FIG. 20C is retained in which the moving plate 4-30 is left swiveled.

Specifically, the presser pin 4-36 has a convex part as shown in FIG. 20D, and is passed through a key groove formed in a holding plate 4-44. Therefore, when the presser pin 436 is pushed down against elastic stress exerted by the spring 4-37, the convex part comes off from the key groove to be freely rotatable. When the convex part is rotated by, for example, 90°, the convex part is held off from the key groove as shown in FIG. 20E.

Normally, the operator lever 4-35 is pushed down and turned to enter a state shown in FIG. 20C.

When the operator lever 4-35 is set to the state shown in FIG. 20C, the operator lever 4-35 lies in the part of the case body 8-4 that engages with the lid 8-5 of the case 8. The lid 8-5 will therefore not be closed.

Therefore, when the one-way gear is freed, that is, the drum 3 can freely rotate both in a direction of rotation permitting taking up of the insertion member and a direction of rotation permitting drawing out thereof, even if an attempt is made to close the lid 8-5 so as to transport the endoscope system, the lid 8-5 is not closed. A user can therefore be aware of the fact that the one-way gear is freed. The user then performs manipulations to terminate the freed state. Consequently, the user can close the lid 8-5.

In the present embodiment, when the operator lever 4-35 is pushed, the gear 4-31 is freed from the gear 3-18. The present invention is not limited to the present embodiment. Alternatively, when the operator lever 4-35 is pulled up, the gear 4-31 may be freed from the gear 3-18.

Next, the structure of the liquid crystal monitor unit 7 will be described below.

Figure 21A:
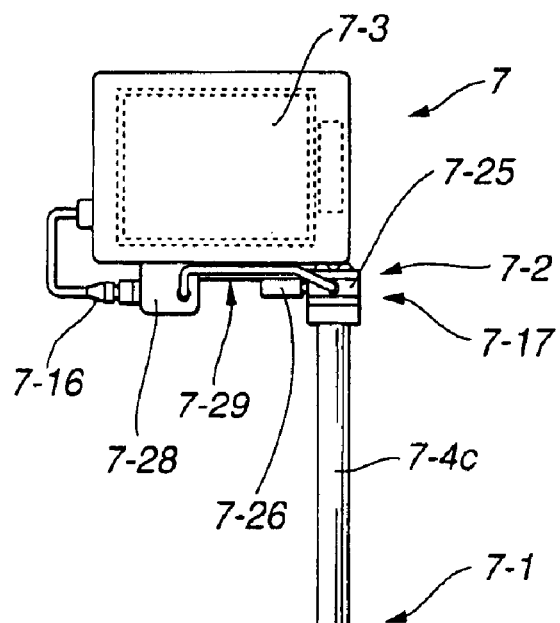
FIG. 21A shows a liquid crystal monitor unit with a pole stretched.
Figure 21B:
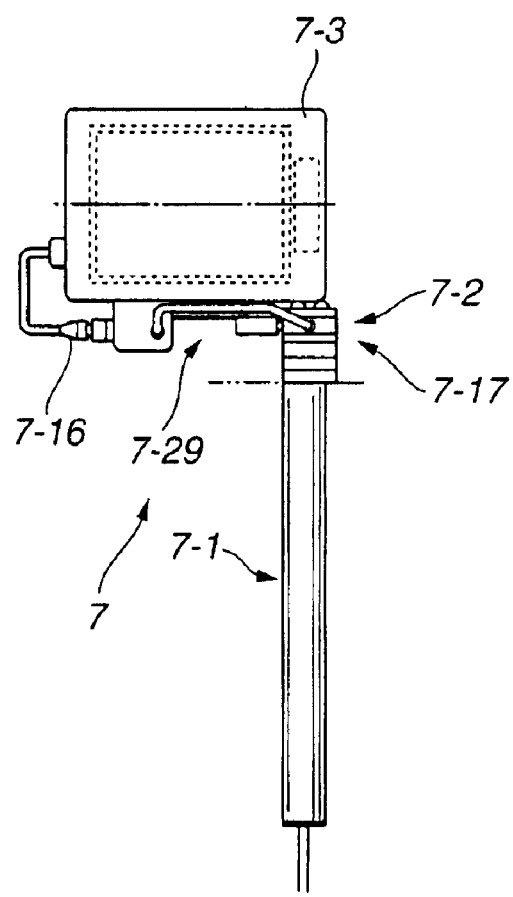
FIG. 21B shows the liquid crystal monitor unit with the pole contracted.

As shown in FIG. 21A and FIG. 21B, the liquid crystal monitor unit 7 consists of the liquid crystal monitor 7-3, stretchable pole 7-1, and rotating mechanism 7-2. The rotating mechanism 7-2 is used to couple the liquid crystal monitor 7-3 to the stretchable pole 7-1 so that the liquid crystal monitor 7-3 can swivel freely. In the drawing, the liquid crystal monitor is seen from the back thereof.

Figure 23A:
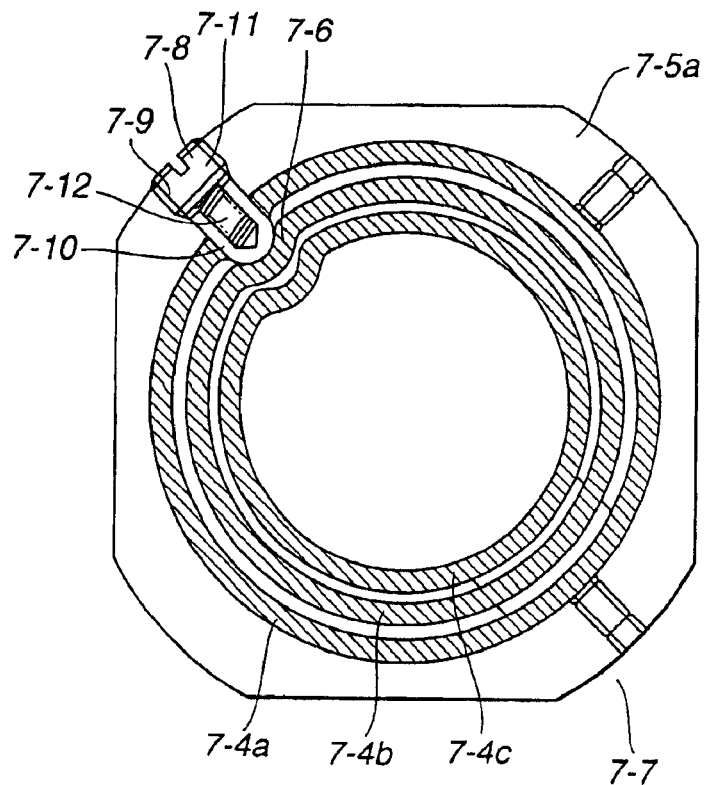
FIG. 23A is a 23A—23A sectional view of the structure shown in FIG. 22A.

The stretchable pole 7-1 has a plurality of cylinders, or in the present embodiment, three cylinders 7-4a, 7-4b, and 7-4c nested. The cylinders 7-4a, 7-4b, and 7-4c have different diameters. The cross sections of the cylinders 74i (where i denotes a, b, and/or c) perpendicular to the axial directions thereof have a round shape, and each have, as shown in FIG. 23A, a dent 7-6. The cylinders 7-4i are positioned with the dents 7-6 aligned with one another, and can therefore be axially stretched or contracted without being rotated.

As shown in FIG. 22A, a first crown 7-5a is fixed to the upper part of the first cylinder 7-4a, which has the largest diameter, using a screw 7-7 shown in FIG. 23A. Likewise, a second crown 7-5b is fixed to the upper part of the second cylinder 7-4b having the second largest diameter, and a third crown 7-5c is fixed to the upper part of the third cylinder 7-4c having the smallest diameter.

The first crown 7-5a has a through hole 7-8 formed to extend towards the axial center of the cylinder. A female screw 7-9 is, as shown in FIG. 23A, threaded on the inner wall of the through hole 7-8 near the entrance thereof. A frictional pin 7-10 is inserted into the through hole 7-8. A spring 7-12 is fitted in the concave part of the frictional pin 7-10.

A presser screw 7-11 is engaged with the female screw 7-9. The first cylinder 7-4a is locked with the dent 7-6 coincident with the frictional pin 7-10. Furthermore, the first cylinder 7-4a has an opening whose diameter is larger than the outer diameter of the frictional pin 7-10. The frictional pin 7-10 is therefore abutted on the dent 7-6 of the second cylinder 7-4 due to constraining force exerted by the spring 7-12.

Figure 23B:
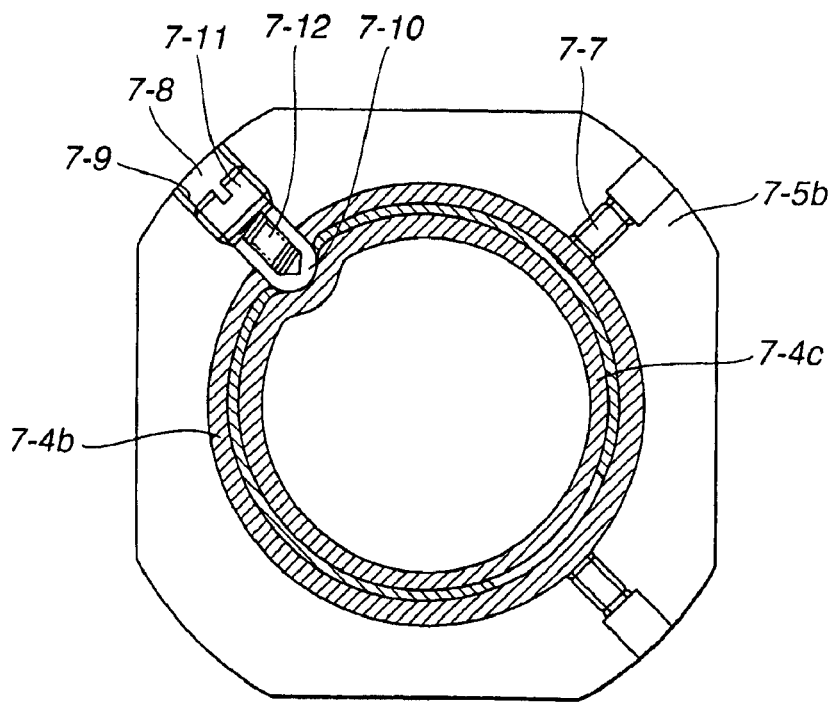
FIG. 23B is a 23B—23B sectional view of the structure shown in FIG. 22A.

Owing to frictional force exerted when the frictional pin abuts on the dent, the first cylinder 7-4a and second cylinder 7-4b can be frictionally locked at any position in the axial direction. The same applies to the second cylinder 7-4b and third cylinder 7-4c as shown in FIG. 23B.

As shown in FIG. 22A, a spirally curled cable 7-13 is inserted in the third cylinder 7-4c. The curled cable 7-13 has connectors attached to the ends thereof, the connectors are joined with a connector formed on the relay printed-circuit board 3-28 locked in the frame 4 and with a connector 7-16 attached to a cable extending from the liquid crystal monitor 7-3. A video signal and power are supplied to the liquid crystal monitor 7-3 over the curled cable 7-13.

Both end parts of the curled cable 7-13 are straight, and an intermediate part thereof is curled. The curled part is stowed in the cylinder 7-4 in its natural state. When the cylinders 7-4 are stretched, the curled part is stretched by a length by which the cylinders 7-4 are stretched. According to the present embodiment, the curled part can be stretched to be approximately three times longer than its natural state.

One end of one of the straight parts is locked in the lower part of the first cylinder 7-4a through a cap 7-14. The other end of the other one of the straight parts is locked in a cable holding mechanism 7-15 located below a first rotating mechanism 7-17. The third crown 7-5c has a cylindrical part 7-18 in the center thereof. A spring 7-19 is mounted on the periphery of the cylindrical part.

Moreover, a shaft 7-21 of a rotating member 7-20 is rotatably inserted into the cylindrical part 7-18 freely. The straight part of the curled cable 7-13 is inserted in the center of the shaft 7-21. A male screw is threaded on the lower part of the shaft 7-21.

A female screw is engaged with the male screw. A locking member 7-22 having a holder thereof slit in order to clamp the straight part of the curled cable 7-13 is attached to the lower part of the rotating member 7-20. The spring 7-19 abuts on a bearer formed on the top of the locking member 7-22. A male screw is threaded on the lower part of the locking member 7-22, and a tightening member 7-23 is engaged with the male screw. By tightening the tightening member 7-23, the inner diameter of the slit of the locking member 7-22 is reduced. Consequently, the cable is locked. Incidentally, a frictional plate 7-24 is interposed between the top of the third crown 7-5c and the bottom of the rotating member 7-20. Frictional force of a certain level is maintained owing to constraining force exerted by the spring 7-19.

FIG. 22B is the top view of the third crown 7-5c. A pin 7-40 is embedded in the bottom of the rotating member 7-20. The pin 7-40 is fitted in a groove 7-41 formed in the top of the third crown 7-5c, thus restricting an angle of rotation of the rotating member 7-20 relative to the third crown 7-5c to a certain angle. This prevents the rotating member 7-20 from rotating infinitely. Consequently, the curled cable 7-13 is prevented from twining.

Moreover, a first block 7-25 that is hollowed is fixed to the top of the rotating member 7-20. A hole through which the curled cable 7-13 passes is formed in the bottom of the first block 7-25. The curled cable 7-13 having passed through the shaft 7-21 of the rotating member 7-20 is introduced into the first block 7-25 through the hole.

Furthermore, an opening is formed in one side surface of the first block 7-24. The curled cable 7-13 is led out of the first block 7-25 through the opening.

As shown in FIG. 21A, one edge of a second rotating mechanism member 7-26 and a panning head 7-29 are fixed to the first block 7-25. The panning head 7-29 includes a holder 7-27 for holding the liquid crystal monitor 7-3, and a second block 7-28 having a connector, with which the connector 7-16 attached to the cable extending from the liquid crystal monitor 7-3 is joined so that the connector 7-16 can be disjoined freely, formed thereon.

The curled cable 7-13 led out of the first block 7-25 enters the internal space of the second block 7-28, and is then led to the connector to be joined with the connector 7-16.

As shown in FIG. 24B, a female screw hole and two slit-like grooves 7-32 are formed in the lower part of the liquid crystal monitor 7-3. A locking screw 7-30 that is a male screw is so formed on the panning head 7-29 as to permit free rotation. The liquid crystal monitor 7-3 is thus fixed to the panning head so that the liquid crystal monitor 7-3 can be unfixed freely. Detent pins 7-31 are located to coincide with the two slit-like grooves. Therefore, the liquid crystal monitor 7-3 will not rotate once fixed.

As shown in FIG. 24C, the liquid crystal monitor 7-3 has a light interceptor panel 7-33 that can be opened or closed freely. The light interceptor panel 7-33 is opened to enter a state indicated with a solid line so that the screen of the monitor can be viewed readily. The light interceptor panel 7-33 is closed to enter a state indicated with an alternate long and two short dashes line, thus protecting the screen of the monitor.

Owing to the foregoing structure, the liquid crystal monitor 7-3 can swivel with the axis of the stretchable pole 7-1 as a center, and can nod relative to the axis.

Now, an example of the configuration of the motor-driven angling unit will be described with reference to FIG. 25 and FIG. 26.

Figure 25:
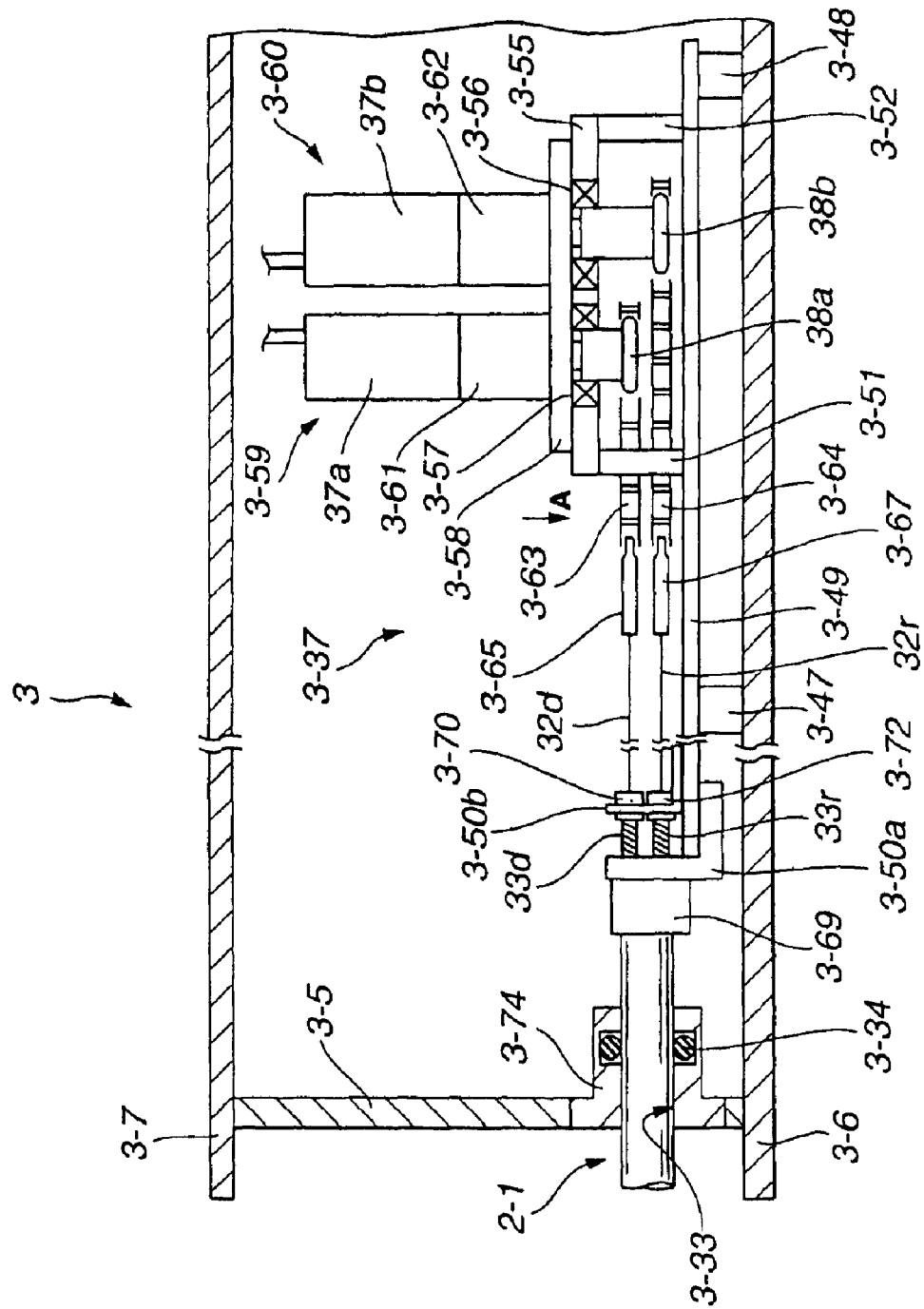
Figure 26:
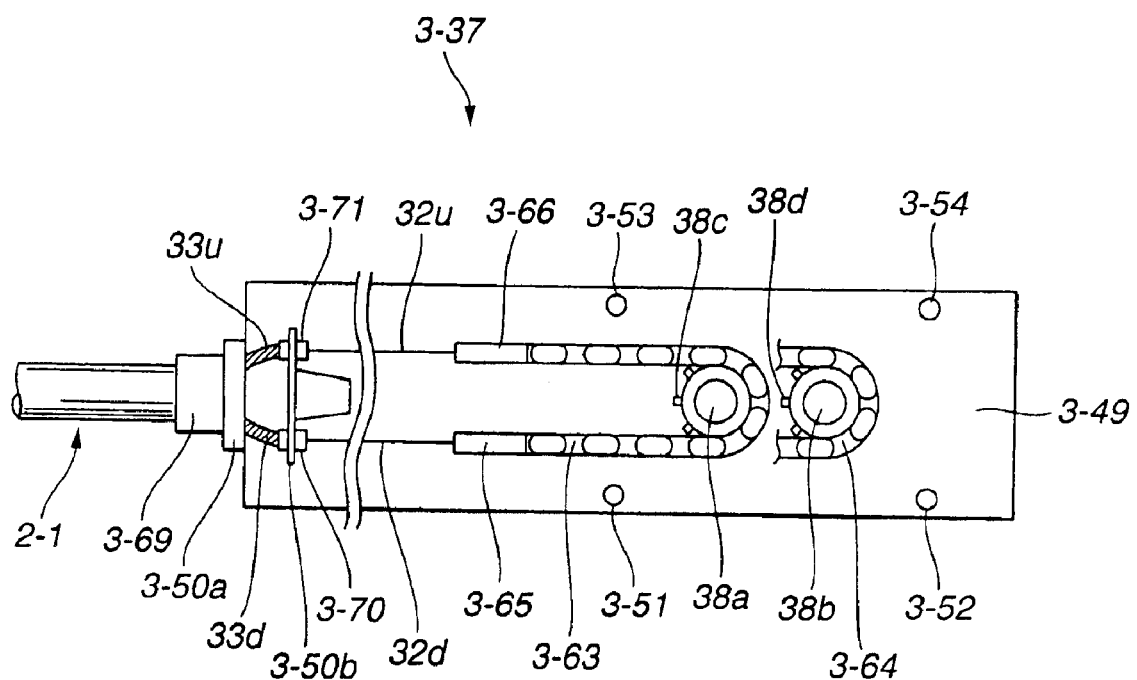

As shown in FIG. 25 and FIG. 26, a base plate 3-49 that is an integral member of the motor-driven angling unit 3-37 is integrated with the first side panel 3-6 with spacers 3-47 and 3-48 between them by performing, for example, screwing or bonding.

The motor-driven angling unit 3-37 consists mainly of a locking member 3-50a, a coil pipe bearer 3-50b, columns 3-51, 3-52, 3-53, and 3-54, and a frame 3-55. The locking member 3-50a and coil pipe bearer 3-50b are located at one end of the motor-driven angling unit 3-37 near the spacer 3-47. The columns 3-51, 3-52, 3-53, and 3-54 are located near the spacer 3-48. The frame 3-55 is secured while being supported by the columns 3-51, 3-52, 3-53, and 3-54.

A motor mount 3-58 is fixed to the frame 3-55 with bearings 3-56 and 3-57 between them. Motor units 3-59 and 3-60 are mounted on the motor mount 3-58. The motor units 3-59 and 3-60 are each composed of a reduction gear 3-61 or 3-62 and a vertical driving motor 37a or a lateral driving motor 37b.

Respectively, the output shafts of the motor units 3-59 and 3-60 are rotatably borne by the bearings 3-56 and 3-57 freely. Sprockets 38a and 38b are attached to the freely rotatable output shafts. Engaging teeth 38c or 38d projecting from the periphery of the sprocket 38a or 38b are engaged with the links of a chain 3-63 or 3-64.

Braces 3-65 and 3-66 are attached to both ends of the chain 3-63. Braces 3-67 and 3-68 are attached to both ends of the chain 3-64. The back ends of the angulation wires 32d, 32u, 32i, and 32r extending from the insertion member 2-1 are led to the braces 3-65, 3-66, 3-67, and 3-68. In the drawing, the brace 3-68 and angulation wire 32i are not shown because they are hidden behind the brace 3-67 and angulation wire 32r respectively.

A rear cap 3-69 attached to the rear end of the insertion member 2-1 is fixed to the locking member 3-50a, whereby the insertion member 2-1 is coupled to the motor-driven angling unit 3-37.

The coil pipes 33d, 33u, 33i, and 33r extending from the end of the insertion member after passing through the insertion member 2-1 pass through the rear cap 3-69 and locking member 3-50a. The coil pipes 33d, 33u, 33i, and 33r are then fixed to the coil pipe bearer 3-50b with coil pipe stoppers 3-70, 3-71, 3-72, and 3-73 attached to the ends thereof.

The angulation wires 32d, 32u, 32i, and 32r having one ends thereof coupled to the braces 3-65, 3-66, 3-37, and 368 run through the coil pipes 33d, 33u, 33l, and 33r respectively. Driving force supplied from the motors 37a and 37b is conveyed over the angulation wires 32d, 32u, 32i, and 32r.

Consequently, an input signal produced responsively to a manipulation performed on the joystick 6-2 is transferred to the control circuit unit 3-38. The control circuit unit 3-38 transfers a driving signal, which is proportional to the input signal, to the motor units 3-59 and 3-60, whereby the motors 37a and 37b incorporated in the motor units 3-59 and 3-60 respectively are driven. The reduction gears 3-61 and 3-62 reduce the number of rotations and intensify torque. Consequently, the output shafts rotate.

This causes the sprockets 38a and 38b mounted on the output shafts to rotate. Consequently, the chains 3-63 and 3-64 engaged with the engaging teeth 38c and 38d of the sprockets 38a and 38b move with the rotation. The angulation wires 32d, 32u, 32i, and 32r coupled to the braces 3-65, 3-66, 3-37, and 3-68 attached to the chains 363 and 3-64 are pushed or pulled. Eventually, the bending section 2-3 bends in the same direction as a direction in which a pulled pair of angulation wires out of the angulation wires 32d, 32u, 32i, and 32r is bent.

A passage member 3-74 having a notch 3-33 is fixed to the cylindrical member 3-5 using, for example, an adhesive. The insertion member 2-1 is passed through the passage member 3-74. A packing 3-34 for preventing invasion of water and dust is attached to the inner wall of the notch 3-33 of the passage member 3-74. Namely, the packing 3-34 prevents invasion of water or dust from outside into the sealed space in the drum 3.

Moreover, the motor units 3-59 and 3-60, sprockets 38a and 38b, chains 3-63 and 3-64, angulation wires 32d, 32u, 32l, and 32r, and coil pipes 33d, 33u, 33l, and 33r are grouped into two groups. Namely, one group is responsible for vertical angling, while the other group is responsible for lateral angling. When the motors must be controlled more precisely, an encoder is included in the motor units.

An operation to be exerted by the endoscope system 1 having the foregoing configuration will be described below.

During preservation or transportation, or before use, the insertion member 2-1 included in the endoscope system 1 is wound up about the cylindrical member 3-5 of the drum 3.

When preparations are made for an inspection, that is, when the endoscope system 1 is set up, the drum 3 is rotated in a predetermined direction in order to draw out the insertion member 2-1. At this time, according to the present embodiment, the light guide 21 running through the endoscope 2 is led to the light source unit 3-36, and the signal line 26 running through the endoscope 2 is led to the CCU 3-39. The job of leading the light guide and signal line therefore need not be performed on this stage.

For angling the endoscope 2, the joystick 6-2 is manipulated. This causes the control circuit unit 3-38 to control rotation of the motors 37a and 37b.

After an inspection is completed, the drum 3 is rotated in a direction opposite to the foregoing direction in order to wind the insertion member 2-1 about the periphery of the cylindrical member 3-5. This brings the endoscope system 1 to a preserved state.

In the aforesaid present embodiment, peripheral equipment including at least the motor-driven angling unit 3-37, power unit 4-1, control circuit unit 3-38, CCU 3-39, and light source unit 3-36 is incorporated in the drum 3. The motor-driven angling unit 3-37 includes a driving source for driving a driving mechanism that drives the bending section 2-3 using a motor to bend the bending section. The drum 3 is rotatably put in the stowage case 8 freely. The endoscope system 1 is thus configured. Consequently, the elongated insertion member of the endoscope can be wound up about the drum, and the endoscope and peripheral equipment can be stowed compactly. Eventually, the endoscope system can be readily preserved and transported.

Moreover, the bearing members 4-12 are fixed to the outer edge of one side panel of the cylindrical drum 3, which is concentric to the drum 3, away from the center of rotation of the drum 3. The flange 4-10 serving as an annular guide rail is fixed to the frame closely opposed to the side panel. The flange 4-10 is engaged with the bearing members 4-12. This results in a bearing structure for rotatably bearing the drum 3 freely along the ring of the flange. Despite the simple structure, the drum 3 can be borne to be freely rotatable. Compared with when a structure formed near the center of rotation is rotatably used to bear the drum freely, the part of the drum near the center of rotation will not protrude and wax, and the drum can be designed compactly.

Moreover, the peripheries of the bearing members 4-12 are engaged with the periphery of the guide rail. Herein, the peripheries of the bearing members 4-12 or the periphery of the guide rail are shaped as concave parts such as V-shaped grooves. The periphery of the guide rail or the peripheries of the bearing members 4-12 is shaped as a convex part such as the V-shaped part 4-11. Even when the case 8 is placed lengthwise or sideways, or tilted in any direction other than one specific direction, the bearing members and the guide rail remain engaged with each other, and the drum can be rotated smoothly.

Moreover, since ball bearings are adopted as the bearing members 4-12, smooth rotation can be ensured.

Moreover, a space created near the center of rotation inside the bearing structure can be utilized for placing a connecting mechanism or the like that transfers electric signals between electric equipment located inside the drum 3 and electric equipment located outside it. This results in the compact drum and contributes to the compact design of the endoscope system.

The above description has been made on the assumption that the bearing members 4-12 are fixed to the drum and the guide rail is fixed to the frame. On the contrary, the guide rail may be fixed to the drum 3 and the bearing members 4-12 may be fixed to the frame. Moreover, a slip ring may be adopted as the connecting mechanism that transfers electric signals.

Furthermore, the gear 3-18 is formed on the periphery of the outer edge of one of the side panels of the drum 3 having the cylindrical member 3-5 about which the insertion member 2-1 is wound. The gear 4-43 is engaged with the gear 3-18. The shaft 4-13 is opposed to the cylindrical surface of the cylindrical member 3-5, and rotatably supported by the frame members freely. The moving member 4-16 has the female screw threaded thereon and engaged with the male screw 4-15 threaded on the periphery of the shaft 4-13, and moves in the axial direction of the shaft 4-13 with the rotation of the shaft 4-13. The lever 4-21 coupled to the variable resistance terminal of the sliding variable resistor 4-20 can freely move with the movement of the moving member 4-16 over a range on the cylindrical member 3-5 over which the insertion member 2-1 can be wound about the cylindrical member 3-5. Owing to this structure, a length by which the insertion member 2-1 is wound about the cylindrical member 3-5 can be detected. Otherwise, a length of a portion of the insertion member 2-1 that is not wound can be calculated by subtracting the length by which the insertion member 2-1 is wound from the overall length of the insertion member 2-1. Otherwise, a length by which the insertion member 2-1 is drawn out can be detected.

Talking of detection of the length, since the lever 4-21 attached to the sliding variable resistor 4-20 is mechanically moved, the length can be detected irrespective of whether the power supply is turned on or off. The timing of turning on or off the power supply is not limited to the timing that the insertion member is wound up, or more strictly, wound to the greatest extent. For example, when the insertion member 2-1 is drawn out a little, if the power supply is turned on, information of a length can be detected highly precisely. This overcomes the inconvenience of the related art that measurement can be performed only when the power supply is on.

Moreover, if a battery is used to drive the endoscope system, the battery may be exhausted or the power supply may be temporarily turned off for saving the battery. Even in this case, the length information can be maintained. Even if an attempt is made to thrust out the insertion member 2-1 with the power supply turned off, a measured value will not be inaccurate. Thus, the endoscope system is user-friendly.

Moreover, if necessary, electric information acquired at the sliding variable resistor 4-20 may be utilized for control of angling.

The frame 4 encloses the drum 3 about which the insertion member 2-1 included in the industrial endoscope 2 can be wound freely, and rotatably holds the drum 3 freely. The plate-like shock absorbers 8-1b are placed on the side surfaces of the frame 4 that are closely opposed to the side surfaces of the case body 8-4 serving as a housing member in which the frame 4 is stowed. The upper ends and lower ends of the shock absorbers 8-1b abut on the receiving surfaces 8-16 formed as integral parts of the case body 8-4 and the bearers 4-27 respectively. Shocks such as vibrations to be applied in a vertical direction parallel to the side surfaces of the case body during transportation or the like are absorbed by the shock absorbers 8-1b. The contents of the case body 8-4 can be protected efficiently. Besides, compared with when the shock absorbers are placed on the surfaces of the case body 8-4 that undergo shocks, that is, the top and bottom of the case body 8-4, the case 8 can be designed more compactly.

Moreover, according to the present embodiment, the shock absorbers are placed like vertically elongated plates. This leads to the reliable durability against shocks.

Referring to FIG. 4 and others, the upper ends of the shock absorbers 8-1b abut on the receiving surfaces 8-16 formed as integral parts of the case body 8-4, and the lower ends thereof abut on the bearers 4-27 fixed to the frame. Thus, the frame is held elastically. Alternatively, the upper ends of the shock absorbers 8-1b may be abutted on the bearers 4-27, and the lower ends thereof may be abutted on the receiving surfaces 8-16.

Now, the electric configuration of a major portion of the aforesaid present embodiment will be described briefly.

Figure 27A:
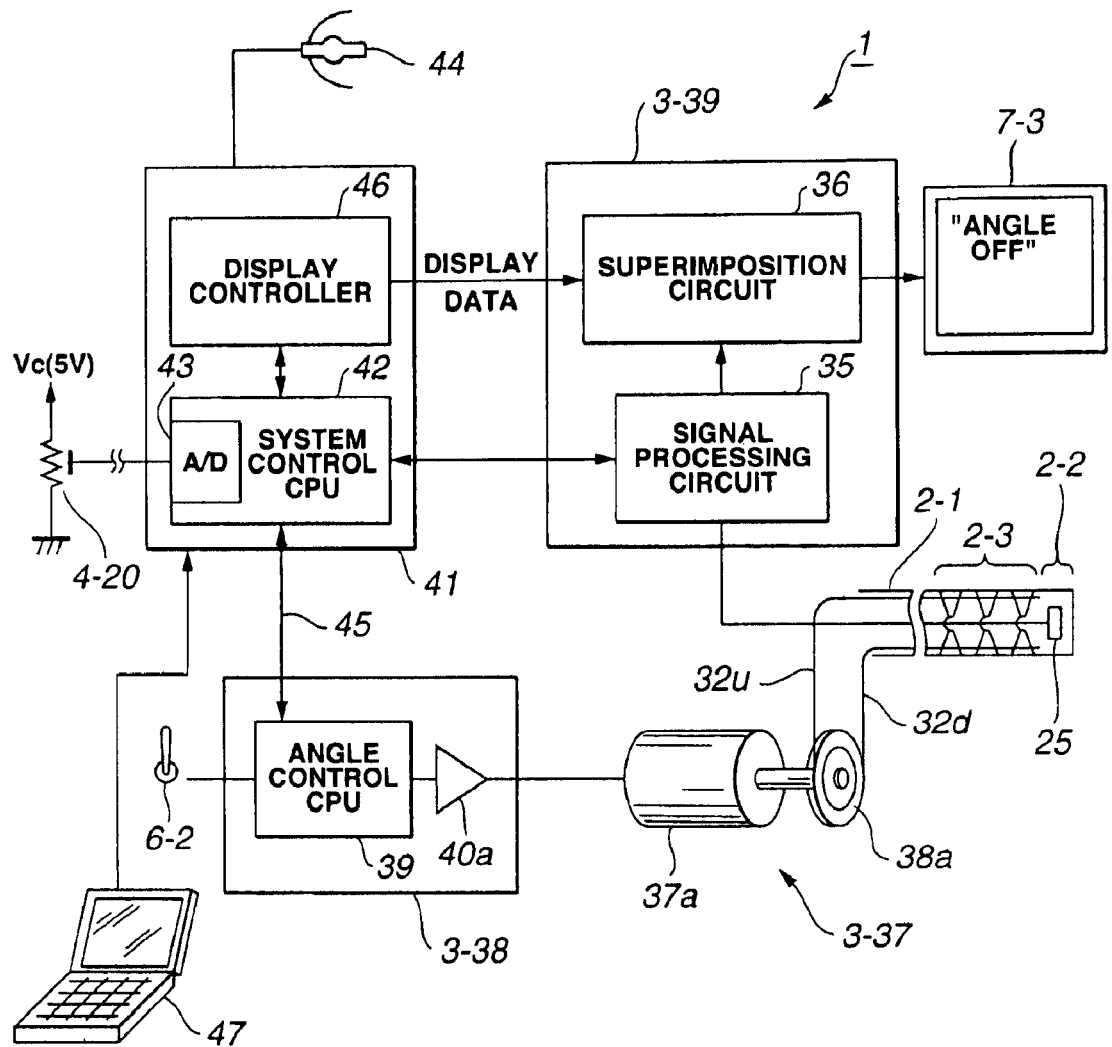
FIG. 27A shows the outline configuration of the electric system employed in an endoscope system.
Figure 27B:
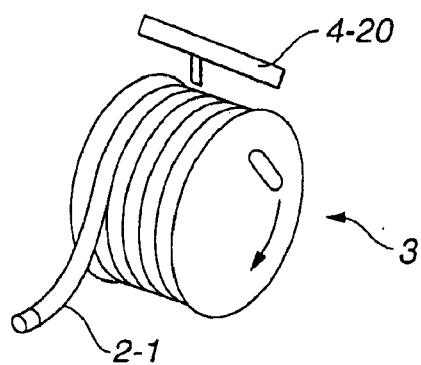
FIG. 27B shows an insertion member extending from a drum.

The CCD 25 is, as shown in FIG. 27A, incorporated in the tip of the insertion member 2-1 that is wound about the drum as shown in FIG. 27B. An output signal of the CCD 25 is transferred to a signal processing circuit 35 incorporated in the CCU 3-39 over a cable 26. A standard video signal is then produced, and transferred to the liquid crystal monitor 7-3 via a superimposition circuit 36.

Moreover, the angulation wires 32u and 32d used to bend the bending section 2-3 vertically are coupled to the sprocket 38a of the vertical driving motor 37a included in the motor-driven angling unit 3-37. When the joystick 6-2 is tilted, the motor 37a is driven to rotate by an angle control CPU 39 and a driving amplifier 40a included in the motor-driven angling control circuit unit 3-38. Consequently, the bending section 2-3 is bent upwards or downwards.

FIG. 27A does not show the angulation wires 32l and 32r to be used to bend the bending section laterally. When the joystick 6-2 is tilted laterally, the lateral driving motor is driven to rotate using a driving amplifier that is not shown. Consequently, the angulation wires 32l and 32r are driven.

Moreover, both the terminals of the sliding variable resistor 4-20 for detecting a wound state, that is, a length by which the insertion member 2-1 is wound about the drum 3 or the number of rotations are connected to a +5V power terminal Vc and a ground respectively. The voltage developed at the variable resistance terminal thereof is communicated to a system control CPU 42 mounted on a system printed-circuit board 41 via an A/D converter 43.

Figures 28, 29:
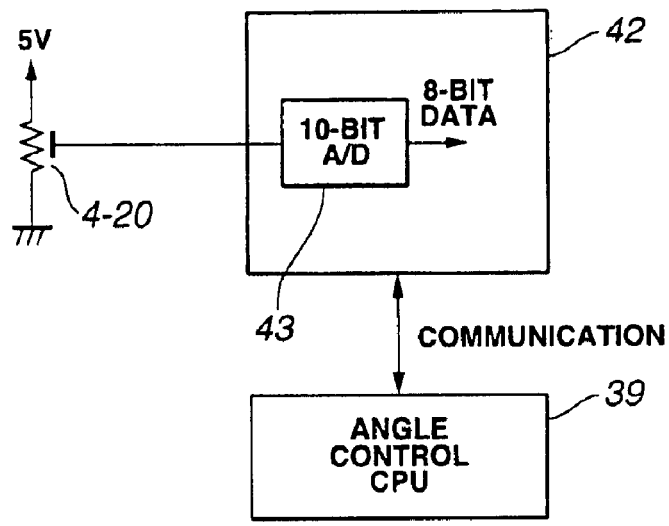

FIG. 28 shows the system control CPU 42 and angle control CPU 39 in enlargement. For example, the A/D converter 43 incorporated in the system control CPU 42 is an A/D conversion circuit that treats ten bits. Eight bits out of the ten bits are used to detect the wound state.

Referring to FIG. 29, the wound state of the insertion member and a practical example of digitized data will be described below. As seen from the table of FIG. 29, an output voltage developed at the variable resistance terminal assumes the highest level when the insertion member is wound up. The voltage level decreases as the insertion member is drawn out. The voltage level is digitized by the A/D converter 43, and communicated to the system control CPU 42.

The system control CPU 42 receives analog data and determines a threshold for digital data that results from A/D conversion, that is, the number of rotations of the drum. The state of the insertion member 2-1 is determined based on the threshold. For example, when the detected number of rotations falls within one of a range equal to or larger than a certain threshold and a range smaller than the threshold, it is judged that the insertion member 2-1 remains stowed in the case. When the detected number of rotations falls within the other range, it is judged that the insertion member 2-1 is fully drawn out from the case. Based on the result of judgment, supply of power to peripheral or electric equipment is started or stopped or movements are enabled or disabled.

To be more specific, the system control CPU 42 employed in the present embodiment gives control to enable or disable angling according to the state of the insertion member 2-1. As described in conjunction with a variant later, the system printed-circuit board 41 may be activated in order to control the on-off switching of the light source lamp 44.

An example of setting a threshold based on which angling is enabled or disabled will be described with reference to FIG. 30. According to the table of FIG. 30, the number of rotations by which the drum 3 is rotated in order to wind the insertion member about the drum varies depending on whether the insertion member 2-1 is of a type having a length of 3.5 m or a type having a length of 9.5 m. The sliding variable resistor 4-20 detects the number of rotations according to the type of insertion member. Digital data sent from the A/D converter 43 therefore differs between the types of insertion member. Consequently, a range of digital data leading to the judgment that angle controlling is enabled and a range of digital data leading to the judgment that angle controlling is disabled differ between the types of insertion member.

Specifically, for the type of insertion member having the length of 3.5 m, a threshold is set to digital data of 54. When the detected number of rotations falls within a range of 0 to 53, angle controlling is enabled. When the detected number of rotations falls within a range of 54 to 255, angle controlling is disabled. In contrast, for the type of insertion member having the length of 9.5 m, a threshold is set to 61. When the detected number of rotations falls within a range of 0 to 60, angle controlling is enabled. When the detected number of rotations falls within a range of 61 to 255, angle controlling is disabled.

For enabling or disabling angle controlling, the system control CPU 42 is, as shown in FIG. 27A, connected to the angle control CPU 39 over a communication line 45. If it is judged based on digital data that the insertion member 2-1 is wound up about the periphery of the drum 3 and stowed in the case, angle controlling is disabled. In contrast, if it is judged that the insertion member 2-1 is drawn out to some extent, angle controlling is enabled.

Moreover, display is controlled based on the above judgment. The system control CPU is therefore connected to a display controller 46. The display controller 46 uses the superimposition circuit 36 to control display data to be presented on the liquid crystal monitor 7-3.

The threshold can be changed at a personal computer 47 placed externally.

An operation to be exerted by the present embodiment will be described with reference to FIG. 31.

When the power supply is turned on, the system power supply on the system printed-circuit board 41 is turned on at step S1.

At step S2, the state of the tip of the insertion member 2-1 is sensed based on data received from a number-of-drum rotations sensing mechanism. Specifically, a voltage detected at the sliding variable resistor 4-20 is digitized by the A/D converter 43, and transferred to the system control CPU 42. The system control CPU 42 senses the state of the tip of the insertion member 2-1 according to the received value.

At step S3, it is judged from the state of the tip of the insertion member 2-1 whether the insertion member 2-1 is drawn out from the drum 3. If the insertion member 2-1 is not drawn out, control is returned to step S2. If the insertion member is drawn out, control is passed to step S4. At step S4, Angle Controlling Disabled is displayed. Before this message is displayed, the CCU 3-39 is activated.

At step S5, the number of rotations of the drum is sensed based on data sent from the number-of-drum rotations sensing mechanism. Specifically, the number of rotations by which the drum 3 is rotated in order to wind the insertion member 2-1 about the drum is sensed.

At step S6, it is judged whether the number of rotations of the drum falls below a threshold n that is set to a right value and represents the number of turns by which the insertion member is wound (see FIG. 30 that lists digital data). If the number of rotations of the drum does not fall below n, control is returned to step S5. If the number of rotations falls below n, angle controlling is enabled in order to accept a request for angling the insertion member at step S7. At step S8, Angle Controlling Disabled is deleted or non-displayed. The processing then terminates.

Figure 31:
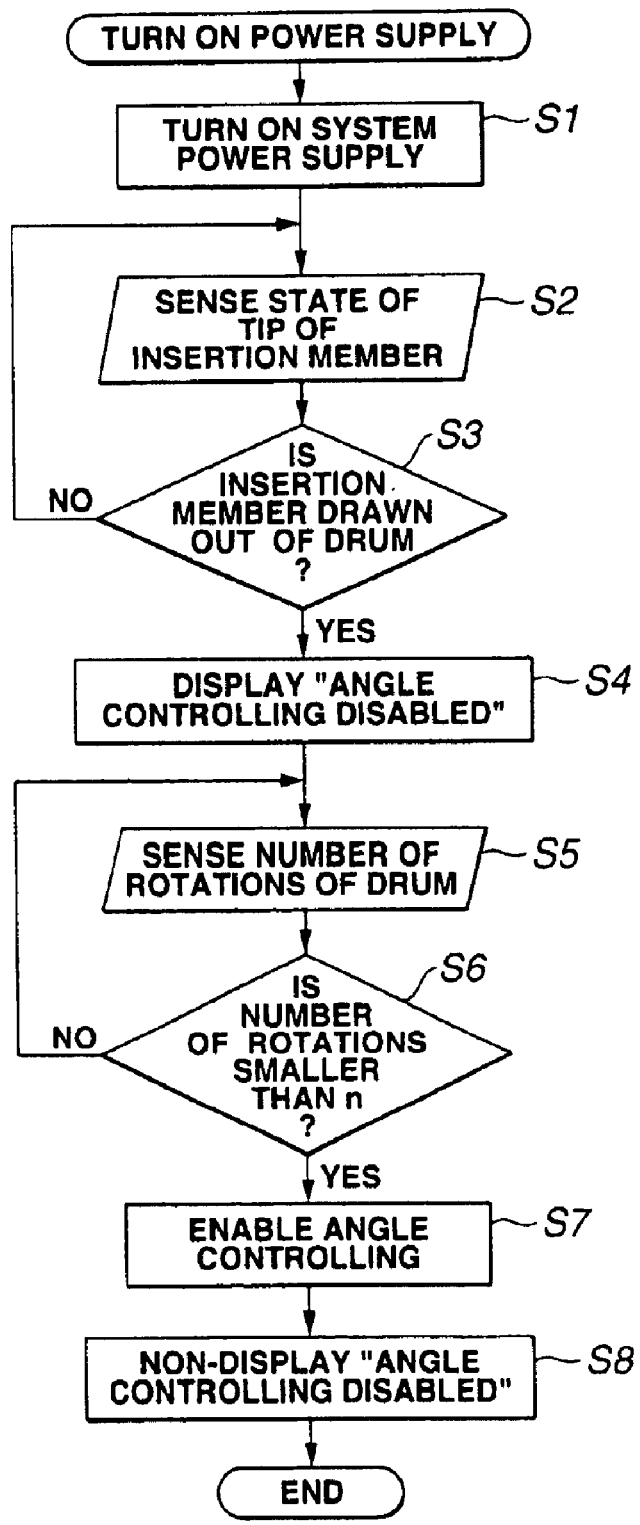

In the flowchart of FIG. 31, step S1 may be succeeded by step S4, and step S4 may be succeeded by step S2. In this case, when the system power supply is turned on, Angle Controlling Disabled is displayed. Thereafter, the state of the insertion member 2-1 is judged. If the number of rotations falls below n, angle controlling is enabled and Angle Controlling Disabled is non-displayed.

As mentioned above, according to the present embodiment, when the insertion member 2-1 enters a drawn state in which the insertion member 2-1 is drawn out of the drum 3 to some extent, if a request for angling the insertion member is accepted, angle controlling is enabled. When the insertion member 2-1 enters a wound state in which the insertion member 2-1 is wound about the drum 3 to a considerable extent, if a request for angling the insertion member is accepted, an excess load may be imposed on the angulation wires and motors. In this case, angle controlling is disabled in order not to accept the request for angling the insertion member. Consequently, the angulation wires and motors are protected from incurring an excess load. Moreover, if the insertion member enters the state that encourages acceptance of the request for angling the insertion member, angle controlling is automatically enabled. This would be found user-friendly.

Moreover, if the power supply for the motor 37a or motor-driven angling control circuit unit 3-38 is not turned on unless the insertion member enters the state encouraging acceptance of a request for angling the insertion member (step S7 in FIG. 31), power can be saved.

In the flowchart of FIG. 31, step S2 and step S3 may be omitted.

Figure 32:
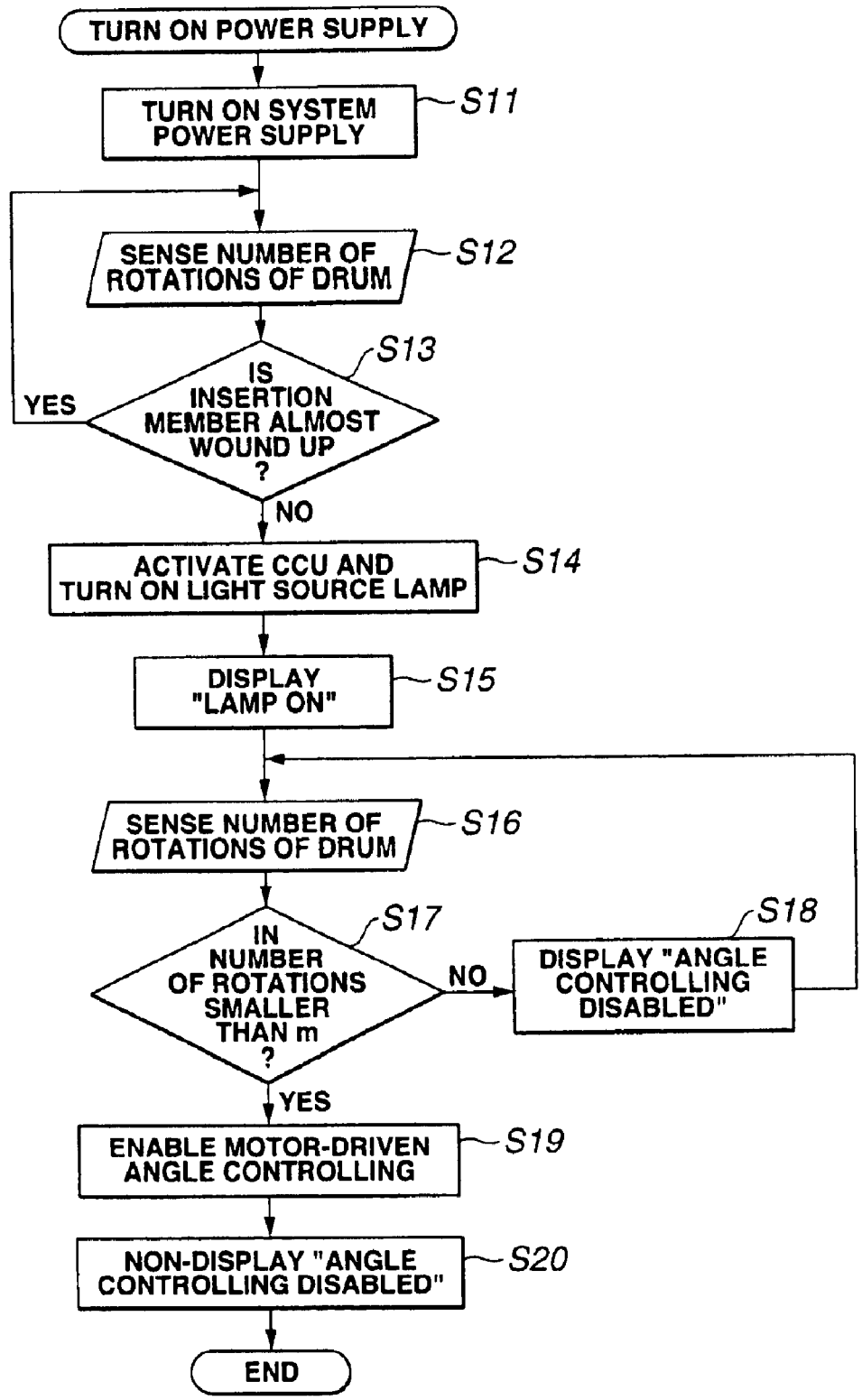

Referring to FIG. 32, when the system power supply is turned on at step S11, the number-of-drum rotations sensing mechanism senses the state of the insertion member 2-1 wound about the drum 3. At step S13, it is judged from a first threshold whether the insertion member 2-1 is nearly wound up.

If so, control is returned to step S12. In contrast, if the insertion member 2-1 is drawn out to a greater extent than an extent indicated with the first threshold, the CCU 3-39 is activated and the light source lamp 44 is turned on at step S14. At step S15, Lamp On is displayed on the monitor 7-3. Alternatively, an indication indicating that the CCU 3-39 and CCD 25 are activated may be displayed.

At step S16, the number of rotations of the drum sensed by the number-of-drum rotations sensing mechanism is communicated. Based on the information, it is judged at step S17 whether the number of turns by which the insertion member is wound falls below a second threshold m (which signifies that the insertion member is a little drawn out rather than it is nearly wound up).

If not, the insertion member is considerably wound or enters a state that discourages acceptance of a request for angling the insertion member. In this case, Angle Controlling Disabled is displayed at step S18, and control is returned to step S16.

If the number of turns falls below m, motor-driven angle controlling is enabled at step S19. Power is supplied to the motor-driven angling control circuit unit 3-38 and motor-driven angling unit 3-37, whereby a request for motor-driven angling can be accepted. At step S20, Angle Controlling Disabled is non-displayed, and an indication indicating that the request for motor-driven angling can be accepted is displayed. Alternatively, Angle Controlling Enabled may be displayed or temporarily displayed at the time of transition from enabling angle controlling to disabling angle controlling or vice versa.

Referring to FIG. 32, when the system power supply is turned on at step S11, even if the CCU 3-39 is activated, Lamp Off may be displayed on the monitor 7-3 in order to indicate that the light source lamp 44 is off.

The foregoing variant provides the advantage described below.

The system control CPU 42 judges from the number of rotations of the drum 3 whether the insertion member 2-1 enters a state that permits proper observation, and controls whether the peripheral (electric) equipment should be activated or inactivated.

If the insertion member has not entered the state permitting proper observation, the system control CPU 42 does not supply power to the peripheral equipment, or temporarily freezes an activation instruction. Thus, efforts are made to minimize power consumption, to extend a service life, or to prevent application of an excess load. Moreover, whether the peripheral equipment is activated or inactivated is indicated on the monitor 7-3. This is effective in preventing a user from incorrectly activating the peripheral equipment.

(Second Embodiment)

Next, a second embodiment of the present invention will be described with reference to FIG. 33 and FIGS. 34A and 34B. The present embodiment is identical to the first embodiment in terms of the system configuration. However, an operation program employed in the present embodiment is different from that in the first embodiment. Whether the light source lamp 44 should be activated or inactivated is controlled based on the wound state of the insertion member 2-1.

Specifically, in the endoscope system 1 of the first embodiment, when the insertion member 2-1 is nearly wound up about the drum 3 and stowed in the housing, analog data acquired at the sliding variable resistor 4-20 and transferred from the number-of-drum rotations sensing mechanism to the system control CPU 42 falls within a range leading to the judgment that the light source lamp 44 should be inactivated. The system control CPU 42 temporarily freezes issuance of an activation instruction to the light source lamp 44 and supply of power thereto. The light source lamp 44 is then inactivated, that is, put off.

Supposing the insertion member 2-1 is drawn out from the housing, unless the analog data acquired at the sliding variable resistor 4-20 exceeds a threshold from which it is judged whether the light source lamp 44 should be inactivated, the light source lamp 44 remains inactivated.

In contrast, when the insertion member is drawn out from the housing by a length large enough to achieve observation properly, the number of rotations of the drum exceeds the threshold from which the system control CPU 42 judges that the light source lamp 44 should be inactivated. It is therefore judged from the number of rotations that the light source lamp 44 may be activated. The system control CPU 42 issues an activation enabling instruction to the light source lamp 44 and allows supply of power to the light source lamp 44. The light source lamp 44 is then lit. Illumination light is then propagated over the light guide 21 (see FIG. 2), which runs through the insertion member 2-1, and supplied to the imaging system.

FIG. 33 shows an example of a threshold from which it is judged whether the light source lamp 44 should be activated or inactivated. Even this table of FIG. 33 lists different thresholds in relation to the type having the length of 3.5 m and the type having the length of 9.5 m respectively.

As shown in FIG. 34A, when the power switch is turned on, the system power supply is turned on at step S21. At step S22, the state of the tip of the insertion member 2-1 is sensed based on data sent from the number-of-rotations sensing mechanism.

At step S23, it is judged from the state of the tip whether the insertion member is drawn out of the drum 3. If not, control is returned to step S22. If it is judged from the state of the tip that the insertion member is drawn out of the drum 3, the light source lamp 44 is turned on at step S24. The processing is terminated. Now, an endoscopic inspection can be carried out.

FIG. 34B describes actions to be performed when the power switch is turned off after the endoscopic inspection is performed with the light source lamp 44 turned on.

When the power switch is turned off, the power supply of the light source lamp 44 is turned off at step S25. At step S26, the system power supply is turned off. Thus, turning off power supplies is terminated.

The present embodiment provides the advantage described below.

When the insertion member 2-1 is wound up about the drum 3 and stowed in the housing, the system control CPU 42 judges from the number of rotations of the drum that the insertion member has not entered the state suitable for observation. The system control CPU 42 therefore does not supply power to the light source lamp 44.

Consequently, even when the power supply of the endoscope system 1 is turned on, if the insertion member has not entered the state permitting supply of illumination light, the light source lamp 44 is inactivated. This is effective in reducing power consumption.

Moreover, unless the endoscope system is used for observation, the light source lamp 44 is put off. The service life of the light source lamp 44 is therefore extended.

(Third Embodiment)

Figure 35:
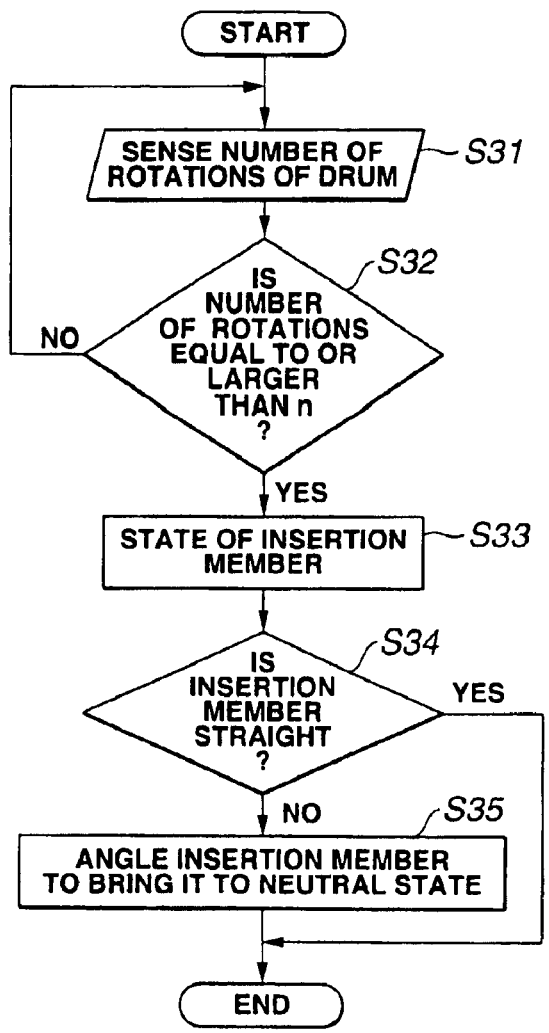
FIG. 35 is a flowchart describing actions to be performed in a third embodiment of the present invention.

A third embodiment of the present invention will be described with reference to FIG. 35. The present invention is identical to the first embodiment in terms of the system configuration. Action programs employed in the present embodiment are partly different from those employed in the first embodiment.

Specifically, in the endoscope system 1 of the first embodiment, when the insertion member 2-1 is wound about the drum 3 at the completion of an inspection, the motor-driven angling control circuit unit 3-38 issues a bending section locking instruction to the motor 37a. The bending section locking instruction instructs that the bending section should be held bent. When an attempt is made to stow the insertion member with the bending section 2-3 held bent, the number of rotations of the drum 3 acquired at the sliding variable resistor 4-20 exceeds the threshold from which it is judged whether motor-driven angling is enabled or disabled. When the number of rotations falls within the range leading to the judgement that motor-driven angling should be disabled, the system control CPU 42 issues an instruction, which instructs that motor-driven angling should be disabled, to the motor-driven angling drive circuit unit 3-38.

In response to the instruction, the motor-driven angling drive circuit unit 3-38 releases the bending section locking instruction which instructs that the bending section should be held bent, and controls the motor 37a so as to bring the bending section 2-3 back to a neutral state.

The action of bringing the bending section 2-3 back to the neutral state is not limited to a special state in which the motor-driven bending section should be locked. The action is also performed when the bending section is used normally.

Next, the action will be described with reference to FIG. 35.

When it is started to wind the insertion member about the drum 3, the number-of-drum rotations sensing mechanism communicates the sensed number of rotations of the drum to the system control CPU 42.

At step S32, it is judged from the information whether the insertion member 2-1 is wound about the drum 3 by n turns or more. If the number of turns by which the insertion member 2-1 is wound is smaller than n, control is returned to step S21. If the number of turns is equal to or larger than n, the information of an angled state is acquired at a potentiometer, which is not shown, attached to the motor 37a or the like.

It is judged from the information of the angled state whether the insertion member 2-1 lies straight. If the insertion member 2-1 does not lie straight, angling is instructed in order to straighten the insertion member at step S35. Consequently, the insertion member 2-1 is straightened or brought to a neutral state. The processing is then terminated.

If it is judged at step S34 that the insertion member lies straight, the insertion member is not angled. The processing is terminated. Thereafter, the insertion member 2-1 is wound about the drum 3, and the lid 8-5 is closed. The job of winding is then terminated.

The present embodiment provides the advantage described below.

The insertion member 2-1 is wound about the drum 3. When it is intended to nearly wind up the insertion member 2-1 about the drum 3 and thus stow it in the housing, before the insertion member 2-1 is nearly wound up about the drum 3, the bending section 2-3 is brought back to the neutral state. Consequently, excess tension to be applied to the angulation wires can be suppressed, and deterioration of durability can be alleviated. Incidentally, the excess tension is applied when the insertion member 2-1 is wound about the drum while the bending section is locked to be held bent or the bending section is bent normally.

(Fourth Embodiment)

Next, a fourth embodiment of the present invention will be described below. The present embodiment is identical to the first embodiment in terms of the appearance and system configuration. Action programs employed in the present embodiment are partly different from those in the first embodiment.

In the endoscope system 1 of the first embodiment, assume that the insertion member 2-1 is nearly wound up about the drum 3 and stowed in the housing. Analog data acquired at the sliding variable resistor 4-20 and transferred from the number-of-drum rotations sensing mechanism to the system control CPU 42 falls within a range leading to the judgment that the CCU 3-39 should be inactivated. Consequently, issuance of an activation instruction from the system control CPU 42 to the CCU 3-39 and supply of power to the CCU 3-39 are temporarily frozen. The CCU 3-39 is thus inactivated.

Even when the insertion member 2-1 is drawn out of the housing, unless the analog data acquired at the sliding variable resistor 4-20 exceeds the threshold from which it is judged whether the CCU 3-39 should be inactivated, the CCU 3-39 remains inactivated.

In contrast, when the insertion member 2-1 is drawn out of the housing by a length large enough to achieve observation, the number of rotations of the drum 3 exceeds the threshold from which the system control CPU 42 judges whether the CCU 3-39 should be inactivated. The system control CPU 42 then judges from the number of rotations that the CCU may be activated. The system control CPU 42 issues an activation enabling instruction to the CCU 3-39 and allows supply of power to the CCU 3-39. Consequently, a view image is displayed on the monitor owing to the abilities of the CCU 3-39.

The present embodiment provides the advantage described below.

When the insertion member 2-1 is wound up about the drum 3 and stowed in the housing, the system control CPU 42 judges from the number of rotations of the drum that the state of the insertion member is unsuitable for observation. The system control CPU 42 therefore does not allow supply of power to the CCU 3-39.

Consequently, even when the power supply of the endoscope system 1 is turned on, unless observation is not enabled, the CCU 3-39 is inactivated. This is advantageous to reduction of power consumption.

(Fifth Embodiment)

Next, a fifth embodiment of the present invention will be described below. The present embodiment is identical to the first embodiment in terms of the appearance and system configuration. Action programs employed in the present embodiment are partly different from those in the first embodiment.

In the endoscope system 1 of the first embodiment, software is used to set an angle of bending to a maximum value instead of a mechanical stopper that is not shown. The mechanical stopper is included in a wire pulling mechanism for setting an angle of bending to a maximum value. Specifically, the system control CPU 42 issues an instruction, which instructs bending of the bending section 2-3 to the greatest extent, to the motor-driven angling control circuit unit 3-38. The motor-driven angling control circuit unit 3-38 gives control to pull the angulation wires until the angle of bending becomes the maximum value determined by software.

In this case, a mechanical stopper is located at a position enabling a magnitude of traction, which is larger than a magnitude of traction exerted for the purpose of bending the bending section by the maximum angle of bending, to be exerted in pulling the angulation wires.

The present embodiment provides the advantage described below.

Software is substituted for a mechanical stopper in order to set an angle of bending by which the bending section 2-3 is bent to a maximum angle of bending. This obviates the necessity of the job of attaching and positioning the mechanical stopper whose position must be varied depending on the length of an insertion member. Consequently, the cost of the endoscope system can be reduced.

Moreover, a mechanical stopper is located at a position enabling a magnitude of traction, which is larger than a magnitude of traction exerted for the purpose of bending the bending section by the maximum angle of bending determined by software, to be exerted in pulling the angulation wires. The mechanical stopper can be utilized as an excessive bending prevention mechanism.

(Sixth Embodiment)

Next, a sixth embodiment of the present invention will be described below. The present embodiment is identical to the first embodiment in terms of the appearance and system configuration. Action programs employed in the present embodiment are partly different from those in the first embodiment.

In the endoscope system 1 of the first embodiment, the system control CPU 42 learns a length, by which the insertion member 2-1 is drawn out of the housing, by analyzing analog data acquired at the sliding variable resistor 4-20 and transferred from the number-of-drum rotations sensing mechanism.

The system control CPU 42 sets a maximum angle of bending in relation to a length by which the insertion member 2-1 is drawn out, and transmits an angling instruction to the motor-driven angling drive circuit unit 3-38. In response to the angling instruction, the motor-driven angling control circuit unit 3-38 controls the motor 37a or the like according to the maximum angle of bending set in relation to the length by which the insertion member 2-1 is drawn out. The motor-driven angling control circuit unit 3-38 thus changes a magnitude of traction to be exerted in pulling the angulation wires. The job of setting the maximum angle of bending may be assigned to the motor-driven angling control circuit unit 3-38 that receives the number of rotations of the drum.

The present embodiment provides the advantage described below.

Think of a case where the insertion member 2-1 is fully drawn out of the housing and straightened and a case where the insertion member 2-1 is drawn out halfway and has a portion thereof still wound about the drum. In the cases, even if the same bending-related information is given to the motor-driven angling control circuit unit 3-38, an angle of bending differs because of friction between channels contained in the insertion member 2-1. When the insertion member 2-1 has a portion thereof still wound about the drum 3, the angle of bending is smaller than that attained when the insertion member is straightened.

Even when the insertion member 2-1 is wound about the drum 3 to some extent, if a magnitude of traction to be exerted in pulling the wires is increased based on a length by which the insertion member 2-1 is drawn out, the same angle of bending as the angle of bending attained when the insertion member is straightened can be attained. Herein, the length by which the insertion member 2-1 is drawn out can be inferred from the number of rotations of the drum.

In contrast, even when it is judged from the number of rotations of the drum that angling may be enabled, if the number of turns by which the insertion member 2-1 is wound about the drum 3 exceeds a certain value, the maximum angle of bending is reduced in order to prevent the angulation wires from being excessively tensioned. This is effective in suppressing deterioration of durability of the angulation wires.

According to the above description, when the main power supply is turned on, the system power supply is turned on and whether the electric equipment should be activated or inactivated is controlled based on the state of the insertion member 2-1 wound about the drum 3. Alternatively, as long as the system power is on, whether the electric equipment should activated or inactivated may be always controlled based on the state of the insertion member 2-1 wound about the drum 3.

For example, once the insertion member 2-1 is fully drawn out of the drum 3, motor-driven angling is enabled and the light source lamp 44 is turned on. Thereafter, when an inspection of a certain region is performed and succeeded by another inspection, if the insertion member once drawn out is taken up again, the light source lamp 44 may be automatically turned off according to information given from the number-of-drum rotations sensing mechanism. If the insertion member is drawn out for still another inspection, the light source lamp 44 may be automatically turned on.

(Seventh Embodiment)

Figure 36:
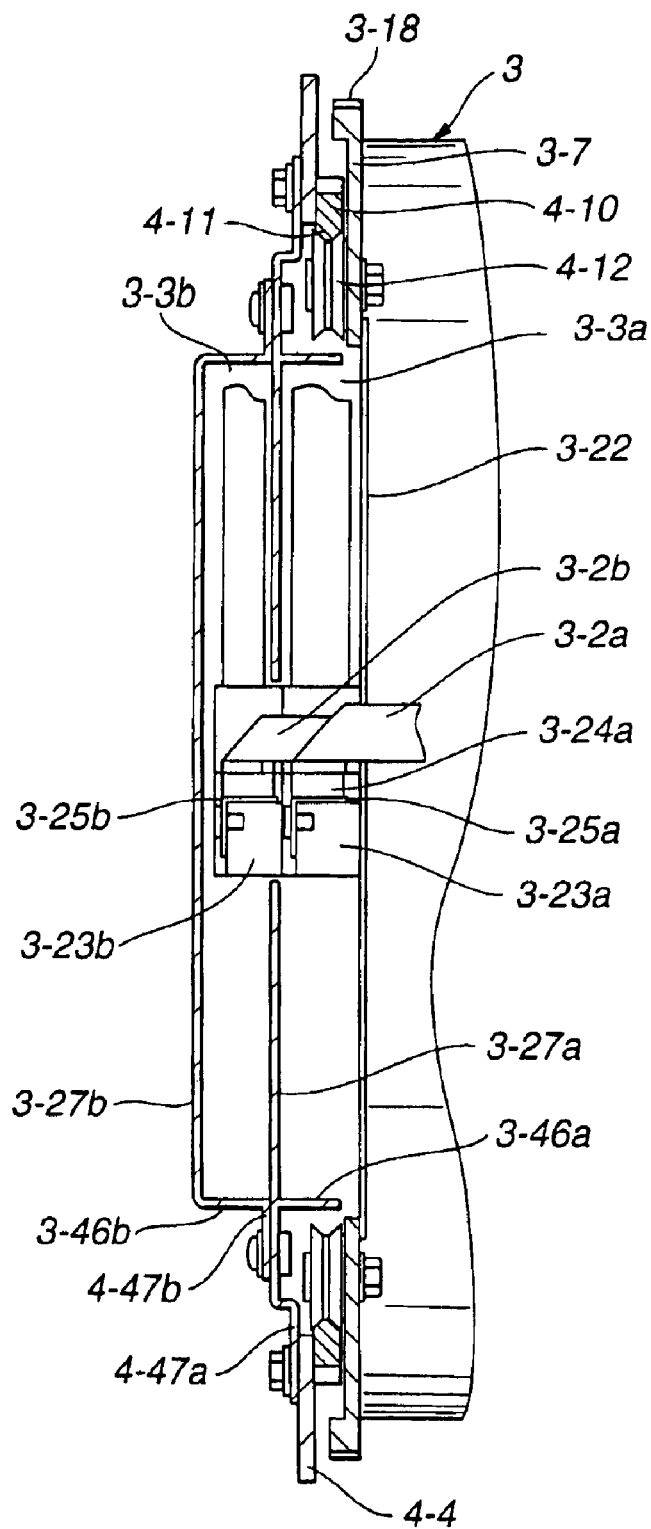

A seventh embodiment of the present invention will be described with reference to FIG. 36 and FIG. 37.

In the first embodiment, the cable 3-2 that is a flat flexible cable (FFC) or the like over which electric signals are transferred between the interior of the drum 3 and the exterior thereof is, as shown in FIG. 12A, stowed in the one cable stowage 3-3. In the present embodiment, a first cable stowage 3-3a and a second cable stowage 3-3b are formed as shown in FIG. 36. A video line FFC 3-2a and a power line FFC 3-2b that are separated from each other are stowed in the stowages 3-3a and 3-3b respectively.

A first hollow shaft 3-23a is located outside the center line of the drum 3. The video line FFC 3-2a over which a video signal is transmitted is fastened to the first hollow shaft 3-23a with a locking member 3-25a, to which an elastic member 3-24a is bonded, between them. One end of the FFC 3-2a is, as shown in FIG. 17A, led to the relay printed-circuit board 3-26 located inside the drum cover 3-22 through the hollow of the first hollow shaft 3-23a. The locking member 3-25a is screwed to the first hollow shaft 3-23a.

The video line FFC 3-2a spirally curled within the first cable stowage 3-3a is covered by a first cover member 3-27a. The outer edge of the first cover member 3-27a is folded in the shape of letter L in order to form a convex part 3-46a that restricts the spread of the FFC 3-2a to a certain diameter. A range of the FFC 3-2a taken up axially is thus restricted, whereby the spirally curled state of the FFC 3-2a is prevented from being destroyed.

A plurality of projections 4-47a projecting outwards from the convex part 3-46a of the first cover member 3-27a is fixed to the second frame 4-4.

A second hollow shaft 3-23b is attached to the first hollow shaft 3-23a. The power line FFC 3-2b over which power is supplied is fixed to the second hollow shaft 3-23b with a locking member 3-25b, to which an elastic member 3-24b is bonded, between them. One end of the FFC 3-2b is passed through the first and second hollows, and led inwards beyond the drum cover 3-22 to the relay printed-circuit board 3-26 located inside the drum cover 3-22.

The power line FFC 3-2b spirally curled within the second cable stowage 3-3b is covered with a second cover member 3-27b. An outer edge of the second cover member 3-27b is folded in the shape of letter L in order to form a convex part 3-46b that restricts the spread of the FFC 3-2b to a certain diameter. A range of the FFC 3-2b taken up axially is thus restricted in order to prevent the spirally curled state of the FFC 3-2b from being destroyed.

A plurality of projections 4-47b projecting outwards from the convex part 3-46b of the second cover member 3-47 is screwed to the first cover member 3-27a. The other components are identical to those shown in FIG. 12. The description of the components will be omitted.

In the present embodiment, the video line FFC 3-2a and power line FFC 3-2b are stowed mutually independently in the cable stowages 3-3a and 3-3b respectively while being spirally curved. Consequently, appearance of a noise in an image derived from mixing of noises occurring in the video line FFC 3-2a and power line FFC 3-2b can be prevented effectively. According to the present embodiment, a noise that appears in an image can be alleviated to improve image quality.

Incidentally, the first cover member 3-27a partitioning the first cable stowage 3-3a and the second cable stowage 3-3b may be formed with a conducting member. The first cable stowage 3-3a and second cable stowage 3-3b may be formed with conducting members. Thus, the ability to prevent mixing of noises may be improved.

Moreover, the ability to prevent mixing of noises may be improved by grounding the conducting members.

If the cables are drawn out from the center of the drum 3, the sizes of the hollow shafts can be minimized. Consequently, the volumes of the cable stowages can be reduced.

Figure 37:
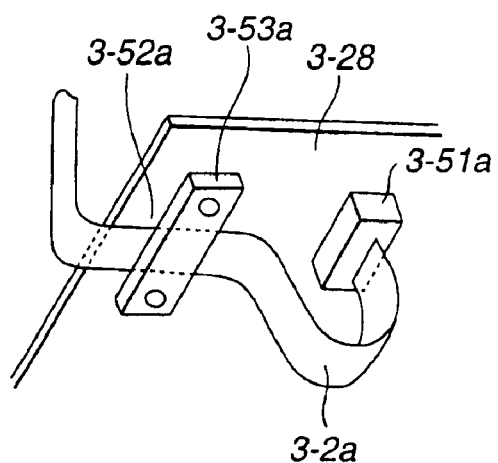
FIG. 36 and FIG. 37 are explanatory diagram concerning a seventh embodiment of the present invention.

Moreover, similarly to the above description made in conjunction with FIG. 14, the outer end of the spirally curled video line FFC 3-2a is, as shown in FIG. 37, coupled to the relay printed-circuit board 3-28 through a slit formed in the cover member 3-27a.

The FFC 3-2a is led to a connector 51a formed on the relay printed-circuit board 3-28. The relay printed-circuit board 3-28 has a planar part 3-52a whose width is larger than the width of the FFC 3-2a. The FFC 3-2a is crawled along the planar part 3-52a and pressed against the planar part 3-52a using a cable presser member 3-53a. The FFC 3-2 is thus fixed to the relay printed-circuit board 3-28a. When the FFC 3-2a is secured using the cable presser member 3-53a, a play is preserved in a portion of the FFC 3-2a between the cable presser member 3-53a and connector 3-51a.

Likewise, the power line FFC 3-2b is led and fixed to the relay printed-circuit board 3-28. In FIG. 37, the FFC 3-2a is led and fixed to the relay printed-circuit board 3-28 located outside the drum 3. The same applies to a case where the FFC 3-2a is led and fixed to the relay printed-circuit board 3-26 located inside the drum 3.

Thus, a drawback described below is resolved.

Normally, a cable such as a single conductor is secured with the middle point of the cable fixed to another member using a binding band or the like for fear a load may be imposed on a connector formed on a printed-circuit board to which the cable is led. However, as far as a FFC is concerned, it is impossible to fix the FFC to another member using a cable-like binding band. The FFC is generally bonded to another member using an adhesive such as a double-sided adhesive tape. However, when the FFC is bonded to another member using the adhesive, the member to which the FFC is bonded must have a planar part on the surface thereof. Talking of the strength of adhesive bonding, if the strength is low, the FFC is readily peeled off. If the strength is too high, workability deteriorates.

When the FFC 3-2a or the like is secured as mentioned above, the FFC 3-2a or the like can be secured without deterioration of workability. Beside, no load is imposed on the connector 3-51a or the like on the relay printed circuit board 3-28a to which the FFC 3-2a or the like is led.

According to the present embodiment, the FFC 3-2a or the like can be led and fixed easily. Excellent workability can be guaranteed.

(Eighth Embodiment)

Figure 38:
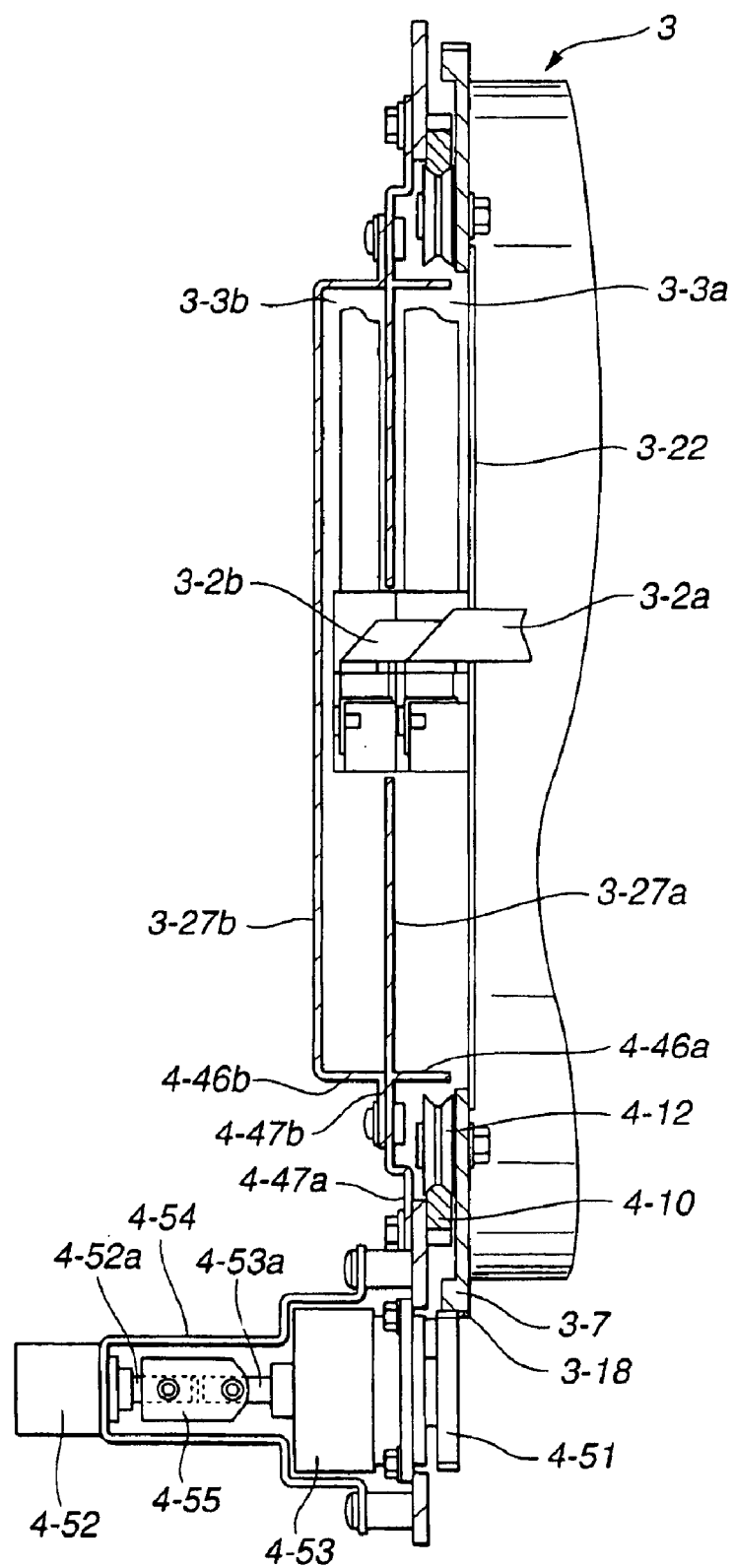
FIG. 38 shows part of a drum employed in an eighth embodiment of the present invention.

An eighth embodiment of the present invention will be described with reference to FIG. 38.

In the first and second embodiment, a length by which the insertion member 2-1 is wound about the drum 3 is detected using the sliding variable resistor 4-20. In the present embodiment, a multi-rotation variable resistor (multi-rotation potentiometer) 4-52 is used for the detection.

The resistance at the variable resistance terminal of the multi-rotation variable resistor 4-52 varies corresponding to the number of rotations made by a shaft 4-52a that is rotatable. More particularly, the shaft 4-52a rotates with a contact on the shaft 4-52a abutted on a resistor line that extends spirally.

A gear 4-51 is engaged with the gear 3-18 formed on the periphery of the second side panel 3-7 fixed to the outer edge of the second drum cover 3-22. For engaging the gear 4-51 with the gear 3-18, the multi-rotation variable resistor 4-52 and a speed reducer 4-53 are attached to the second frame 4-4 using a bracket 4-54 screwed to the second frame 4-4.

When the gear 3-18 is rotated, the gear 4-51 engaged with the gear 3-18 rotates. The rotation has its rotating speed reduced by the speed reducer 4-53 whose input shaft is joined with the shaft of the gear 4-51. This causes an output shaft 4-53a to rotate at a reduced speed.

The speed reducer 4-53 has a plurality of gears incorporated therein. The output shaft 4-53a rotates at a speed reduced by the plurality of gears. The output shaft 4-53a is linked and fixed to the shaft 4-52a of the multi-rotation variable resistor 4-52 by a linkage member 4-55. The shaft 4-52a of the multi-rotation variable resistor 4-52 rotates with the rotation of the output shaft 4-53a. The resistance at the variable resistance terminal varies corresponding to the number of rotations made by the shaft 4-52a. The other components are identical to those shown in FIG. 36.

According to the present embodiment, the rotation of the drum 3 is conveyed to the multi-rotation variable resistor 4-52 via the speed reducer 4-53. The number of rotations of the drum 3 can be converted into an electric signal. Consequently, a length by which the insertion member 2-1 is wound about the drum 3, or in other words, how long the insertion member 2-1 is wound about the drum can be detected.

In this case, the number-of-rotations sensing mechanism has the capability of a nonvolatile storage similarly to the one employed in the first embodiment. Specifically, even if the power supply is turned on after being turned off, a length by which the insertion member 2-1 is wound can be detected based on the resistance.

(Ninth Embodiment)

A ninth embodiment of the present invention will be described with reference to FIG. 39 to FIGS. 43A and 43B.

An object of the present embodiment is to prevent buckling of the insertion member by preventing the drum from rotating despite an attempt made to rotate the drum in a direction of rotation permitting drawing out of the insertion member.

Figure 39:
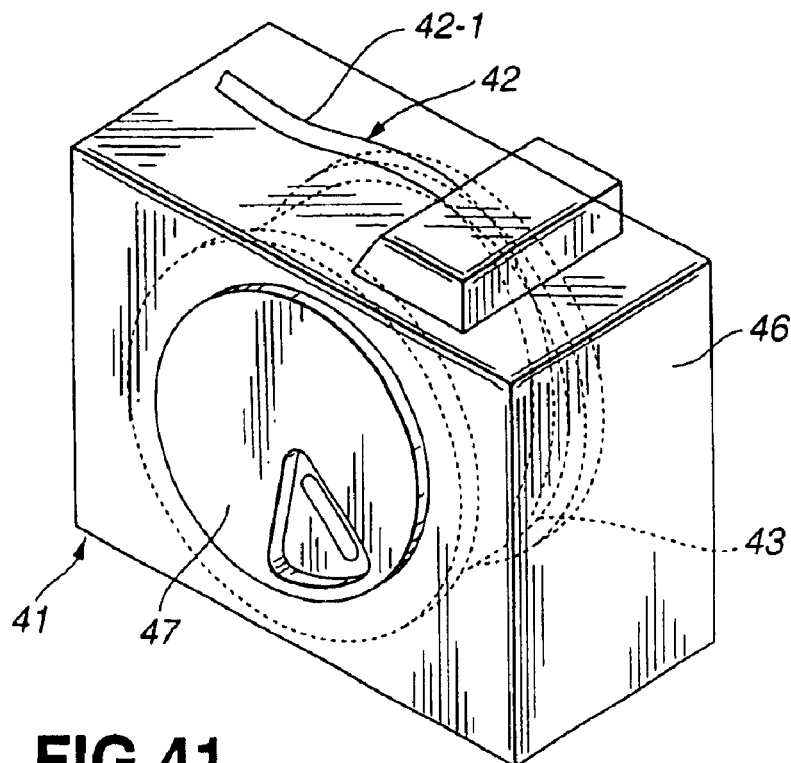

As shown in FIG. 39, a drum-inclusive endoscope system 41 consists mainly of an endoscope 42 for industrial use, a cylindrical drum 43, a frame 44, a case 46, and a disk-like rotational panel 47. The industrial endoscope 42 includes an elongated insertion member 42-1 that is flexible. The elongated insertion member 42-1 is wound about the periphery of the cylindrical drum 43. The frame 44 rotatably holds the drum 43 freely. The case 46 has shock absorbers 45 (see FIG. 40) that alleviate shock force. The rotational panel 47 has its center aligned with the center of an opening formed in one side surface of the case 46, and has a mechanism, which winds the insertion member 42-1 about the drum 43, coupled to one side surface of the drum.

Figure 41:
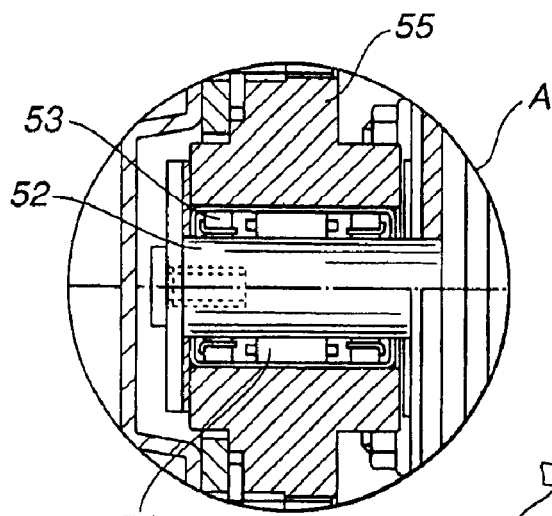
Figure 40:
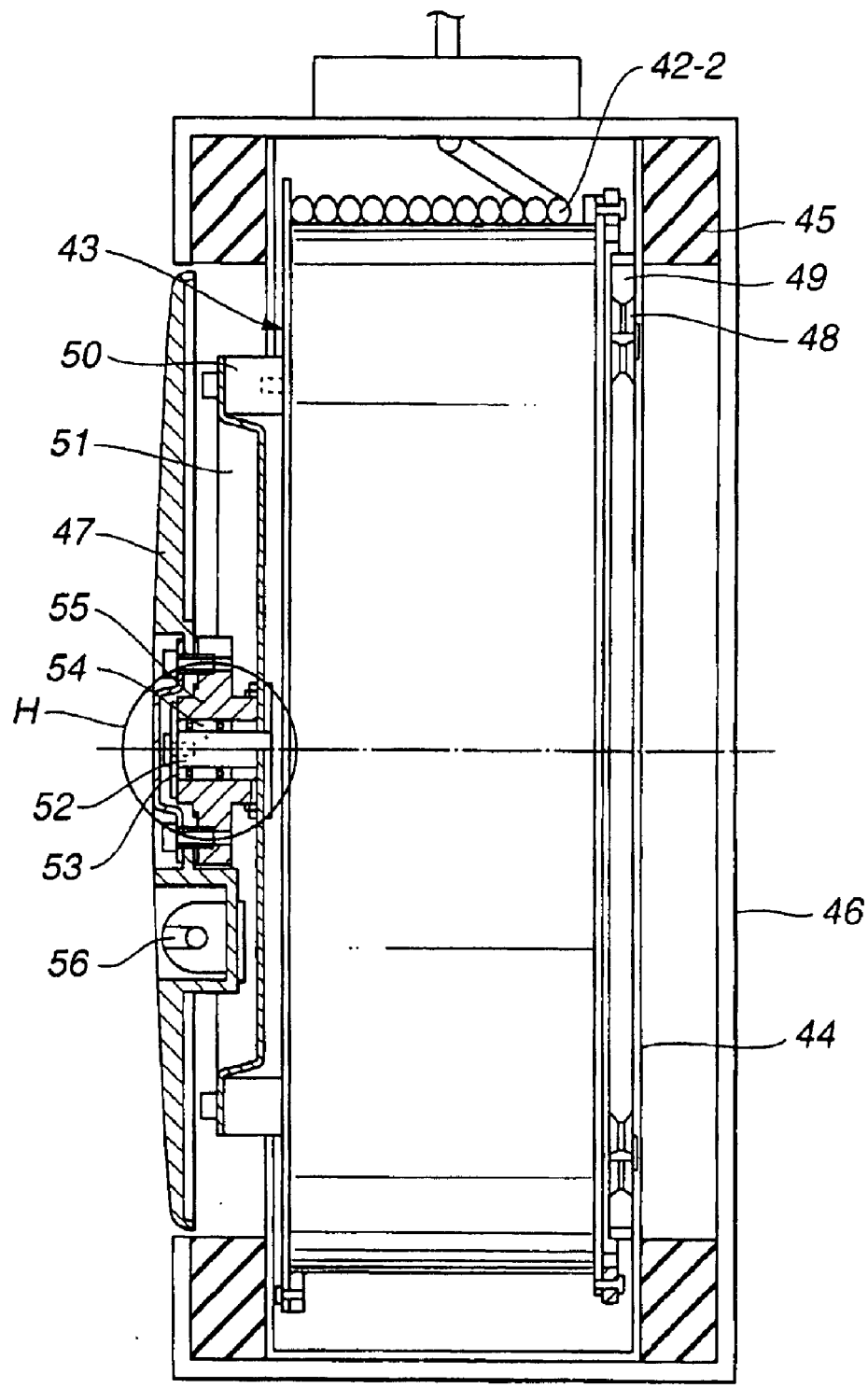

Referring to FIG. 40 and FIG. 41 that shows in enlargement the center of the mechanism, the mechanism interposed between the drum 43 and rotational panel 47 will be described below.

Three or more bearings 48 are fixed equidistantly on a side surface of the drum 43 opposite to the side surface thereof on which the rotational panel 47 is attached while being separated from the center of the drum 43 by a certain distance. The bearings 48 enable the drum 43 to rotate. A donut-like ring 49 that holds the bearings 48 is fixed to the frame 44. The ring 49 rotatably holds the drum 43 in the frame 44 freely.

Three or more shock absorbers 50 for alleviating shocks are arranged equidistantly on the outer edge of one side surface of the drum 43 while being separated by a certain distance from the center of the side surface thereof. A plate 51 is fixed to the shock absorbers 50, and a shaft 52 is fixed to the center of the plate 51. A bearing 53 and a one-way clutch 54 are engaged with the periphery of the shaft 52. The one-way clutch 54 has the capability of a clutch that conveys torque in one direction of rotation. The bearing 53 and the outer ring of the one-way clutch 54 are pressured to a mount 55.

The rotational panel 47 used to rotate the drum 43 is fixed to the mount 55. A lever 56 to be manipulated in order to take up the insertion member 42-1 is fixed to a point separated by a predetermined distance from the center of the rotational panel 47. The one-way clutch 54 is fitted in the mount 55 so that it will be engaged with the shaft 52 when the rotational panel 47 is turned in a direction of rotation permitting taking up of the insertion member.

Figure 42:
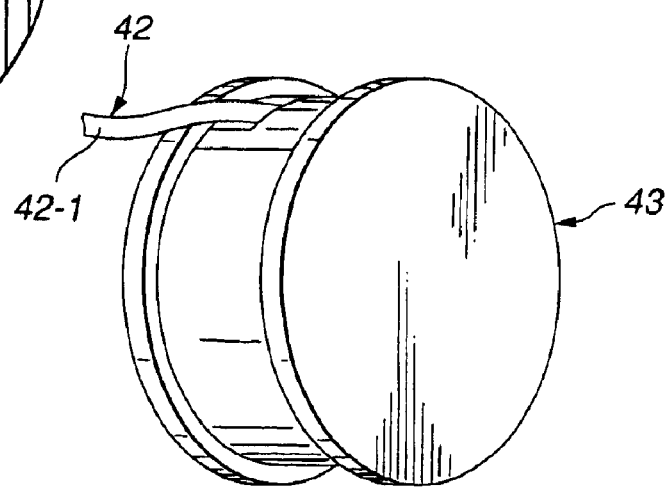

As shown in FIG. 42, the proximal part of the insertion member 42-1 of the industrial endoscope 42 is fastened to the drum 43. In the present embodiment, the shaft 52 fixed to the center of the drum 43 is linked to the mount 55 fixed to the rotational panel 47 with the bearing 53 and one-way clutch 54 between them. When the rotational panel 47 is rotated in one direction, that is, a direction of rotation permitting winding of the insertion member 42-1 about the drum 43, the drum 43 is rotated together with the rotational panel 47. When the rotational panel 47 is turned in an opposite direction, the drum 43 will not be rotated.

Next, an operation to be exerted by the present embodiment will be described below.

Owing to the foregoing structure, when a worker holds the lever 46 to turn the rotational panel 47 in the direction of rotation permitting taking up of the insertion member 42-1 of the industrial endoscope 42, the mount 55 to which the rotational panel 47 is fixed rotates. This causes the bearing 43 and one-way clutch 54, which are fitted in the mount 55, to rotate. Consequently, the one-way clutch 54 is engaged with the shaft 52.

Movements to be made in the above case will be described with reference to FIG. 43A.

As illustrated, when the mount 55 is rotated clockwise, a presser member 54a shaped substantially like a ring and abutted on the mount 55 rotates in the same direction. The presser member 54a is mounted on the periphery of the one-way clutch 54. Rollers 54c that can roll between adjoining ones of spacers 54b are stowed inside the presser member 54a. The shaft 52 is located inside the rollers 54c.

The pressure member 54a has an asymmetric inner surface that is asymmetric within a range of movement of each roller 54c. Specifically, the right-hand portion of the inner surface within the range of movement is formed as an inner surface 54d that is largely recessed. The roller 54c is settled inside the inner surface 54d without coming into contact with the inner surface 54d. In contrast, the left-hand portion of the inner surface of the pressure member 54a within the range of movement is formed as an inner surface 54e that is little recessed. Inside the inner surface 54e, the roller 54c comes into contact with the inner surface 54e and shaft 52 while being pressured against them.

Figure 43A:
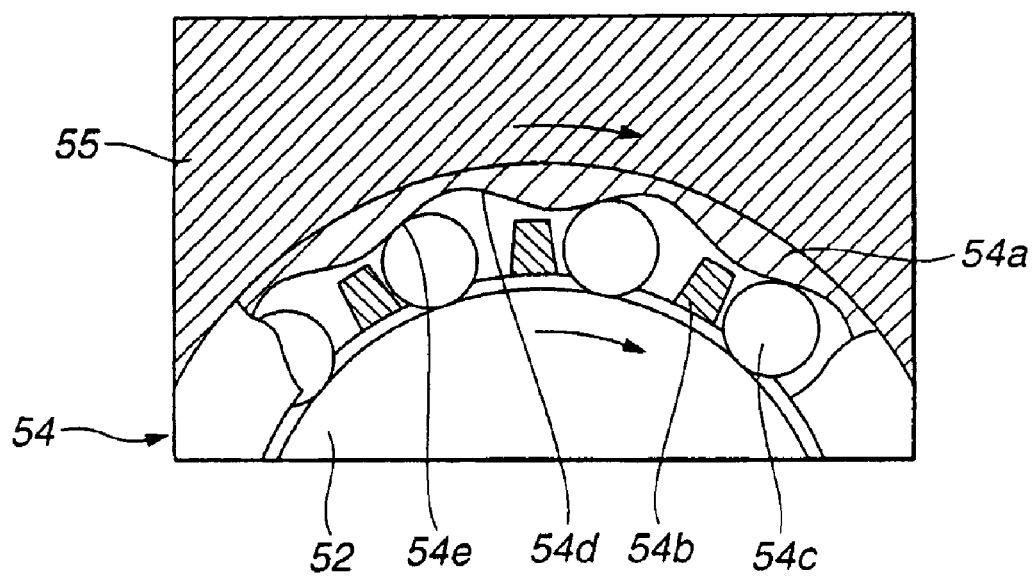

Consequently, as shown in FIG. 43A, when the presser member 54a rotates with the rotation of the mount 55, the rollers 54c are pressured to and brought into contact with the inner surfaces 54e of the presser member 54a that are little recessed, and the shaft 52.

In other words, when the mount 55 rotates clockwise, bring the presser member 54a is pressured to and brought into contact with the inner surface of the mount 55 because of the rollers 54c. Besides, torque exerted by the mount 55 is conveyed to the shaft 52 that is pressured to and brought into contact with the rollers 54c. This causes the shaft 52 to rotate.

When the shaft 52 rotates, the plate 51 rotates. Consequently, the drum 43 borne by the frame 44 with the shock absorbers 50 between them is rotated owing to the bearings 48 and ring 49. When the drum 43 rotates, the insertion member 42-1 of the industrial endoscope 42 whose end is fastened to the drum 43 is wound about the periphery of the drum 43, and thus stowed in the case.

Figure 43B:
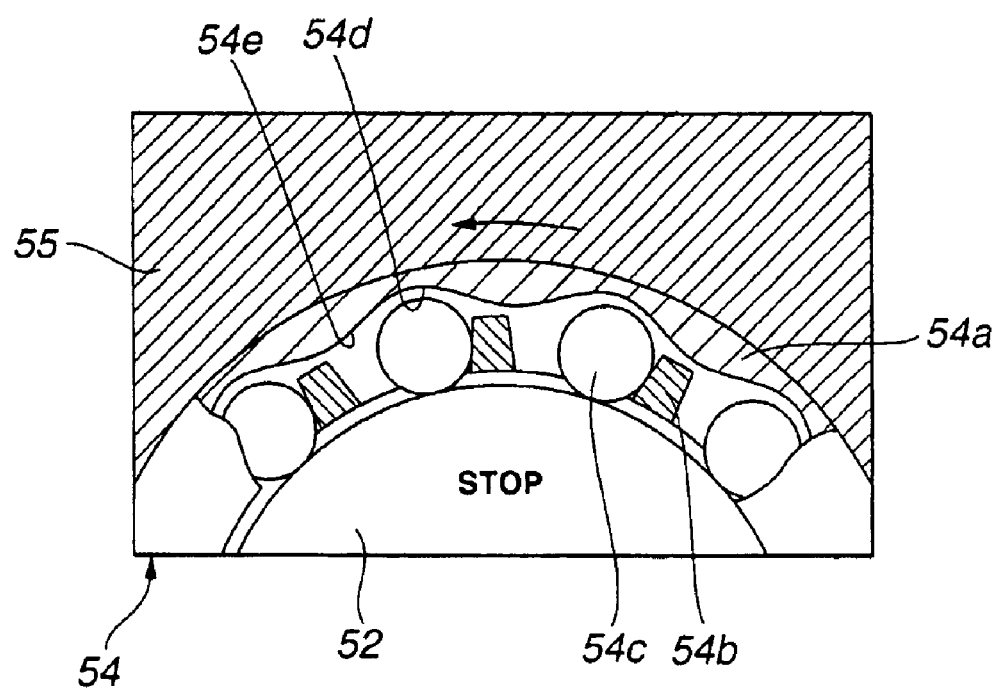

In contrast, when a worker holds the lever 56 to turn the rotational panel 47 counterclockwise in FIG. 43B, that is, in a direction of rotation permitting drawing out of the industrial endoscope 42, the mount 55 fixed to the rotational panel 47 is rotated. When the mount 55 rotates, the one-way clutch 54 rotates accordingly.

In other words, as shown in FIG. 43B, when the presser member 54a is rotated, the rollers 54c are settled inside the inner surfaces 54d of the presser member 54c while being restricted by the spacers 54b but not brought into contact with the inner surfaces 54d. In this state, the rollers 54c convey no torque.

In short, although the mount 55 rotates, the one-way clutch 54 does not convey the rotation of the mount 55 to the shaft 52. The shaft 52 therefore does not rotate. Since the shaft 52 does not rotate, the drum 43 does not rotate.

Owing to the foregoing structure, if a worker by mistake turns the lever 56 in the direction opposite to the direction of rotation permitting taking up of the insertion member, and thus tries to draw out the industrial endoscope 42, the drum 43 does not rotate. The industrial endoscope 42 therefore will not float above the drum 43. Buckling can therefore be prevented.

(Tenth Embodiment)

Figure 44:
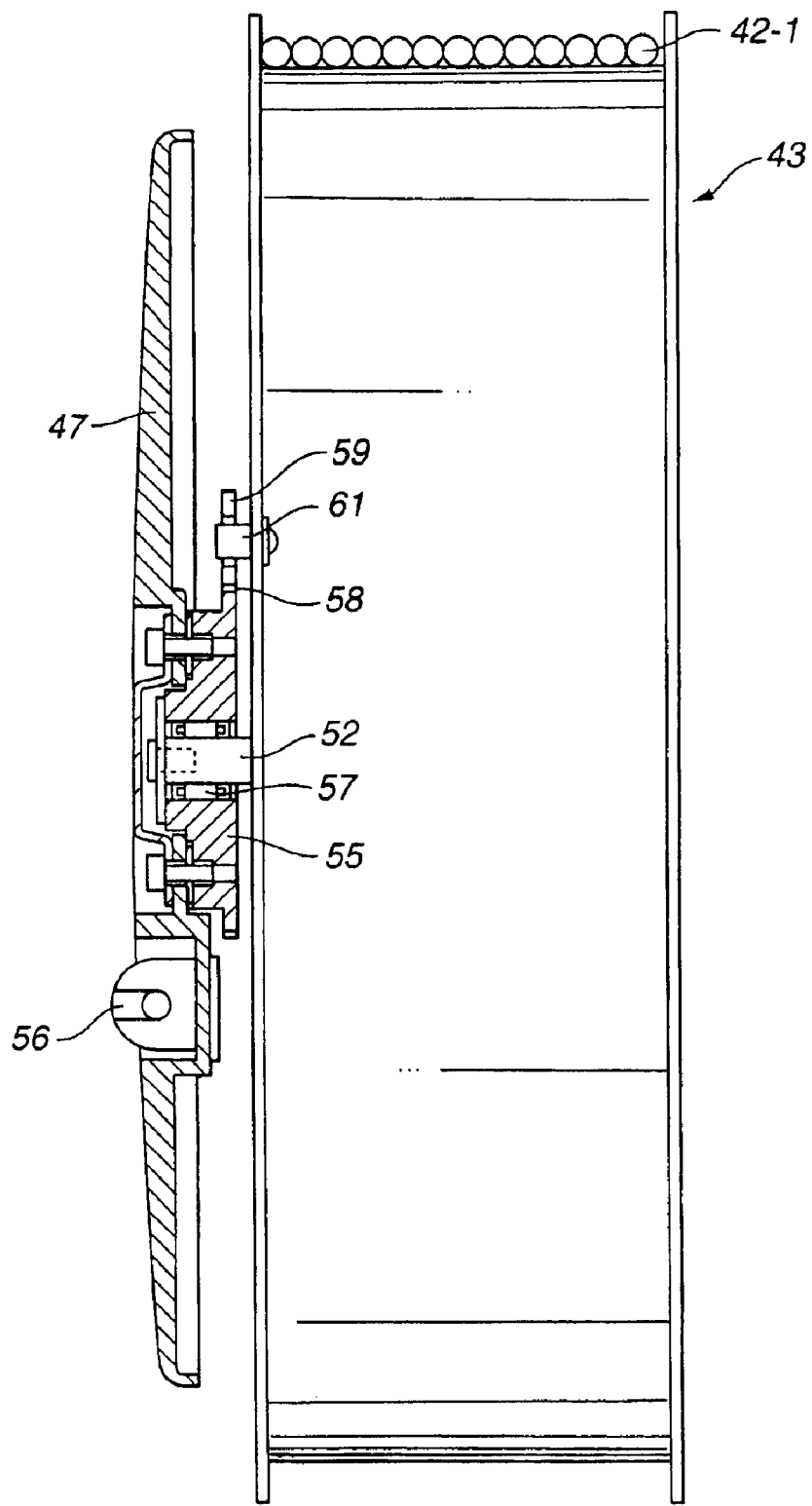

A tenth embodiment of the present invention will be described with reference to FIG. 44 to FIG. 46.

In the ninth embodiment, the bearing 53 and one-way clutch 54 are interposed between the shaft 52 and the mount 55 mounted on the periphery of the shaft 52. In the present embodiment, a bearing 57 is, as shown in FIG. 44, fitted in the mount 55. A gear 58 is formed on the periphery of the mount 55, and a gear 59 is located at a position at which the gear 59 is engaged with the gear 58.

Figure 45:
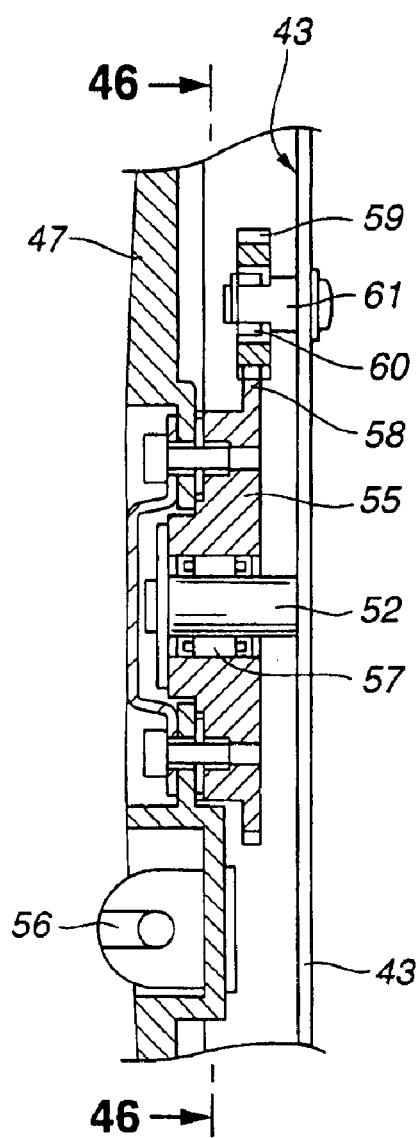
Figure 46:
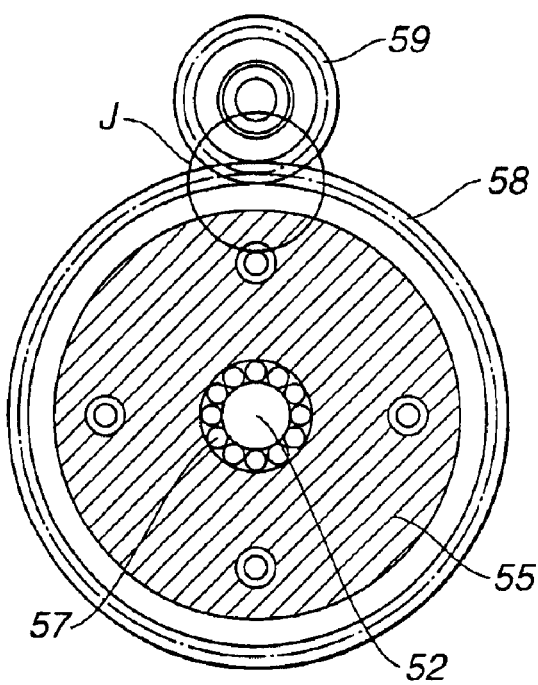

As shown in FIG. 45, a one-way clutch 60 is fitted in the center of the gear 59. A shaft 61 is engaged with the center of the one-way clutch 60. The shaft 61 is fixed to one side surface of the drum 43. The mount 55 is fixed to the rotational panel 47 having the lever 56.

An operation to be exerted by the present embodiment will be described below.

Similarly to the ninth embodiment, when the lever 56 is used to turn the rotational panel 47 in the direction of rotation permitting taking up of the industrial endoscope 42, the one-way clutch 60 and shaft 61 are engaged with each other. This causes the drum 43 to rotate.

Figure 47A:
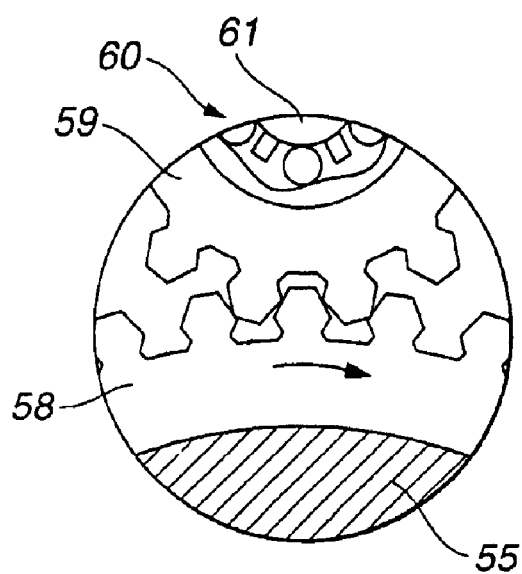

In other words, as shown in FIG. 47A, the one-way clutch 60 whose periphery is engaged with the gear 59 is locked while being engaged with the shaft 61. When the lever 56 is turned in order to rotate the mount 55, the locked state of the one-way clutch 60 engaged with the shaft 61 is retained and the drum 43 is rotated.

Figure 47B:
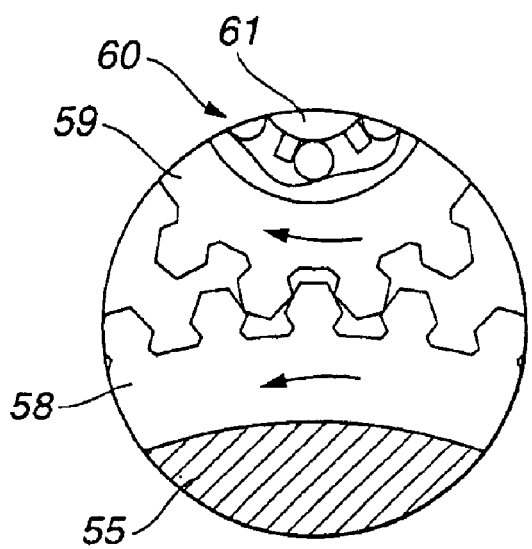

In contrast, when the rotational panel 47 is turned in the opposite direction, the one-way clutch 60 and shaft 61 are, as shown in FIG. 47B, not engaged with each other. The drum 43 therefore does not rotate.

As mentioned above, the present embodiment provides the same advantage as the ninth embodiment. In addition, a mechanism for rotating and bearing the shaft 52 can be constructed easily.

(Eleventh Embodiment)

An eleventh embodiment of the present invention will be described with reference to FIG. 48 to FIGS. 50A and 50B.

Figure 48:
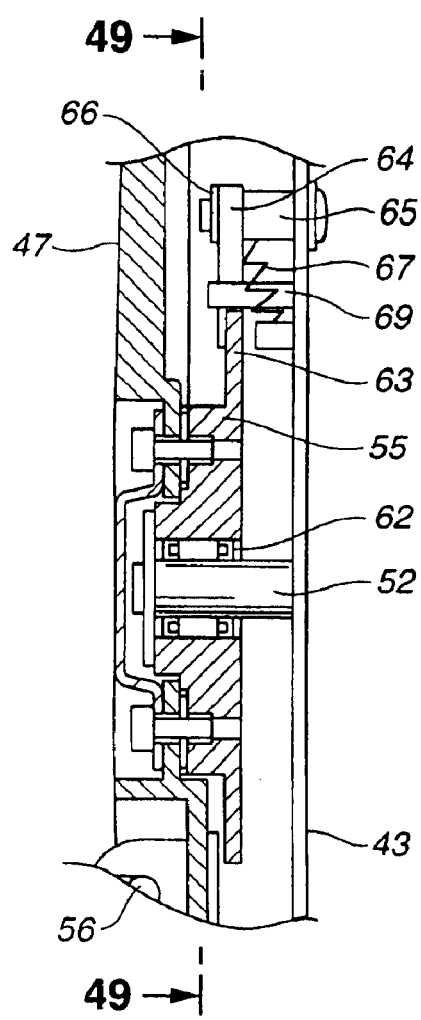

As shown in FIG. 48, the present embodiment has a bearing 62 fitted in the mount 55. A sprocket 63 is formed on the periphery of the mount 55, and a claw 64 is located at a position at which it is meshed with the sprocket 63.

The claw 64 is fixed to the drum 43 so that it can pivot with a shaft 65 as a center. The claw 64 attached to the shaft 65 is prevented from coming off by means of an E ring 66 or any other member.

Figure 49:
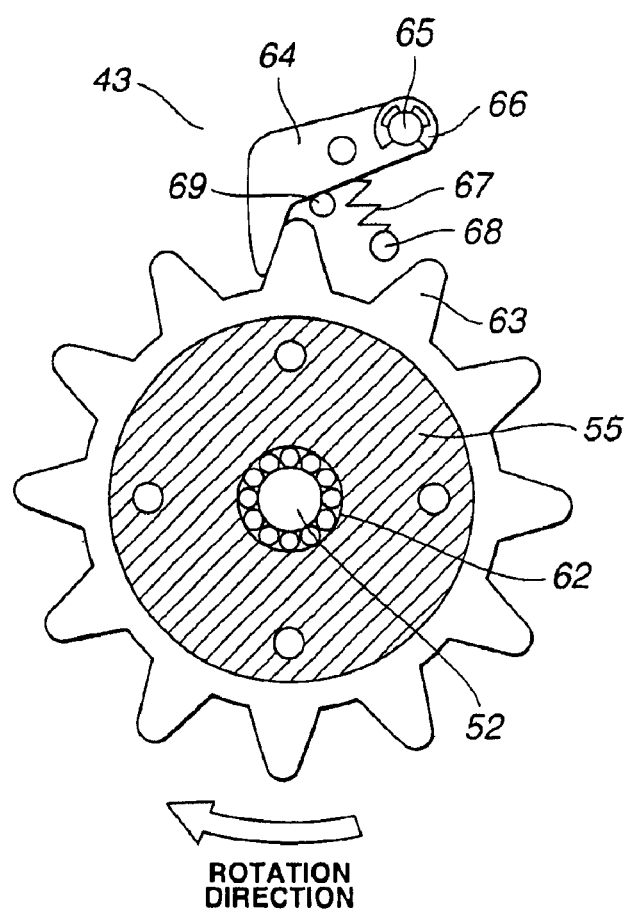

As shown in FIG. 49, one end of a tension spring 67 is fixed to a point on the claw 64, and the other end thereof is hooked on a shaft 68 fixed to one side surface of the drum 43. Moreover, a claw movement restriction pin 69 is jutted inside the claw 64. The claw 64 is constrained to meet the claw movement restriction pin 69 by means of the tension spring 67.

The claw 64 is constrained to pivot counterclockwise in FIG. 49 with the shaft 65 as a fulcrum by means of the tension spring 67. Owing to the constraining force, the claw 64 is normally held abutted against the claw movement restriction pin 69. The mount 55 is fixed to the rotational panel 47 having the lever 56.

Next, an operation to be exerted by the present embodiment will be described below.

As shown in FIG. 49, the claw 64 is always abutted on the sprocket 63 owing to the spring 67. When the rotational panel 47 is turned in the direction of rotation permitting taking up of the industrial endoscope 42, the claw 64 and sprocket 63 are engaged with each other.

Figure 50A:
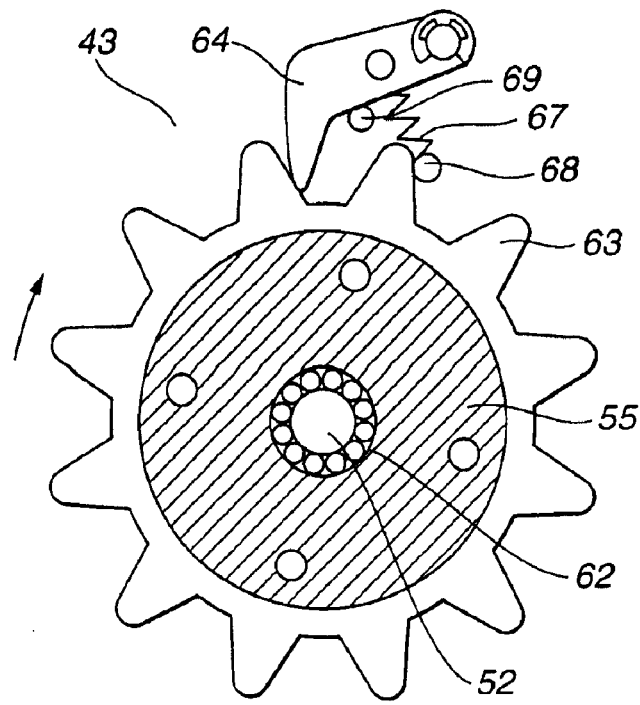

In other words, when the lever 56 is turned in the state shown in FIG. 49, the sprocket 63 is rotated together with the rotational panel 47 in the direction of rotation permitting taking up of the insertion member. Consequently, the claw 64 is, as shown in FIG. 50A, pressured by the sprocket 63 in the direction of rotation permitting taking up of the insertion member. However, the claw 64 cannot any longer move in the direction because of the presence of the claw movement restriction pin 69.

Therefore, when the sprocket 63 rotates, the claw 64 is held engaged with the sprocket 63. The drum 43 is rotated together with the sprocket 63.

Figure 50B:
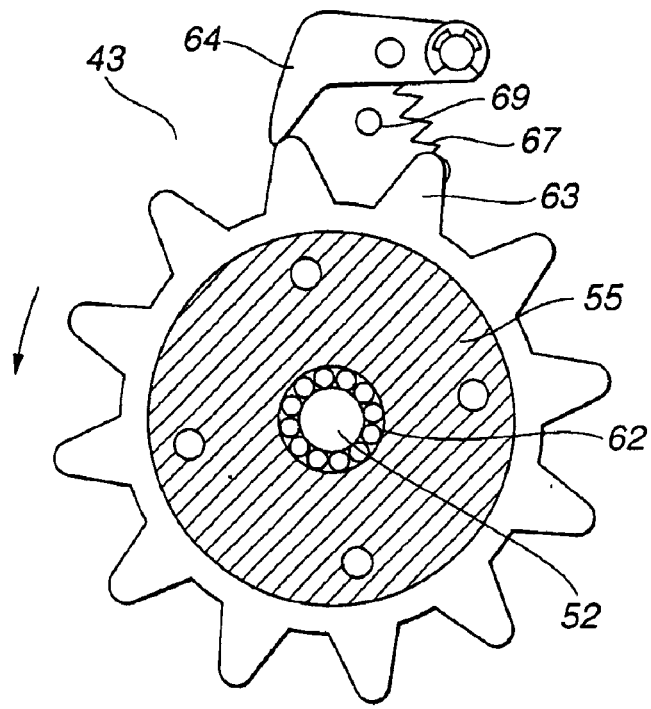

In contrast, when the rotational panel 47 is turned in the direction of rotation permitting drawing out of the industrial endoscope 2, the claw 64 and sprocket 63 are, as shown in FIG. 50B, not engaged with each other. The drum 43 is not rotated. The present invention provides nearly the same advantage as the tenth embodiment.

(Twelfth Embodiment)

A twelfth embodiment of the present invention will be described with reference to FIG. 51 and FIG. 52.

Figure 52:
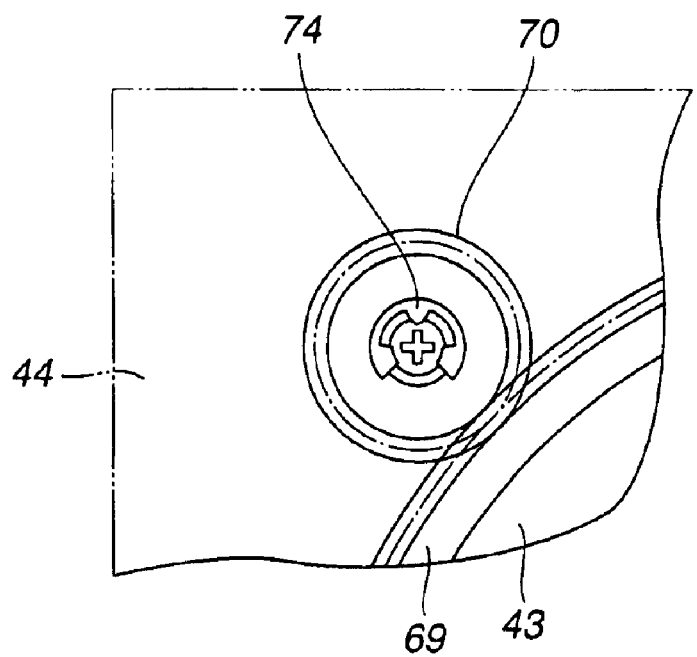

As shown in FIG. 52, the present embodiment has a gear 69 formed on the periphery of the drum 43 employed in the ninth embodiment. A small hollow gear 70 is located so that it will be engaged with the gear 69. An outer ring 71b of a hollow torque limiter 71 for restricting rotation is fixed to the small gear 70 so that the small gear 70 will be rotated with torque whose level is equal to or larger than a certain level.

Figure 51:
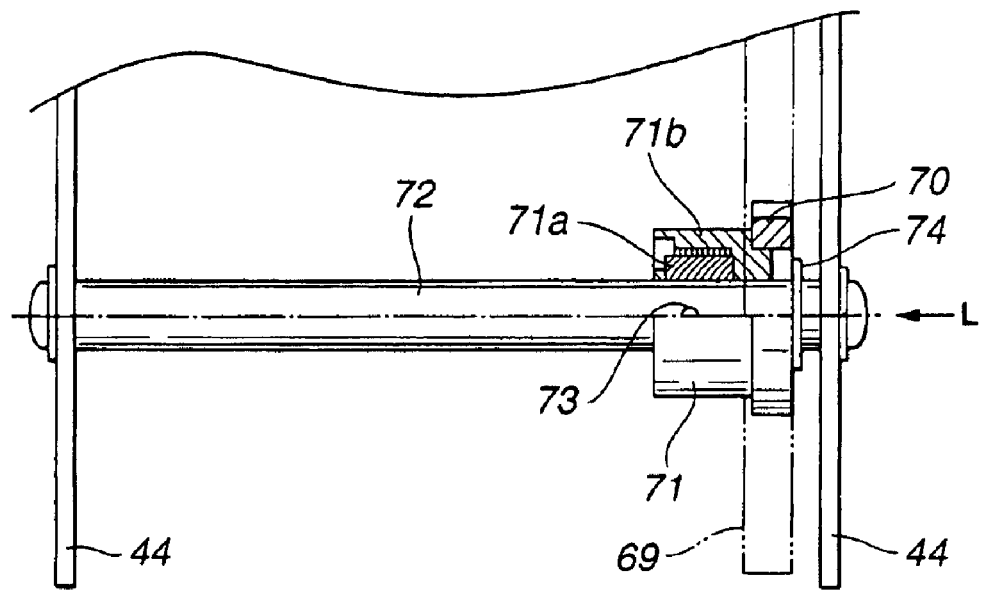
FIG. 51 and FIG. 52 are explanatory diagrams concerning a twelfth embodiment of the present invention.

As shown in FIG. 51, the torque limiter 71 has an inner ring 71a and the outer ring 71b, and generates a certain level of torque owing to friction between the inner ring 71a and outer ring 71b. A shaft 72 penetrates through the centers of the small gear 70 and torque limiter 71 respectively. The shaft 72 is fixed to the frame 44. The shaft 72 and the inner ring 71a of the torque limiter 71 are secured using a pin 73. An E ring 74 is placed on a side surface of the small gear 70, and fixed to the shaft 72.

According to the present embodiment, the gear 69 formed on the periphery of the drum 43 is engaged with the small gear 70. The small gear 70 is held with the shaft 72 extended to the frame 44 through the torque limiter 70. Only when torque whose level is equal to or larger than a certain level is applied to the gear 70, the gear 70 is rotated.

An operation to be exerted by the present embodiment will be described below.

When the industrial endoscope 42 is drawn out with the tip thereof held by a worker, the drum 43 is rotated. When the drum 43 rotates, the gear 69 formed on the periphery of the drum 43 rotates.

When the gear 79 rotates, the small gear 70 rotates. This causes the outer ring 71b of the torque limiter 71 to rotate. Since the inner ring 71 of the torque limiter 71 is fixed to the shaft 72, a certain level of torque is generated. Thus, torque causing the drum 43 to rotate is adjusted.

The present embodiment provides the advantage described below.

Even if a worker jerks the industrial endoscope 42, idle rotation of the drum 43 derived from inertia can be restricted by means of the torque limiter 71. Consequently, the industrial endoscope 42 will not be floated above the periphery of the drum 43. Buckling of the industrial endoscope 42 can be prevented.

(Thirteenth Embodiment)

Figure 53:
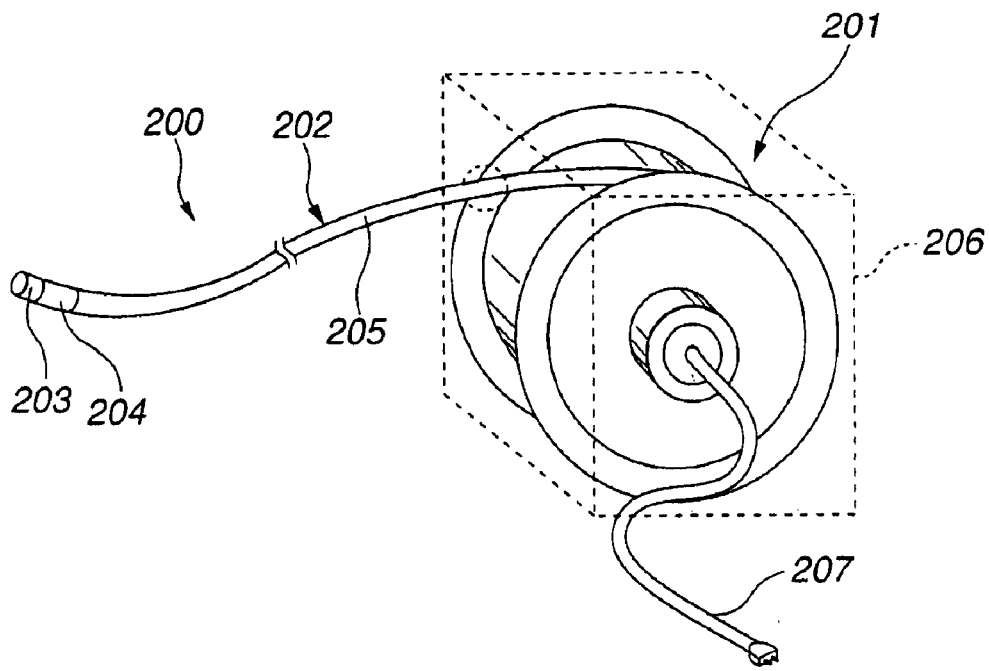
Figure 55:
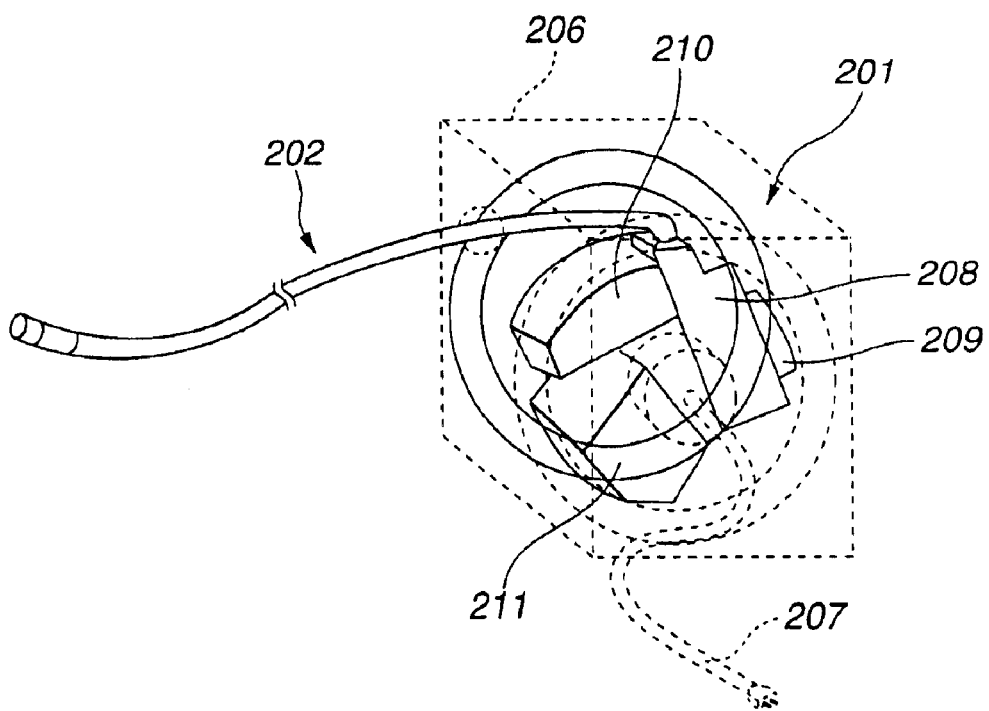
Figure 56:
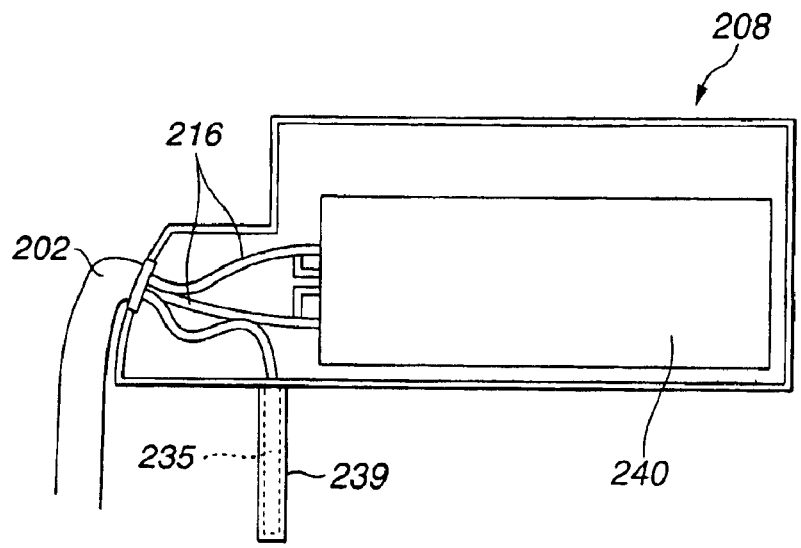
Figure 57:
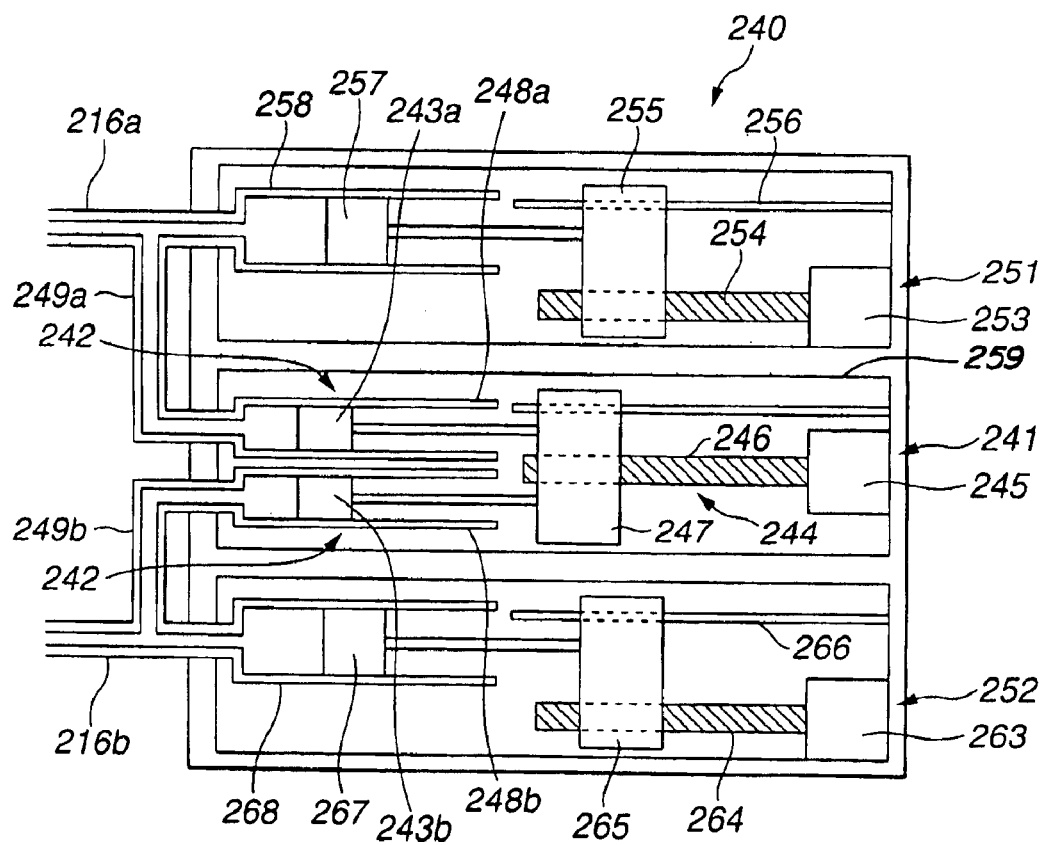
Figure 58:
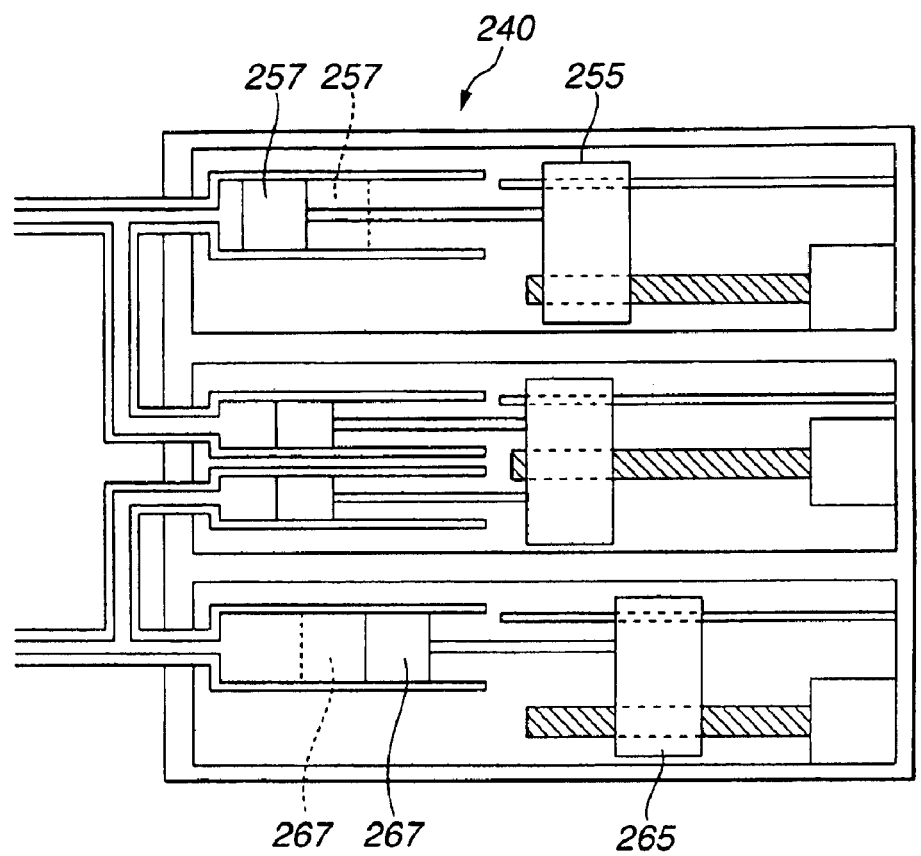

FIG. 53 to FIG. 58 are concerned with a thirteenth embodiment of the present invention. FIG. 53 shows the appearance of an endoscope system including a pneumatically angled endoscope. FIGS. 54A to 54D is an explanatory diagram concerning the structure of an insertion member. FIG. 55 shows the structure of a drum. FIG. 56 shows the structure of a bending section drive unit. FIG. 57 is an explanatory diagram showing in detail a bending section driving mechanism. FIG. 58 shows movements to be made in the bending section driving mechanism.

As shown in FIG. 53, an insertion member 202 of an endoscope 200 is fastened to a drum 201 including a pneumatic angling unit that serves as a motor-driven angling unit and that will be described later. The insertion member 202 is wound about the drum 201.

A tip 203 in which an optical system to be described later is incorporated is formed as a tip of the insertion member 202. A bending section 204 and a flexible tube 205 are concatenated proximally to the tip 203. The bending section 204 is bent by means of the pneumatic angling unit. The drum 201 is rotatably stowed in a case body 206 freely. A power cable 207 is extended from near the center of the drum 201.

As shown in the exploded perspective view of FIG. 54A showing the insertion member, the bending section 204 is formed with a multi-lumen tube 212 that is made of a silicon resin and is elastically tubular.

As seen from the sectional view of FIG. 54C showing the multi-lumen tube, an axial center lumen 213 is extended in the axial center of the multi-lumen tube 212. A plurality of outer lumens, or in the present embodiment, four outer lumens 214a, 214b, 214c, and 214d each shaped like an arc are substantially equidistantly formed around the axial center lumen 213 in the wall of the multi-lumen tube 212.

Both the front and rear ends of the four outer lumens 214a to 214d are blocked. In other words, the outer lumens 214a to 214d are formed as pressuring chambers 215 that are sealed fluid chambers. One ends of air tubes 216 coated with Teflon™ (manufactured by Du Pont Co., Ltd.) are joined with the blocked rear ends of the outer lumens 214a to 214d so that the air tubes will communicate with the pressuring chambers 215.

The ends of the air tubes 216 are inserted into bores of silicon tubes 217 in advance. The inner diameter of the silicon tubes 217 is, for example, made equal to or a bit smaller than the outer diameter of the air tubes 216, thus preventing the air tubes 216 from coming off from the silicon tubes 217.

The silicon tubes 217 are fitted into the rear parts of the outer lumens 214a to 214d. Thereafter, a gap between the inner surface of the rear part of each of the outer lumens 214a to 214d and the periphery of each silicon tube 217 is sealed by injecting a silicon sealant. Consequently, the four air tubes 216 are fitted into the four pressuring chambers 215 in the multi-lumen tube, whereby a pneumatic actuator unit 219 of the bending section 204 is realized.

As shown in FIG. 54B, an internal deformation restricting member 220 realized with a closely wound coil whose diameter is a bit smaller than the inner diameter of the axial center lumen 213 is fitted into the axial center lumen 213 of the multi-lumen tube 212. An external deformation restricting member 221 realized with a closely wound coil whose diameter is a bit larger than the outer diameter of the multi-lumen tube 212 is mounted on the periphery of the multi-lumen tube 212.

As long as the internal deformation restricting member 220 can be fitted into the axial center lumen 213 of the multi-lumen tube 212, the outer diameter of the internal deformation restricting member 220 may be equal to or a bit larger than the inner diameter of the axial center lumen 213. Even in this case, the bending section 204 can be bent. Similarly, the inner diameter of the external deformation restricting member 221 may be equal to or a bit smaller than the outer diameter of the multi-lumen tube 212. However, the aforesaid inner and outer diameters are optimal and preferable in terms of efficiency in assembling and smoothness in bending.

As shown in FIG. 54A, a front cap 222 made of, for example, a stainless steel is attached to the tip of the multi-lumen tube 212. The front cap 22 has a cylindrical part 223 and a small-diameter joint 224. The cylindrical part 223 has the same outer diameter as the outer diameter of the multi-lumen tube 212. The joint 224 projects backwards from the center of the read end of the cylindrical part 223, and has a smaller diameter. An adhesive is injected with the joint 224 inserted in the axial center lumen 213 of the multi-lumen tube 212, whereby the front cap 22 is integrated with the multi-lumen tube 212.

On the other hand, a rear cap 225 made of, for example, a stainless steel is attached to the rear end of the multi-lumen tube 212. The rear cap 225 has a cylindrical part 226 and a small-diameter joint 227. The cylindrical part 226 has the same outer diameter as the outer diameter of the multi-lumen tube 212. The joint 227 projects forwards from the center of the end surface of the cylindrical part 226, and has a smaller diameter. An adhesive is injected with the joint 227 inserted into the axial center lumen 213 of the multi-lumen tube 212, whereby the rear cap 225 is integrated with the multi-lumen tube 212.

As seen from the sectional view of FIG. 54D showing the cylindrical part of the rear cap, an axial center hole 228 that is a through hole is bored in the axial center of the cylindrical part 226 of the rear cap 22. Four tube passage holes 229 that are through holes are equidistantly bored around the axial center hole 228 along the periphery of the rear cap 225.

The four air tubes 216 included in the pneumatic actuator unit 219 of the bending section 2-4 are inserted into the four tube passage holes 229. Moreover, The four air tubes 216 included in the pneumatic actuator unit 219 pass through the rear cap 225, run through the flexible tube 205, and reach a branching member. A tip flexible tube cap 230 fixed to the tip of the flexible tube 205 is joined with the cylindrical part 226 of the rear cap 225.

Moreover, a CCD unit 231 is stowed in the cylindrical part 223 of the front cap 222 shown in FIG. 54A. A CCD 232 that is a solid-state imaging device serving as an imaging means included in an observation optical system, and an illumination optical system 233 are incorporated in the CCD unit 231. A signal line 234 over which an electric signal is transmitted is led to the CCD 232. A light guide 235 over which illumination light is propagated opens on the illumination optical system 233.

An optical adaptor 236 is one of a plurality of types of optical adaptors that have different optical properties and are prepared in advance. The optical adaptor 236 is attached to the face of the CCD unit 231. A tip cover 237 protects the optical adaptor 236.

As shown in FIG. 55, a pneumatic angling unit 208, an angling control circuit unit 209, a light source unit 210, and a CCU 211 are incorporated in the drum 201. The pneumatic angling unit 208 serves as a fluid supply/discharge unit. The light source unit 210 supplies illumination light. The CCU 211 produces a TV picture. The insertion member 202 is coupled to the pneumatic angling unit 208. The light source unit 210 and pneumatic angling unit 208 are coupled to each other using a light guide connector 239. The angling control circuit unit 209 is coupled to the pneumatic angling unit 208.

As shown in FIG. 56, the insertion member 202 is fixed to the pneumatic angling unit 208 in a state where watertightness is kept. The light guide 235 running through the insertion member 202 enters the pneumatic angling unit 208 and reaches the light guide connector 239. An end surface of the light guide 235 is placed on the bottom of the light guide connector 239.

The air tubes 216 extending from the insertion member 202 are introduced to the pneumatic angling unit 208. Bending section driving mechanisms 240 are incorporated in the pneumatic angling unit 208. The air tubes 216 extending from the pressuring chambers 215 are led to the bending section driving mechanisms 240.

The bending section driving mechanism will be detailed with reference to FIG. 57.

For brevity's sake, since the bending section driving mechanism responsible for vertical angling and the bending section driving mechanism responsible for lateral angling are identical to each other. The bending section driving mechanism responsible for vertical angling will therefore be described, and the description of the bending section driving mechanism responsible for lateral angling will be omitted.

As illustrated, the bending section driving mechanism 240 consists of three mechanism blocks, that is, two mechanism blocks responsible for driving and one mechanism block responsible for pressurization. The pressurization mechanism block 241 consists of two pressure generation mechanisms 242 and one linear driving mechanism 244.

To begin with, the pressurization mechanism block 241 includes a pressurization motor 245. A screw 246 serving as a driving force converting mechanism is threaded on the driving shaft of the pressurization motor 245. The screw 246 rotates with the rotation of the pressurization motor 245. A mover 247 mounted on the driving shaft can rotate freely and has its movements in longitudinal directions restricted. The mover 247 advances or withdraws with rotation of the screw 246. A detent 259 penetrates through the mover 247, whereby the mover 247 is disabled from rotating and restricted to linear advancement or withdrawal.

A first pressurization piston 243a and a second pressurization piston 243b that constitute a pressure generation mechanism are fixed to the mover 247. The first pressurization piston 243a and second pressurization piston 243b advance or withdraw along with the movement of the mover 247.

The first pressurization piston 243a and second pressurization piston 243b are put in a first pressurization cylinder 248a and a second pressurization cylinder 248b so that they can advance or withdraw while being sealed airtightly. A first pressurization tube 249a and a second pressurization tube 249b are joined airtightly with the first pressurization cylinder 248a and second pressurization cylinder 248b respectively.

Next, the mechanism blocks responsible for driving include a feed driving mechanism block 251 that feeds air and a return driving mechanism block 252 to which air returns. The driving mechanism blocks have the same structure.

The feed driving mechanism block 251 includes a feed motor 253. A feed screw 254 serving as a driving force converting mechanism is threaded on the shaft of the feed motor 253. The feed screw 254 rotates with the rotation of the feed motor 253. A feed mover 255 that can freely rotate and has its movements along the longitudinal directions restricted is mounted on the feed screw 254. The feed mover 255 advances or withdraws with the rotation of the feed screw 254. A detent 256 penetrates through the feed mover 255, whereby the feed mover 255 is disabled from rotating and restricted to linear advancement or withdrawal.

A feed piston 257 is fixed to the mover 255. The feed piston 257 advances or withdraws with the movement of the feed mover 255. The feed piston 257 is put in a feed cylinder 258 so that it can advance or withdraw while being sealed airtightly. A first air tube 216a is airtightly joined with the feed cylinder 258.

The structure of the return driving mechanism block 252 is identical to that of the feed driving mechanism block 251. The return driving mechanism block 252 consists of a return piston 267, a return cylinder 268, a return mover 265, a return screw 264, a return motor 263, and a detent 266. A second air tube 216b is airtightly joined with the return cylinder 268.

The pressurization tube 249a communicates with the air tube 216a, and the pressurization tube 249b communicates with the air tube 249b. The motors 245, 253, and 263 included in the bending section driving mechanism 240 are connected to the angling control circuit unit 209 over electric cables that are not shown. The motors 245, 253, and 263 are controlled by a control circuit, which is not shown, included in the angling control circuit unit 209. Furthermore, the motor-driven angling control circuit unit that is the angling control circuit unit 209 is logically connected to a joystick serving as an angling device. Moreover, an electric cable extending from the CCD 232 is led to the CCU 211, though the cable is not shown. An image signal is converted into a TV signal and transferred to an observation device such as a monitor located outside the drum. The CCU 211 includes a power supply from which power is supplied to the light source unit 210 and angling control circuit unit 209.

Now, actions to be performed in the present embodiment will be described below.

When power is supplied to the power supply in the CCU 211 over the power cable 207, power is supplied to the angling control circuit unit 209 via the CCU 211.

An angling command issued responsively to a manipulation performed on the angling device is sent to the motor-driven angling control circuit unit that is the angling control circuit unit 209. The command is converted into a control signal with which the motor is controlled. Based on the signal, an associated one of the motors 245, 253, and 263 rotates in a predetermined direction.

Initially, the first pressurization piston 243a and second pressurization piston 243b are drawn out of the first pressurization cylinder 248a and second pressurization cylinder 248b respectively. No pressure is applied to the interiors of the first air tube 216a and second air tube 216b respectively.

After power is supplied, when a rotation command is issued from the control circuit to the pressurization motor 245, the screw 246 rotates. Since the feed mover 247 is hindered from rotating by the detent 259, the feed mover 255 advances to push the first pressurization piston 243a and second pressurization piston 243b into the first pressurization cylinder 248a and second pressurization cylinder 248b respectively. Consequently, the first air tube 216a and second air tube 216b are pressurized through the first pressurization tube 249a and second pressurization tube 249b respectively.

The bending section driving mechanism is actuated with the first air tube 216a and second air tube 216b pressurized. In response to an angling command issued responsively to a manipulation performed on the angling device, the feed motor 253 and return motor 263 are rotated by a predetermined number of rotations associated with the angling command. The feed mover 255 and return mover 256 are, as shown in FIG. 58, moved in opposite directions in order to move the feed piston 257 and return piston 267 in the opposite directions.

This results in a difference in pressure between the first air tube 216a and second air tube 216b. Consequently, the bending section 204 bends.

For restoring the bent bending section 204, a command instructing that the feed motor 253 and return motor 263 should be restored to their initial states is sent based on a command issued responsively to a manipulation performed on the angling device. When the feed piston 257 and return piston 267 are restored to the initial states, the bent bending section 204 is restored.

As mentioned above, when the joystick that is not shown is manipulated, an angling controller controls supply or discharge of air to or from each of the four air tubes. Thus, the four pressuring chambers of the pneumatic actuator unit are selectively pressured. Consequently, the bending section realized with the multi-lumen tube can be bent in a predetermined direction or towards a pressuring chamber opposed to a pressured pressuring chamber.

(Fourteenth Embodiment)

Figure 59:
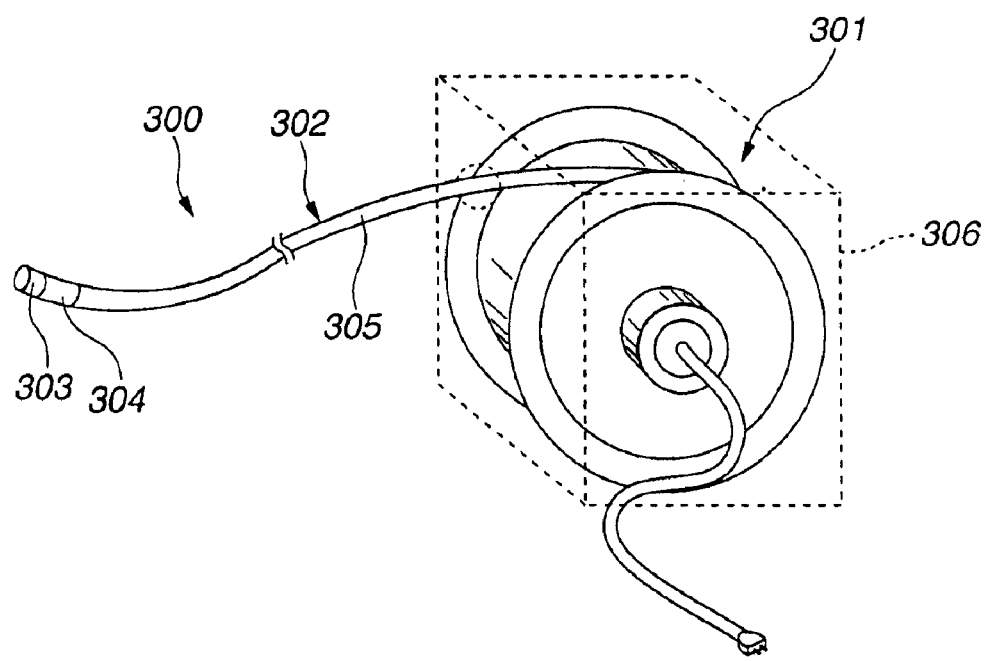
FIG. 59 to FIG. 64 are explanatory diagrams concerning a fourteenth embodiment of the present invention.
Figure 60:
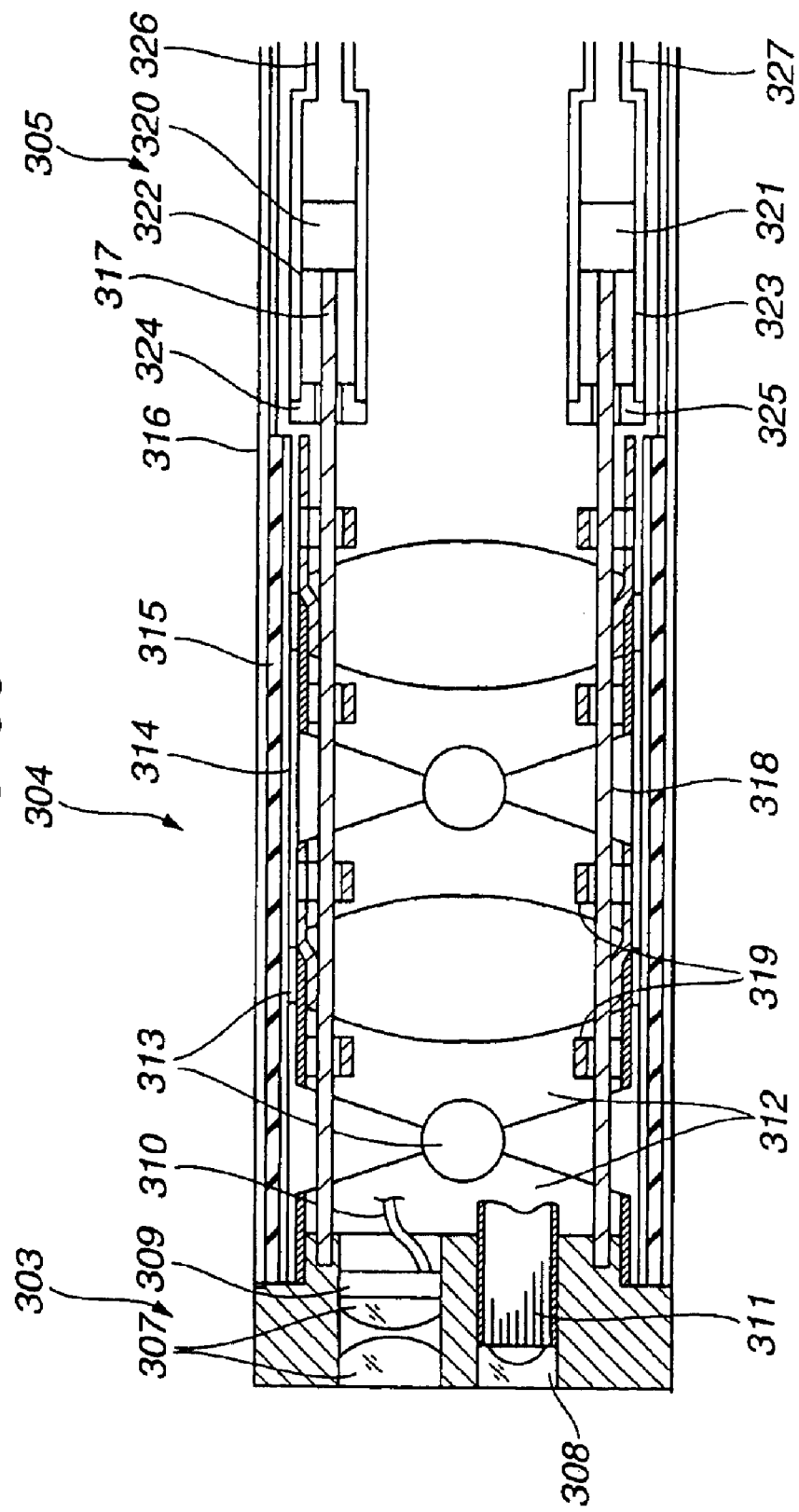
Figure 61:
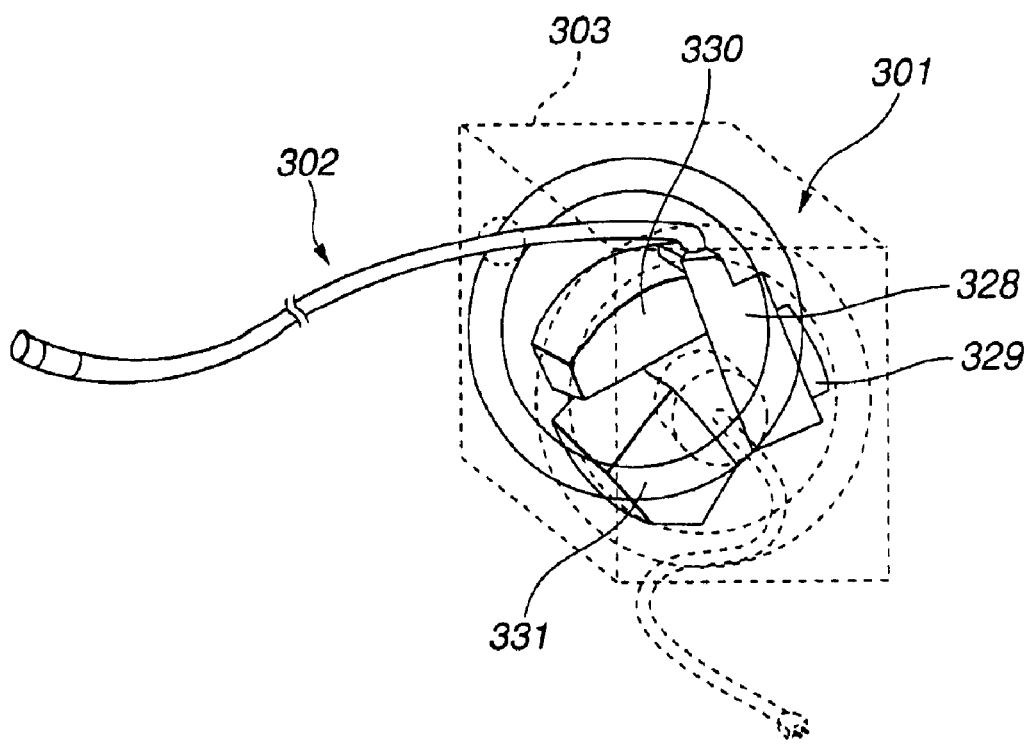
Figure 62:
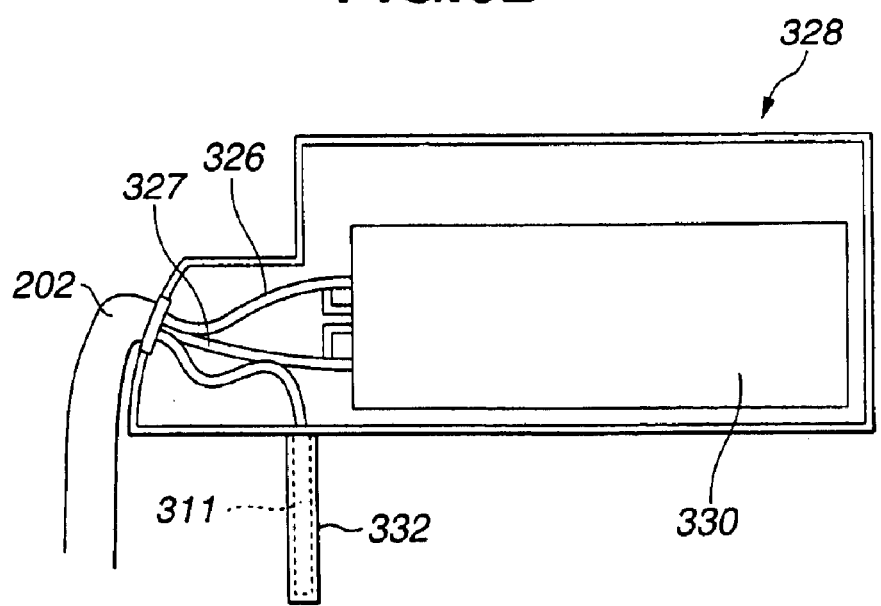
Figure 63:
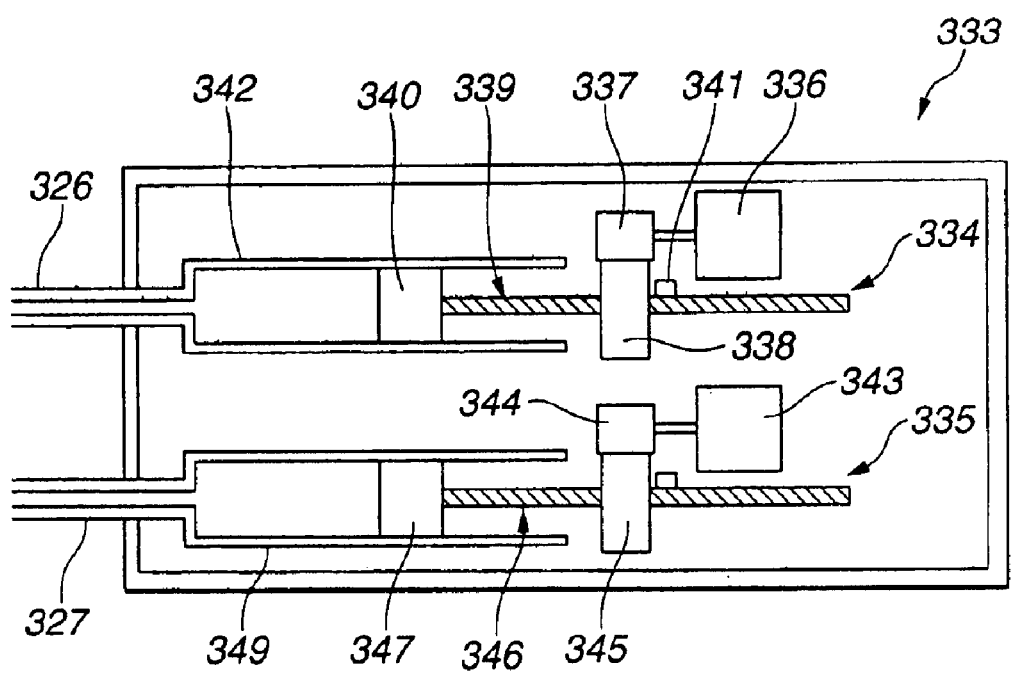
Figure 64:
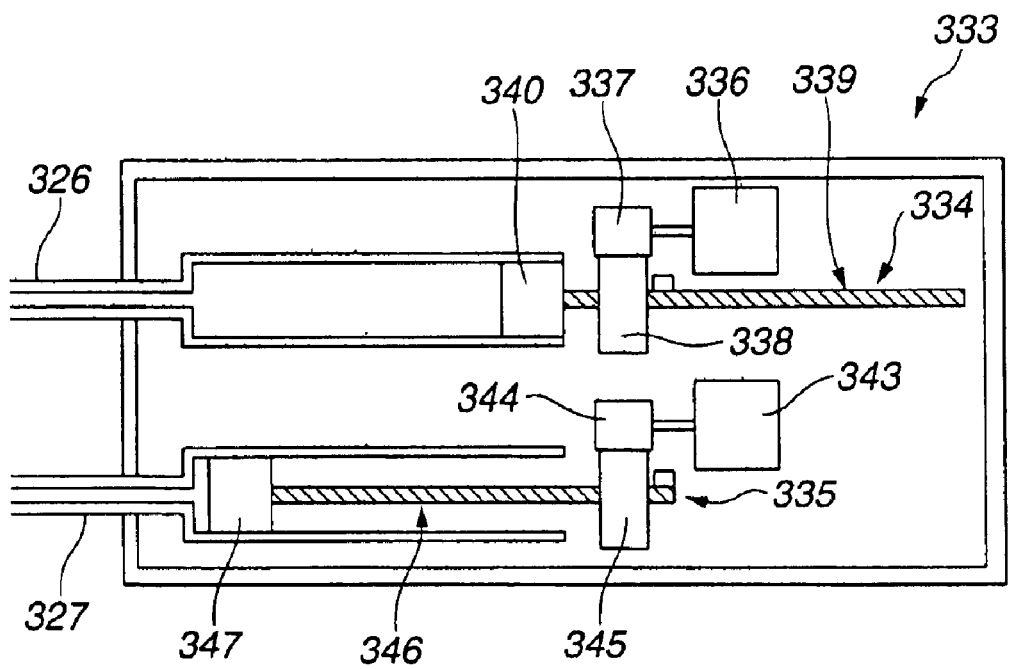

FIG. 59 to FIG. 64 are concerned with a fourteenth embodiment of the present invention. FIG. 59 shows the appearance of an endoscope system including a hydraulically angled endoscope. FIG. 60 is a sectional view for explaining the structure of the tip of an insertion member. FIG. 61 shows the structure of a drum. FIG. 62 shows the structure of a bending section drive unit. FIG. 63 is an explanatory diagram detailing a bending section driving mechanism. FIG. 64 shows movements to be made in the bending section driving mechanism.

As shown in FIG. 59, an insertion member 302 of an endoscope 300 is fastened to a drum 301 that includes a hydraulic angling unit which is a motor-driven angling unit and will be described later. The insertion member 302 is wound about the drum 301.

A tip 303 having an optical system, which will be described later, incorporated therein is formed as the tip of the insertion member 302. A bending section 304 and a flexible tube 305 are concatenated proximally to the tip 303. The bending section 304 is bent by the hydraulic angling unit. The drum 301 is rotatably stowed in a case body 306 freely. A power cable is extended from near the center of the drum 301.

As shown in FIG. 60, the bending section 304 is formed adjacently to the tip of the insertion member 302, and the tip 303 is located to the bending section 304. An observation optical system 307 and a system of illumination lenses 308 are incorporated in the tip 303.

A CCD 309 for converting a view image into an image signal is located at the position of the image plane of the observation optical system 307. A signal line 310 over which the photoelectrically converted image signal is transmitted to a CCU that will be described later is led to the CCD 309.

On the other hand, a light guide 311 opens on the rear end of the system of illumination lenses 308. The other end of the light guide 311 is led to a light source unit, which will be described later, through the insertion member 302.

The bending section 304 consists of a plurality of joint pieces 312. The joint pieces 312 are rotatably concatenated using rivets 313 freely. The rear end of the rearmost joint piece 312 is fixed to the flexible tube 305. The joint pieces 312 are sheathed with a metallic braid 314 for fear a bendy rubber 315 covering the braid 314 may drop to a gap between adjoining joint pieces 312. This structure is the same as the structure of a bending section that is employed in an ordinary endoscope and can bend in four directions of vertical directions and lateral directions.

The bendy rubber 315 is sheathed with an armor 316, which is a metallic braid, over the overall length of the insertion member 302.

A first angling rod 317 and a second angling rod 318 are hit on the tip 303. Each joint piece 312 has angling rod bearers 319 that restricts the movements of the first angling rod 317 and second angling rod 318 to the movements in the longitudinal directions.

The proximal parts of the first angling rod 317 and second angling rod 318 are abutted against the tip surfaces of a first angling piston 320 and a second angling piston 321. Consequently, for example, when the angling piston 320 pushes the angling rod 317, one side of the tip 303 is pressed to bend the bending section 304.

The first angling piston 320 and second angling piston 321 are inserted in a first angling cylinder 322 and a second angling cylinder 323 respectively, and moved when pushed with the pressure of oil in the cylinders.

A first stopper 324 and a second stopper 325 are locked at the tip sides of the first angling cylinder 322 and second angling cylinder 323 respectively in order to prevent the first angling piston 320 and second angling piston 321 from coming off.

A first hydraulic pipe 326 is joined with the first angling cylinder 322, and a second hydraulic pipe 327 is joined with the second angling cylinder 323. The hydraulic pipes 326 and 327 are led to the bending section drive unit, which will be described later, incorporated in the drum 301 through the insertion member 302.

As shown in FIG. 61, a hydraulic angling unit 328 that is the bending section drive unit, an angling control circuit unit 329, a light source unit 330, and a CCU 331 are incorporated in the drum 301. The light source unit 330 supplies illumination light. The CCU 331 produces a TV picture. The insertion member 302 is coupled to the hydraulic angling unit 328. The light source unit 330 and hydraulic angling unit 328 are coupled to each other using a light guide connector that will be described later. The angling control circuit unit 329 is coupled to the hydraulic angling unit 328.

As shown in FIG. 62, the proximal end of the insertion member 302 is fixed to the hydraulic angling unit 328 in a state where watertightness is ensured. A light guide 311 running through the insertion member 302 is inserted in a light guide connector 332 through the angling unit 328. The end surface of the light guide 311 is placed on the bottom of the light guide connector 332.

The first hydraulic pipe 326 and second hydraulic pipe 327 extended from the insertion member 302 are introduced to the hydraulic angling unit 328. Moreover, the hydraulic angling unit 328 includes bending section driving mechanisms 333. The first hydraulic pipe 326 and second hydraulic pipe 327 are coupled to the bending section driving mechanisms 333.

The bending section driving mechanisms will be detailed with reference to FIG. 63.

For brevity's sake, since the bending section driving mechanism responsible for vertical angling and the bending section driving mechanism responsible for lateral angling are identical to each other, only the bending section driving mechanism responsible for vertical angling will be described below. The description of the bending section driving mechanism responsible for lateral angling will be omitted.

As illustrated, the bending section driving mechanism 333 consists of two pairs of a first driving mechanism 334 and a second driving mechanism 335 that are driving sources.

The first driving mechanism 334 includes a first motor 336. A first driving gear 337 serving as a driving force converting mechanism is attached to the shaft of the first motor 336. A first driven gear 338 is engaged with the first driving gear 337. A first driving shaft 339 having a screw threaded on the periphery thereof is engaged with the center part of the first driven gear 338.

The first motor 336, first driving gear 337, and first driven gear 338 are rotatably placed on the frame of the bending section driving mechanism 333 freely, though the placement is not illustrated. A first hydraulic piston 340 is fixed to the tip of the first driving shaft 339. A key groove is cut in the first driving shaft 339 in the longitudinal direction of the first driving shaft 339. A first detent 341 is fitted in the key groove. This causes the first driving shaft 339 to advance or withdraw.

The first hydraulic piston 340 is inserted in a first hydraulic cylinder 342, and the first hydraulic pipe 326 is joined with the first hydraulic cylinder 342.

The other second driving mechanism 335 consists of a second motor 343, a second driving gear 344, a second driven gear 345, a second driving shaft 346, a second hydraulic piston 347, a second detent 348, a second hydraulic cylinder 349, and a second hydraulic pipe 327. The second driving mechanism 335 has the same structure as the aforesaid driving mechanism 334.

The motors 336 and 343 included in the bending section driving mechanism 333 are connected to the angling control circuit unit 329 over electric cables that are not shown. Moreover, the motors 336 and 343 are controlled by a control circuit, which is not shown, included in the angling control circuit unit 329. The motor-driven angling control circuit unit, that is, the angling control circuit unit 329 is logically connected to an angling device that is not shown. Moreover, an electric cable extended from the CCD 309 incorporated in the tip 303 is led to the CCU 331. The CCU 331 converts an image signal into a TV signal and transfers the TV signal to an imaging device such as a monitor located outside the drum 301. The CCU 331 includes a power supply that supplies power to the light source unit 330 and angling control circuit unit 329.

Now, actions to be performed in the present embodiment will be described below.

When power is supplied to the power supply in the CCU 331 over a power cable, power is supplied to the angling control circuit unit 329 through the CCU 331. An angling command issued responsively to a manipulation performed on the angling device is sent to the motor-driven angling control circuit unit that is the angling control circuit unit 329. The angling control circuit unit 329 converts the command into a control signal that is sent to a motor. The motor rotates in a predetermined direction in response to the control signal.

Initially, the hydraulic pistons 340 and 347 are, as shown in FIG. 63, located at initial positions. When the first motor 336 rotates, the first driving gear 337 rotates. This causes the first driven gear 338 engaged with the first driving gear 337 to rotate. At this time, the first driven gear 338 does not move in the longitudinal directions. The first driving shaft 339 therefore axially advances or withdraws with the rotation of the first driven gear 338.

For bending the bending section 304, an angling command is issued responsively to a manipulation performed on the angling device. This causes the first hydraulic piston 340 and second hydraulic piston 347 to move in opposite directions. Consequently, the angling pistons located to the first and second hydraulic pistons move in the opposite directions.

Specifically, as shown in FIG. 64, for example, the first hydraulic piston 340 withdraws and the second hydraulic piston 347 advances. Consequently, the first hydraulic pipe 327 is pressured and the second angling cylinder 323 is pressured. When the second angling cylinder 323 is pressured, the second hydraulic piston 347 is thrust forwards. When the second angling piston 321 is thrust forwards, the second angling rod 318 is thrust forwards. Accordingly, the first angling rod 317 is pushed back and the first angling piston 320 is pushed back. When the first angling piston 320 is pushed back, the first hydraulic piston 340 is pressured. However, the first hydraulic piston 340 is pulled by the first motor 336, the pressure within the first hydraulic pipe 326 will not be intensified. Consequently, the bending section 304 bends upwards in FIG. 60.

When an angling command is issued to instruct angling in an opposite direction, the motors rotate in directions opposite to the aforesaid directions. Consequently, the bending section is bent in the opposite direction.

As mentioned above, an angling controller controls supply or discharge of oil to or from each hydraulic pipe responsively to a manipulation performed on the joystick that is not shown. Consequently, the bending section can be bent in a desired direction. The other components of the present embodiment, and the operation and advantage thereof are identical to those of the thirteenth embodiment.

While this invention has been described in detail referring to one preferred embodiment of the invention, it should be understood that the invention is not limited to that precise embodiment. Rather, many modifications and variation will be apparent to those skilled in the art without departing from the scope and sprit of the invention as defined in the appended claims.

What is claimed is:

1. An endoscope system comprising:
    an insertion member having an imaging element incorporated at a tip thereof and having a bending section included in the insertion member which is motor-driven to bend;
    a drum having the insertion member capable of being wound about the outer circumference thereof, the drum being rotatably arranged in a case;
    a drive unit including a driving source for driving a driving mechanism that drives the bending section;
    a signal processor for controlling the imaging element and also processing an electric signal sent from the imaging element to produce a video signal; and
    a motor-driven angling control circuit unit for controlling the movement of the bending section.

2. An endoscope system according to claim 1, comprising a light source unit for supplying illumination light to an illumination light transmitting means included in the insertion member.

3. An endoscope system according to claim 1, further comprising:
    a frame for holding the drum; and
    a bearing means fixed to the frame in order to rotatably hold the outer edge of the drum freely, which is located away from the center of rotation of the drum.

4. An endoscope system according to claim 3, wherein the bearing means rotatably holds the outer edge of one side surface of the drum freely, which is located away from the center of rotation of the drum.

5. An endoscope system according to claim 3, further comprising:
    a plurality of bearings fixed to one side surface of the drum coaxially with the drum; and
    an annular rail mounted on the frame in which the drum is supported and locked, serving as a receiving surface that receives the bearings fixed to the drum, and being concentric with the drum.

6. An endoscope system according to claim 5, wherein the bearings are made of ball bearings.

7. An endoscope system according to claim 6, wherein the bearings and the rail have concave and convex, of which cross sections are shaped like letter V, engaged with one another.

8. An endoscope system according to claim 3, wherein a coupling mechanism for electrically coupling electric equipment located inside the drum with electric equipment located outside the drum is provided near the center of rotation of the drum in the bearing means.

9. An endoscope system according to claim 1, further comprising:
    a first opening and a second opening opposed to a side surface of the drum provided on one surface of the stowage case;
    a cover member freely detachably attached over the tip of an extension, which juts out from the side surface of the drum and penetrates through the first opening, in order to cover the first opening; and
    a lid member detachably attached in order to cover the second opening,
    wherein an adjusting mechanism in the rotating drum is exposed by removing the cover member and the lid member.

10. An endoscope system according to claim 9, wherein the first opening is a substantially round opening, and the cover member is substantially round and has a diameter larger than at least the inner diameter of the first opening.

11. An endoscope system according to claim 9, wherein the adjusting mechanism is a mechanism to adjust the bending section provided in the insertion member of the endoscope, and includes at least an angulation wire adjusting unit.

12. An endoscope system according to claim 9, wherein the adjusting mechanism can be adjusted from outside the case by being exposed.

13. An endoscope system according to claim 1, further comprising a flexible flat cable over which signals are transferred between first electric equipment provided inside the case outside the rotating drum and both or either of the endoscope and the rotating drum, wherein:
    the flat cable is curled around the center rotation shaft of the rotating drum; and
    when the flat cable is extended from the center rotation shaft, a sufficiently large distance is preserved for electric isolation between the flexible flat cable and a metallic part of the rotating drum and between the flexible flat cable and second electric equipment incorporated in the rotating drum.

14. An endoscope system according to claim 13, wherein primary voltage is applied to the flexible flat cable, and secondary voltage is applied to the second electric equipment incorporated in the rotating drum.

15. An endoscope system according to claim 13, wherein a sufficiently large distance is preserved for electric isolation with an isolator interposed between the metallic part of the rotating drum opposed to the flexible flat cable and the second electric equipment.

16. An endoscope system according to claim 13, wherein a stowage for the flexible flat cable is made of a resin that is an electrically insulating material, and a sufficiently large distance is preserved for electric isolation between the metallic part of the rotating drum that comes into contact with the stowage and the flexible flat cable.

17. An endoscope system according to claim 13 or 14, wherein the electric equipment incorporated in the drum is a printed-circuit board electrically coupled to the flexible flat cable, and a flexible thin-film isolator sheet such as a Mylar sheet is placed in a space created between the printed-circuit board and the flexible flat cable.

18. An endoscope system according to claim 13 or 14, wherein a printed-circuit board is electrically coupled to each of the first electric equipment located outside the drum and the flexible flat cable, and a flexible thin-film isolator sheet such as a Mylar sheet is placed in a space created between the printed-circuit board and the flexible flat cable.

19. An endoscope system according to claim 16, wherein the flexible flat cable electrically coupled to the second electric equipment is inserted into a stowage for the flexible flat cable from near the center of rotation of the rotating drum, passed through the interior of a cylindrical member placed coaxially with the rotating drum, drawn out from a notch, which is formed in the cylindrical surface of the cylindrical member, while being clamped by a clamp member, and wound about the cylindrical surface.

20. An endoscope system according to claim 13, wherein the flexible flat cable comprises a first flat cable and a second flat cable that are separated from each other, and the first flat cable and the second flat cable are stowed in two adjacent stowages.

21. An endoscope system according to claim 20, wherein a video signal channel for transmitting a video signal and a power channel for transmitting power are provided at the side of the first flat cable and at the side of the second flat cable, respectively.

22. An endoscope system according to claim 1, further comprising a plurality of devices that is stowed in the drum, and transfers illumination light or electric signals used to control or activate the endoscope, wherein:
among the devices, a light source device for supplying illumination light, with which an object of observation is illuminated, from the tip of the endoscope is placed close at the side of one of spaces in the drum, and the other devices are placed close at the side of the other space in the drum.

23. An endoscope system according to claim 22, wherein an adiabatic panel is interposed between the light source device and the other devices excluding the light source device.

24. An endoscope system according to claim 23, wherein electric parts are mounted on the adiabatic panel in order to thus form a printed-circuit board.

25. An endoscope system according to claim 1, wherein:
the insertion member is extended from the drum; the endoscope system further comprising
a holding mechanism for rotatably holding the drum; and
a detecting means for detecting information corresponding to a length by which the insertion member is wound about the drum, and electrically outputting the detected information.

26. An endoscope system according to claim 25,
said detecting means for detecting information corresponding to a length by which the insertion member is wound about the drum mechanically detects the detecting information.

27. An endoscope system according to claim 26, wherein the detecting means is a number-of-rotations detecting means for detecting the number of rotations of the drum associated with the length by which the insertion member is wound.

28. An endoscope system according to claim 27, wherein the number-of-rotations detecting means includes a sliding resistor that has a lever coupled to a variable resistance terminal thereof, and the lever is mechanically freely movable between a point on the drum at which the insertion member is started to be wound and a point thereon at which the insertion member is wound to the greatest extent.

29. An endoscope system according to claim 26, wherein the detecting means detects information irrespective of whether the power supply is turned on or off.

30. An endoscope system according to claim 26, wherein the detecting means includes:
a drum-side gear formed on the periphery of a side panel of the drum as an integral part of the side panel or as a part independent of the side panel;
a gear member provided to the frame member in which the drum is held, and engaged with the drum-side gear;
a male screw member to be rotated responsively to the rotation of the drum;
a sliding member screwed to the male screw member and axially movable responsively to the rotation of the male screw member;
a guide member for restricting rotation of the sliding member; and
a sliding resistor fixed to the frame member, moved together with the sliding member while engaged with part of the sliding member, and having a lever coupled to a variable resistance terminal thereof.

31. An endoscope system according to claim 27, wherein the number-of-rotations detecting means includes a multi-rotation variable resistor for mechanically movably a rotation shaft freely connected to a variable resistance terminal thereof, and the rotation shaft can freely rotate or move between a point on the drum at which the insertion member is started to be wound and a point thereon at which the insertion member is wound to the greatest extent.

32. An endoscope system according to claim 26, further comprising a control circuit for acquiring the information from the detecting means, and controlling based on the acquired information whether an electric equipment should be activated or inactivated.

33. An endoscope system according to claim 32, wherein the electric equipment includes a light source lamp, and the control circuit controls based on the acquired information whether the light source lamp should be activated or inactivated.

34. An endoscope system according to claim 32, wherein the electric equipment includes a drive unit for performing motor-driven bending of the bending section, and the control circuit controls based on the acquired information whether the drive unit should be activated or inactivated.

35. An endoscope system according to claim 32, wherein the electric equipment includes a camera control unit, and the control circuit controls based on the information whether the camera control unit should be activated or inactivated.

36. An endoscope system according to claim 34, wherein the bent bending section is brought back to a neutral state when enabled motor-driven angling is disabled.

37. An endoscope system according to claim 1, wherein a magnitude of traction exerted in pulling an angulation wire so as to bend the bending section to the greatest extent is determined by software.

38. An endoscope system according to claim 26, wherein information from the detecting means is acquired, and a magnitude of traction exerted in pulling the angulation wire using the drive unit is varied corresponding to the number of rotations of the drum based on the acquired information.

39. An endoscope system according to claim 32, wherein whether the electric equipment is activated or inactivated is displayed on a screen on which an image picked up by an imaging means incorporated in the insertion member is displayed.

40. An endoscope system according to claim 1, further comprising:
   a frame member for rotatably bearing the drum freely;
   a first gear provided on the outer circumference of at least one of a pair of side panels placed on the side panel of the drum;
   a second gear engaged with the first gear for fixing to the frame member;
   a male screw member formed on the shaft of the second gear extended along the axis of rotation of the drum, hung between at least the pair of side panels, and rotated while interlocked with the drum;
   a first stopper member screwed to the male screw member, and capable of reciprocating between the pair of side panels;
   second and third stoppers provided on the inner surfaces of the pair of side panels so that the second and third stoppers will abut on the first stopper so as to prohibit further rotation of the drum when the insertion member of the endoscope is taken up or thrust out to the greatest extent, and;
   a third gear fixed to the frame member so that the third gear will be freely engaged with or freed from the first gear;
   a constraining member for constraining the third gear to move towards the first gear so that the third gear will be engaged with the first gear; and
   a clutching mechanism for prohibiting rotation of the drum in a direction of rotation permitting thrusting out of the insertion member of the endoscope when the third gear is engaged with the first gear.

41. An endoscope system according to claim 40, wherein the clutching mechanism includes an operator lever mechanism capable of being freely set to a position permitting the third gear to be engaged with the first gear or a position permitting the third gear to be freed from the first gear.

42. An endoscope system according to claim 41, further comprising a case body in which the drum is stowed, and a lid placed on the case body, wherein:
   when the third gear is freed from the first gear, at least part of the operator lever mechanism is located over the part of the case body engaged with the lid, and the lid cannot therefore be placed on the case body.

43. An endoscope system according to claim 41, wherein when an operator lever is pushed manually, the operator lever mechanism frees the third gear that is engaged with the first gear owing to the constraining member, and enables the drum to rotate freely.

44. An endoscope system according to claim 41, wherein when an operator lever is pushed to be turned, the operator lever mechanism frees the third gear that is engaged with the first gear owing to the constraining member, and keeps a rotating state of the drum in a free state.

45. An endoscope system according to claim 1, further comprising:
   a rotational panel placed on a side panel of the drum, and including a lever used to rotate the drum;
   a torque conveying member for conveying torque of the rotational panel to the drum; and
   a mechanism for conveying torque, which is conveyed by the torque conveying member in order to produce one-way rotation, to the drum.

46. An endoscope system according to claim 45, wherein the mechanism is a one-way clutch.

47. An endoscope system according to claim 45, wherein the mechanism includes a sprocket and a claw that moves in one direction alone to engage with the sprocket.

48. An endoscope system according to claim 1, further comprising a mechanism for adjusting a level of torque to stabilize the torque that causes the drum to rotate.

49. An endoscope system according to claim 1, further comprising:
   a frame for rotatably holding the drum freely;
   a shock absorber interposed between the outer surface of the frame and the inner surface of the case opposed to the outer surface in order to absorb shocks applied in a direction parallel to the outer surface and inner surface; and
   a holding means for holding the shock absorber with the respective edges of the shock absorber, which extend along the direction parallel to the outer surface and inner surface, abutted on the case and the frame respectively.

50. An endoscope system according to claim 49, wherein the case is structured to be divided in directions perpendicular to the direction parallel to the outer surface and inner surface.

51. An endoscope system according to claim 49, wherein the case includes a case body that can be opened and closed in the directions and a lid member.

52. An endoscope system according to claim 49, wherein the case is shaped like a box and has shock absorbers, which absorb shocks, attached to the respective corners of the outer surface thereof.

53. An endoscope system according to claim 49, wherein the shock absorbers are shaped like plates whose length in the directions is larger than the thickness of the outer surface of the frame and the thickness of the inner surface of the case.

54. An endoscope system according to claim 49, wherein the case is molded or die-cast using a resin, and the frame is made of a metal.

55. An endoscope system according to claim 51, wherein a panel is fixed to the frame in order to block an opening of the case body, which is covered by the lid member, perpendicularly to the directions.

56. An endoscope system according to claim 55, wherein a monitor on which an endoscopic image is displayed is placed between the panel and the inner surface of the lid member.

57. An endoscope system according to claim 1, further comprising:
   a panel placed on a surface of the case beyond which the insertion member is taken up or thrust out;
   a first elastic member jutted from the panel to the outside of the case so that the insertion member can be loosely inserted in the first elastic member; and a second elastic member having a hole whose diameter is smaller than the outer diameter of the insertion member in a natural state, and mounted at the tip of the first elastic member, the insertion member being passed through the hole.

58. An endoscope system according to claim 57, wherein: the first elastic member has a bellows-like extensible part that communicates with a part thereof mounted on the panel and the tip thereof; a screw is threaded on the outer circumference of the extensible part; a hole whose diameter is larger than the diameter of the insertion member is formed at the tip of the first elastic member; a first metallic member having a screw threaded thereon is fixed on the outer circumference; a second metallic member is screwed to the screw threaded on the first metallic member; and a hole whose diameter is substantially the same as the diameter of the hole in which the second metallic member is formed on the first metallic member.

59. An endoscope system according to claim 57, wherein a brush-like member with a thin wire is fixed to the circumference of the second elastic member.

60. An endoscope system according to claim 57, wherein a second electrical equipment for the endoscope is stowed in an internal space of the drum, and a first electric equipment is stowed together with the drum in the case.

61. An endoscope system according to claim 1, wherein: a round opening opposed to a side panel of the drum is formed in one surface of the case; a round cover member whose diameter is larger than the inner diameter of the opening is provided at the tip of an extension that juts the opening from the side panel of the drum; and an elastic member pressured on the inner side surface of the cover member is provided to the perimeter of the opening.

62. An endoscope system according to claim 61, wherein the elastic member has the proximal part thereof fixed to the opening, and has the tip thereof shaped like a fin whose free end is pressured against the round cover.

63. An endoscope system according to claim 61, wherein a handle member used to rotate the drum is provided on the outer side surface of the round cover member.

64. An endoscope system according to claim 63, wherein at least a holder of the handle member can be held while being folded towards the side panel of the drum.

65. An endoscope system according to claim 64, wherein a direction in which the handle member is folded is opposite to a direction of rotation permitting taking up of the insertion member.

66. An endoscope system according to claim 61, wherein: the handle member has the proximal stationary part thereof fixed to the round cover member; the proximal stationary part has a cylindrical part continuous to a hemispherical apex portion thereof, and has the cylindrical part and hemispherical apex portion thereof hollowed; a groove is formed to open on outside at the apex of the proximal stationary part, descend spirally to the middle of the outer circumference of the proximal stationary part, and further descend perpendicularly towards the bottom of the proximal stationary part; a shaft of the handle member is passed through the groove; an elastic member for constraining the proximal part of the holder to come into contact with the proximal stationary part is interposed between the handle-holder mounted on the outer circumference of the shaft and the shaft; and the shaft is turned down along the groove due to the constraining force in a natural state.

67. An endoscope system according to claim 66, wherein the proximal stationary part of the handle member is fixed to the round cover member so that the shaft of the handle member will be turned down in a direction opposite to a direction, in which the handle member is turned at the time of taking up the insertion member, on a line segment linking the center of the proximal stationary part and the center of the rotating drum.

68. An endoscope system according to claim 61, wherein the extension is made of an elastic material such as a rubber.

69. An endoscope system according to claim 1, further comprising a case in which a frame accommodating the drum and peripheral equipment is stowed with a shock absorber between them, wherein an operator panel having at least operator switches, which are used to control the peripheral equipment, and a port through which the insertion member of the endoscope is taken up or thrust out is exposed on one surface of the case and fixed to the frame.

70. An endoscope system according to claim 69, wherein an intake vent and a discharge vent through which the peripheral equipment is aerated or deaerated are provided on the operator panel, and provided at right angles with respect to the perpendicular axis of the case placed to be usable.

71. An endoscope system according to claim 70, wherein the vents have eaves-like members projected from the upper sides thereof.

72. An endoscope system according to claim 69, wherein an elastic member is attached on the outer circumference of the operator panel in order to ensure watertightuess for the case.

73. An endoscope system according to claim 1, wherein the bending section has a fluid chamber that can be stretched in the axial direction of the bending section due to fluid pressure, and the bending section drive unit serves as a fluid supply/discharge member for supplying or discharging fluid to or from the fluid chamber.

74. An endoscope system according to claim 73, wherein the fluid supply/discharge member includes a cylinder/piston mechanism for supplying or discharging fluid to or from the fluid chamber, an operation motor, and a driving force converting mechanism for advancing or withdrawing the piston along with the rotation of the operation motor.

75. An endoscope system according to claim 1, further comprising an operation rod that has one end thereof coupled to the bending section, a cylinder provided behind the bending section, and a piston abutted on the other end of the operation rod, wherein the bending section drive unit serves as a fluid supply/discharge member that supplies or discharges fluid to or from the cylinder.

76. An endoscope system according to claim 75, wherein the fluid supply/discharge member includes a driving cylinder/piston mechanism that supplies or discharges fluid to or from the cylinder, an operation motor, and a driving force converting mechanism that advances or withdraws the driving piston along with the rotation of the operation motor.

77. An endoscope system according to claim 1, wherein the drive unit, the signal processor, and the motor-driven angling control circuit rotate together with the drum.

78. An endoscope system according to claim 2, wherein the light source unit rotates together with the drum.

79. An endoscope system according to claim 1, wherein a holding member to rotate the drum is exposed outside the case.

80. An endoscope system comprising:
an insertion member having a solid-state imaging element at a tip thereof, and including a bending section;
a drum about which the insertion member is wound with the proximal end of the insertion member fastened to the drum;
a bending section drive unit integrated with the drum, and used to bend the bending section;

an angling control circuit unit for controlling the bending section drive unit;

a video signal processing unit for processing a signal of the solid-state imaging element; and a case in which the drum is stowed.

81. An endoscope system according to claim 80, further comprising an angling input control unit extended from a stowage for the insertion member to be used to transmit an angling control command to the angling control circuit unit.

82. An endoscope system according to claim 80. wherein the case has a passage hole through which the insertion member is thrust out.

* * * * *